(12) United States Patent
Yoritaka et al.

(10) Patent No.: US 8,246,645 B2
(45) Date of Patent: *Aug. 21, 2012

(54) LANCET ASSEMBLY AND PRICKING DEVICE

(75) Inventors: Kitamura Yoritaka, Tokyo (JP); Abe Teruyuki, Tokyo (JP); Seki Kazuharu, Tokyo (JP)

(73) Assignee: Izumi-Cosmo Company, Limited, Osaka (JP)

( * ) Notice: Subject to any disclaimer, the term of this patent is extended or adjusted under 35 U.S.C. 154(b) by 881 days.

This patent is subject to a terminal disclaimer.

(21) Appl. No.: 11/992,771

(22) PCT Filed: Sep. 25, 2006

(86) PCT No.: PCT/JP2006/318978
§ 371 (c)(1),
(2), (4) Date: Jul. 7, 2008

(87) PCT Pub. No.: WO2007/037207
PCT Pub. Date: Apr. 5, 2007

(65) Prior Publication Data
US 2009/0143810 A1   Jun. 4, 2009

(30) Foreign Application Priority Data

Sep. 29, 2005  (JP) .............................. P2005-284789
Jun. 13, 2006  (JP) .............................. P2006-163499

(51) Int. Cl.
*A61B 17/14* (2006.01)
(52) U.S. Cl. ........................................ 606/181; 600/583
(58) Field of Classification Search ................. 606/181, 606/182, 183; 600/573–584; 604/506, 198, 604/110
See application file for complete search history.

(56) References Cited

U.S. PATENT DOCUMENTS 5,385,571 A   1/1995   Morita
7,150,755 B2  12/2006  Levaughn et al.
(Continued)

FOREIGN PATENT DOCUMENTS

EP   1 806 095   7/2007
(Continued)

OTHER PUBLICATIONS

International Preliminary Report on Patentability issued Apr. 10, 2008 in the International (PCT) Application No. PCT/JP2006/318978.

(Continued)

*Primary Examiner* — Victor Nguyen
(74) *Attorney, Agent, or Firm* — Wenderoth, Lind & Ponack, L.L.P.

(57) ABSTRACT

A lancet assembly includes a lancet and a lancet holder that houses the lancet, wherein the lancet includes a lancet body, a lancet cap and a pricking component, the pricking component is situated in both of the lancet body and the lancet cap, the tip of the pricking component is covered with the lancet cap, and the lancet cap and the lancet body are integrally connected together by a bridging component when the lancet cap is pressed in the pricking direction with the lancet body attached to the lancet holder, the bridging component is broken so that the lancet cap is separated from the lancet body. Thereafter, when the separated lancet cap is pressed further: in the pricking direction, the separated lancet cap moves to a position that is off the pricking pathway of the pricking component.

23 Claims, 60 Drawing Sheets

U.S. PATENT DOCUMENTS

| | | | |
|---|---|---|---|
| 7,322,996 B2 * | 1/2008 | Taylor et al. | 606/181 |
| 2004/0230216 A1 | 11/2004 | Levaughn et al. | |
| 2004/0260325 A1 | 12/2004 | Kuhr et al. | |
| 2005/0015020 A1 | 1/2005 | Levaughn et al. | |
| 2006/0178600 A1 | 8/2006 | Kennedy et al. | |
| 2007/0088377 A1 | 4/2007 | Levaughn et al. | |
| 2007/0225742 A1 | 9/2007 | Abe et al. | |
| 2008/0119883 A1 * | 5/2008 | Conway et al. | 606/181 |

FOREIGN PATENT DOCUMENTS

| | | |
|---|---|---|
| EP | 1 929 949 | 6/2008 |
| JP | 2000-245717 | 9/2000 |
| JP | 2004-141389 | 5/2004 |
| JP | 2004-283568 | 10/2004 |
| JP | 2006-512932 | 4/2006 |
| WO | 03/071940 | 9/2003 |
| WO | 2005/110225 | 11/2005 |
| WO | 2006/038340 | 4/2006 |
| WO | 2007/037207 | 4/2007 |

OTHER PUBLICATIONS

International Search Report issued Jul. 3, 2007 in the International (PCT) Application No. PCT/JP2007/061375.

International Search Report issued Oct. 17, 2006 in the International (PCT) Application No. PCT/JP2006/318978.

* cited by examiner (a)

(b)

(a)

(b)

(a)

(b)

LANCET ASSEMBLY AND PRICKING DEVICE

TECHNICAL FIELD

The present invention relates to a lancet assembly composed of a lancet and a lancet holder (which may also be called "lancet case") that houses the lancet. The present invention also relates to an injector used in combination with the lancet assembly. Furthermore, the present invention relates to a pricking device composed of the lancet assembly and the injector. The pricking device is used for pricking a predetermined region of a human body with a sharp pricking component (e.g. a needle) so as to take a sample of body fluids (e.g. blood).

BACKGROUND OF THE INVENTION

In order to measure a blood sugar level of the patient, it is required to take a sample of the blood from the patient with diabetes. At present, various pricking devices have been used to collect a small amount of the blood sample. The pricking device is generally composed of a lancet and an injector wherein the lancet has a pricking component capable of puncturing a predetermined region of the patient's body. The injector has a function of launching the lancet toward a predetermined region. The pricking device is set up for use by loading (or charging) the lancet into the injector. Due to an expansion of the compressed spring of the injector, the lancet is launched toward the predetermined region, and thereby the predetermined region is pricked.

A pricking operation by using the pricking device requires the following nine steps from the loading of the lancet into the injector until the taking out the used lancet from the injector:

(1) Removing an injector cap from the injector;
(2) Setting the lancet into the injector;
(3) Removing a lancet cap from the lancet so as to expose the tip of the pricking component;
(4) Putting the injector cap (which has been removed in step (1)) onto the injector;
(5) Cocking the injector to put the lancet in the loaded state (i.e. make the lancet ready to be launched);
(6) Applying the front end opening of the injector onto a region to be pricked, and then pressing a trigger button to launch the lancet;
(7) Removing the injector cap from the injector;
(8) Putting a protective cap on the exposed tip of the pricking component so as to shield the tip of the pricking component from its surroundings; and
(9) Discharging the lancet from the injector, and then disposing of the used lancet.

Carrying out the above nine steps sequentially is cumbersome and thus it is desired to reduce the number of the steps.

When taking a sample of the blood by using a pricking device, a particular attention must be paid to the handling of the used lancet. In the used lancet, the tip of the pricking component is exposed on the front end of a lancet body, and there may be the patient's blood adhered to the pricking component (particularly the tip of the pricking component) due to the pricking. If the body of a person other than the subject of the blood sampling (for example, a nurse or medical practitioner who collects the blood sample) accidentally should touch the tip of the pricking component, the body of such person may be pricked by the pricking component. This will result in a wound of the body through which the patient's blood may enter the body (i.e. the body of the nurse or medical practitioner), and thus posing a risk of the infection disease.

The presently-used pricking devices are not necessarily designed with due consideration with respect to the handling of the used lancet. It has been proposed to cover the exposed tip of the pricking component with a protective cap after the pricking component is used (see U.S. Pat. No. 5,385,571). However, the covering the tip of the pricking component with the protective cap will in itself carry risk. That is, the lancet with the exposed tip of the pricking component has to be handled when the protective cap is placed thereon. Therefore the risk as described above is still not eliminated.

As will be understood from the above, the pricking device requires utmost attention in handling the used lancet. Due to this, there is a demand for a pricking device that allows it to be disposed of in safety after use (i.e. after the pricking operation).

When the blood sampling is carried out, the pricking component serves to make contact with the body. From this point of view, a sterilization assurance of the pricking component (namely, hygienic soundness of the lancet) is crucial. Thus it is preferable that a lancet holder for housing the lancet has as less area of the opening as possible.

There is also a demand for a lancet capable of controlling the depth of pricking precisely. Particularly such a pricking device is desired that allows it to achieve a constant depth of the pricking, irrespective of the force required for applying the device onto the body.

SUMMARY OF THE INVENTION

The present invention has been devised to address the problems described above. Therefore, an object of the present invention is to provide a pricking device (i.e. pricking device using a lancet) capable of collecting a blood sample with a reduced number of steps, and disposing of the used lancet more safely after pricking.

In a first aspect, the present invention provides a lancet assembly comprising a lancet and a lancet holder that contains the lancet, wherein the lancet comprises a lancet body, a lancet cap and a pricking component in which the lancet body and the lancet cap are made of resin and the pricking component is made of metal, the pricking component is situated in both of the lancet body and the lancet cap, the tip of the pricking component (i.e. distal end portion of the pricking component) is covered with the lancet cap, and the lancet cap and the lancet body are integrally connected together by a bridging component;

the lancet holder has an opening end, and, a pricking opening in a face opposed to the opening end;

when the lancet cap is pressed in the pricking direction (i.e. direction from the opening end toward the pricking opening) while the lancet body is still attached to the lancet holder, the bridging component is broken so that the lancet cap is separated from the lancet body, and thereby the tip of the pricking component is exposed while the pricking component remains situated in the lancet body; and when the separated lancet cap is pressed further in the pricking direction, the separated lancet cap moves within the lancet holder to a position that is off the pricking pathway of the pricking component.

In a preferred embodiment, the lancet assembly of the present invention is characterized in that the lancet is housed in the lancet holder such that the lancet does not protrude from the lancet holder, and that the lancet holder has openings (i.e. "opening end" and "the pricking opening" as described above) only on each of its end faces whereas the lancet holder has no openings on its side faces.

In a preferred embodiment of the lancet assembly of the present invention, the lancet cap has such a configuration that it can engage with a lancet cap removing part provided in an injector (such injector serves to launch the pricking component). Therefore, the lancet cap removing part can engage with the lancet cap, upon loading the lancet assembly into the injector by inserting the lancet holder into the injector through the front end opening of the injector (in this case, the lancet cap removing part enters the lancet holder through the opening end of the lancet holder). The lancet body is secured to the lancet holder, and thus when the lancet holder is inserted further while the lancet cap and the lancet cap removing part are still in engagement, the force for moving the lancet cap and the lancet body away from each other is generated. This results in the breaking of the bridging component interconnecting the lancet cap and the lancet body. More specifically, the lancet body is secured to the lancet holder, and thereby the lancet body can move together with the lancet holder in the direction of the insertion. On the other hand, the lancet cap is not secured to the lancet holder, wherein the lancet cap and the lancet cap removing part are in engagement and thereby the lancet cap is pressed by the lancet cap removing part. As a result, the lancet body and the lancet cap are subjected to forces for moving them away from each other. When the forces eventually exceed a predetermined threshold, the bridging component which interconnects the lancet cap and the lancet body is broken. The breaking of the bridging component causes the lancet cap to be separated from the lancet body, and thereby the tip of the pricking component is exposed. When the lancet holder is further inserted into the injector after the breaking of the pricking component, the separated lancet cap is pushed by the lancet cap removing part, and thereby the separated lancet cap moves within the lancet holder and finally reaches a position that is off the pricking pathway.

The lancet assembly of the present invention is characterized in that the loading (i.e. charging of the lancet assembly into the injector) makes it possible not only for the lancet cap to be separated from the lancet body, but also for the separated lancet cap to move to the position that is off the pricking pathway. The term "forward" used herein substantially means the pricking direction, that is, the direction in which the pricking component is launched (or the direction in which the lancet body with the tip of the pricking component exposed is launched). The term "backward" used herein substantially means the direction opposite to the forward direction. Also the phrase "off the pricking pathway of the pricking component" used herein substantially implies that the separated lancet cap does not impede the forward launching of the lancet body (more specifically, the lancet body having the exposed tip of the pricking component) and the pricking of the pricking component in the pricking direction. Since the launching and the pricking are not impeded by the separated lancet cap, the pricking component can puncture the predetermined region. Preferably, the phrase "off the pricking pathway of the pricking component" implies that the lancet body does not touch the separated lancet cap at all.

In the lancet assembly of the present invention, it is preferable that the lancet holder has a guide (preferably "guide channel") formed on each of its opposing inner walls so as to guide the lancet body in the pricking direction, whereas the lancet body has a guided component for slotting into the guide. In this case, it is preferable that the lancet body is attached or secured to the lancet holder by making contact a protrusion A (which may be called "protrusion for preventing movement") formed on the guided component and a protrusion B (which may be called "stopper protrusion") formed within the guide with each other. The guide or the guide channel may be, for example, formed from two rails disposed at a space from each other in parallel on the inner wall of the lancet holder. It is preferred that the lancet body is secured to the lancet holder by locating the one protrusion B between the two protrusions A.

According to the present invention, upon the loading of the lancet assembly, there is occurred the breaking of the bridging component which interconnects the lancet cap and the lancet body. That is, the breaking occurs while the lancet assembly with the lancet body housed in the lancet holder is being inserted into the injector through the front end opening of the injector. It is preferable that the bridging component has such a form or shape that it is easily broken (therefore, the bridging component may also be called "weakened portion" or "easily-broken portion"). For example, the bridging component may be a rod-like component with small diameter, formed of the same resin as that of the lancet cap and the lancet body. Such rod-like component is provided preferably in such a configuration that it bridges between the lancet cap and the lancet body. It is more preferable that the two rod-like components are disposed symmetrically with respect to the pricking component. The bridging component may have a notch. In this case, the bridging component can be more easily broken due to the notch.

Since the lancet cap can be separated from the lancet body, the tip of the pricking component is exposed while the pricking component remains situated in the lancet body. When the lancet holder is inserted further into the injector after the separation, the separated lancet cap is pressed by the lancet cap removing part. Therefore, the lancet body and the lancet cap are subjected to the forces for moving them away from each other, which causes the separated lancet cap to move within the lancet holder and deviate from the pricking pathway. In order to guide the separated lancet cap to the position that is off the pricking pathway, it is preferable that the lancet holder is provided with a slope component whereas the lancet cap is provided with a sloped portion having a shape corresponding to the slope component.

In a preferred embodiment of the lancet assembly of the present invention, the lancet cap is provided with a pair of first wing parts. The pair of first wing parts extends toward the rear of the pricking component in substantially symmetrical configuration with respect to the pricking component. The first wing parts have, at their edges, engaging portions capable of complementarily engaging with the end of the lancet cap removing part. It is preferable that the pair of first wing parts extends firstly in a transverse direction of the pricking component and then extends toward the rear of the pricking component in a symmetrical configuration with respect to the pricking component. That is to say, it is preferable that the pair of first wing parts is in a generally C-letter shape as a whole.

In a preferred embodiment of the present invention, the rear end portion of the lancet body has an engaging portion capable of engaging with the plunger of the injector. For example, the engaging portion of the rear end portion of the lancet body fits into a recessed portion provided in the front end of the plunger wherein the recessed portion of the plunger is formed by partially splitting the front end of the plunger. In this case, the pushing the engaging portion of the lancet body can expand the front end of the plunger so that the engaging portion of the lancet body enters the front end of the plunger, and thereby the engaging portion slots into the front end. In another embodiment, the engaging portion of the rear end portion of the lancet body may fit into the front end of the plunger in a press fitting relationship. Due to such relationship, the rear end portion of the lancet body and the front end of the plunger of the injector can engage with each other when the lancet assembly is loaded in the injector by inserting the lancet holder through the front end opening of the injector. Accordingly, in a case where the lancet body is secured to the lancet holder, the inserting the lancet holder into the injector enables the lancet body to push the plunger backward (that is, the plunger can be retracted). When the plunger is pushed backward, the force required for launching the pricking component is stored in plunger. The injector of the present invention is configured such that the further retracting of the plunger is prevented after the separation of the lancet cap from the lancet body. When the plunger is prevented from being retracted further, the lancet body being in engagement with the plunger is prevented from being inserted further. Therefore, when the lancet holder is forced to move further in the direction of insertion after the prevention of the retracting of the plunger, the lancet holder is forced to move in the direction of insertion whereas the force resisting it is exerted on the lancet body. This causes the lancet holder and the lancet body to move away from each other, and thereby the lancet body is no longer secured to the lancet holder. More specifically, in a case where the lancet body is secured to the lancet holder through the contact between the protrusion A formed on the guided component of the lancet body and the protrusion B formed within the guide of the lancet holder, the further moving the lancet holder into the insertion direction causes the protrusion B of lancet holder to ride over the protrusion A of the lancet body (in other words, the protrusion A of the lancet body can ride over the protrusion B of the lancet holder). As a result, the contact between the protrusion A and the protrusion B ceases. The cease of the contact means that the lancet body is no longer secured to the lancet holder. Therefore, after the contact ceases, the lancet body can move in the pricking direction along the guide or in the direction opposite to the pricking direction along the guide.

In a preferred embodiment of the lancet assembly of the present invention, the lancet body is provided with a pair of second wing parts. The pair of second wing parts extends forward in substantially symmetrical configuration with respect to the pricking component. In this case, after the pricking is completed and the lancet assembly is ejected from the injector, the pair of second wing parts is enabled to make contact with or to hit a stopper surface provided in the lancet holder, which prevents the tip of the pricking component from protruding from the pricking opening. In other words, the spent lancet assembly, which has been removed from the injector after pricking, has such a configuration that the pair of second wing parts can make contact with or hit the stopper surface of the lancet holder. Due to this contact or hit, even if the used pricking component moves in the pricking direction, the tip of the pricking component would not protrude from the pricking opening. The stopper surface may be specially or separately provided within the lancet holder. However, it is preferable to use, as the stopper surface, the rear end face of the slope component provided in the lancet holder.

In a case where the lancet cap removing part enters into the lancet holder upon loading the lancet assembly into the injector, the second wing parts might be subject to the force by the lancet cap removing part so that it is significantly deformed inwardly or toward the inside. If such deformation is left to remain, the second wing parts might be permanently deformed due to its creeping effect. In this case, after the pricking is completed and the lancet assembly is removed from the injector (i.e. after the lancet cap removing part is removed from the inside of the lancet holder), the second wing parts might remain deformed due to the creeping effect. Such deformation of the second wing parts, if sustained, would prevent the second wing parts from making contact with the stopper surface of the lancet holder, thus eventually causing the tip of the pricking component to protrude from the pricking opening after pricking. Therefore, in a preferred embodiment of the present invention, the lancet assembly has such a configuration that the second wing parts are not kept in a significant deformed state from the commencement of the loading until the completion of the pricking. Specifically, the lancet cap removing part of the injector is provided with a groove (or continuous recess or continuous notch) for accommodating the pair of the second wing parts. Due to this, even when the lancet cap removing part enters the lancet holder upon the loading, the pair of second wing parts is placed in the groove such that the second wing parts are kept in no significant deformed state. In other words, in the state where the pricking component is ready to be launched (i.e. after the loading has been completed), the second wing parts lie in the grooves of the lancet cap removing part and are therefore keep from being deformed significantly. As a result, after the pricking is carried out and the lancet cap removing part is ejected from the lancet holder, the pair of second wing parts is not in its deformed state (i.e., there is no deformation attributable to the creeping effect in the second wing parts), and thus the pair of second wing parts can reliably make contact with or hit the stopper surface of the lancet holder.

The groove of the lancet cap removing part is bow-shaped so that it provides a sloped surface for the second wing parts. As a result, the movement of the lancet body in the pricking direction is not hampered upon pricking. In other words, there is no obstruction to the pricking direction movement of the second wing parts. Specifically, the second wing parts move along the bow-shaped groove (in the pricking direction) upon pricking, and thereby the second wing parts can move forward without expanding outwardly. This results in no contact between the second wing parts and the stopper surface. In this way, the lancet body can move forward without being hampered by the second wing parts upon pricking, and thus the tip of the pricking component can surely protrude from the pricking opening upon pricking.

In a preferred embodiment of the lancet assembly of the present invention, the pricking opening of the lancet holder is formed with such a small size as to carry out the pricking to substantially the same depth under substantially no influence (preferably under no influence) of the force of pressing the pricking device to the region to be pricked. The phrase "force of pressing", in this case, means the force exerted by the lancet holder onto the region to be pricked when the lancet holder is applied to such region for pricking. The pricking opening with a small size is preferably from 0.5 to 2.0 mm, more preferably from 1.0 to 1.5 mm in diameter.

In a second aspect, the present invention provides an injector used in combination with the lancet assembly described above (namely "lancet assembly of type A" to be described later) for launching the lancet body with the tip of the pricking component exposed.

Such injector comprises a plunger that is capable of engaging with the rear end portion of the lancet body, and thus capable of launching the lancet body in the pricking direction;

a lancet cap removing part that is capable of engaging with the lancet cap; and a trigger lever that is pressed to launch the pricking component, wherein the lancet assembly can be loaded into the injector by inserting the lancet holder into the injector through the front end opening of the injector.

When the lancet assembly (in which the lancet body is housed in the lancet holder and is secured to the lancet holder) is loaded into the injector, the lancet cap removing part can engage with the lancet cap; and when the lancet holder is inserted further while the lancet cap removing part and the lancet cap is still in engagement, the force for moving the lancet cap and the lancet body away from each other is generated so that the lancet cap is separated from the lancet body. The separated lancet cap can subsequently move in the pricking direction within the lancet holder.

In a preferred embodiment of the injector of the present invention, a spring is provided around the plunger between a flange formed around an intermediate portion of the plunger and a partition provided in an injector housing; Upon the loading of the lancet assembly into the injector, the rear end portion of the lancet body engages with the front end of the plunger so that the plunger is retracted, and thereby the spring is compressed as the plunger is retracted. In this case, the flange of the plunger can move to a position that is backward relative to a rear stepped portion of the trigger lever on which an inward force is exerted (i.e. the trigger lever is forced to move toward the inside of the injector), and thereafter the flange of the plunger can engage with the rear stepped portion while the spring is still in a compressed state. It is noted, as long as the plunger can be retracted, that the engagement between the rear end portion of the lancet body and the front end of the plunger may take place at any time in the period from the retracting of the plunger to before the pricking.

After the flange of the plunger has engaged with the rear stepped portion of the trigger lever, the front portion of the trigger lever is pressed inwardly (in the direction toward the inside of the injector). This causes the cease of the engagement between the rear stepped portion of the trigger lever and the flange so that the compressed spring exerts an expanding force to returns to its original shape. In this way, it is possible to launch the lancet body (specifically the lancet body with the tip of the pricking component exposed) forward in the pricking direction by pressing front portion of the trigger lever inwardly after the completion of the loading.

In a preferred embodiment, the injector of the present invention further comprises a pricking depth adjusting mechanism. Such pricking depth adjusting mechanism comprises a protrusion provided on an rear end of the plunger such that it protrudes outwardly from the plunger in the transverse direction thereof; and a cylindrical component with graduated stepped portions of various heights, wherein when the plunger moves forward for pricking, the protrusion of the rear end of the plunger hits the stepped portions of the cylindrical component so that the plunger is unable to move further forward. By rotating the cylindrical component about its center axis, the step portions which the protrusion hits can be switch for other step portions with different heights, and thereby the distance over which the plunger can move forward for pricking is changed. In this way, the pricking depth can be adjusted.

In a preferred embodiment, the injector of the present invention further comprises an ejector. By sliding the ejector forward, the lancet holder is pushed forward by the ejector, and thereby the lancet assembly (specifically the lancet holder in which the spent lancet is housed) can be removed from the injector.

In a third aspect, there is provided a lancet and a lancet holder that constitute the lancet assembly of the present invention. There is also provided a pricking device constituted by combining the lancet assembly with the injector. In addition, there is provided a pricking device kit in which the lancet assembly of the present invention and the injector of the present invention are used to form the pricking device.

As to the lancet assembly and the injector described above, the lancet is housed in the lancet holder such that the lancet does not protrude from the lancet holder, and the lancet cap is pressed by the lancet cap removing part of the injector. It is noted that the present invention will not necessarily be limited to the above. For example, a part of the lancet cap may protrude from the lancet holder. In this case, the lancet cap can be pushed by making the protruding part of the lancet contact with the front end portion of the injector upon loading the lancet assembly into the injector. In the following description, a lancet assembly, an injector and related components in a case where the lancet cap does not protrude from the lancet holder will be referred to as "type A", whereas a lancet assembly, an injector and related components in a case where a part of the lancet cap does protrude from the lancet holder will be referred to as "type B".

In the lancet assembly of type B, the lancet is housed in the lancet holder such that a part of the lancet cap protrudes from the lancet holder. The protruding part of the lancet cap (which corresponds to "separator protrusion" to be described later) makes contact with the front end portion of an injector for launching the pricking component, upon loading the lancet assembly into the injector for launching the pricking component by inserting the lancet holder into the injector through the front end opening of the injector. When the lancet holder is inserted further while the protruding part of the lancet cap and the front end portion of the injector is still in contact with each other, the force for moving the lancet cap and the lancet body away from each other is generated so that the lancet cap is separated from the lancet body due to the breaking of the bridging component, and thereby the tip of the pricking component is exposed while the pricking component remains situated in the lancet body. Subsequently, as the lancet holder is inserted further, the separated lancet cap is guided by opposing side faces of the lancet holder, and thereby the separated lancet cap moves to a position that is off the pricking pathway of the pricking component.

In a preferred embodiment of the lancet assembly of type B, the lancet cap comprises a pair of separator protrusions (for example, separator arms) extending in a transverse direction and in a symmetrical configuration with respect to the pricking component;

each of the opposing side faces of the lancet holder has an elongated opening as a guide;

each separator protrusion of the lancet cap extends through the elongated opening so that an edge portion of the each separator protrusion protrudes outward from the elongated opening;

as a result, when loading the lancet assembly into the injector, the edge portion of the each separator protrusion makes contact with the front end portion of the injector;

as the lancet holder is inserted further, the edge portion of the each separator protrusion is pushed forward by the front end portion of the injector while the lancet body is prevented from moving forward, and thereby the force for moving the lancet cap and the lancet body away from each other is generated so that the bridging component is broken; and as the lancet holder is inserted furthermore, the edge portion of the each separator protrusion moves forward along the elongated opening obliquely (in the forward direction deflected upward or the forward direction deflected downward) off the pricking pathway, and thereby the separated lancet cap with the separator protrusions is guided and moves to a position that is off the pricking pathway of the pricking component.

In a further preferred embodiment of the lancet assembly of type B, the each separator protrusion forward moves obliquely (in the forward direction deflected upward or the forward direction deflected downward) with respect to the pricking direction, and then the each separator protrusion moves forward in a direction parallel to the pricking pathway while being still off the pricking pathway. In this way, the edge portion of the each separator protrusion deviates from the pricking pathway.

In a further preferred embodiment of the lancet assembly of type B, the lancet body comprises a pair of stopper protrusions extending in the transverse direction and in a symmetrical configuration with respect to the pricking component. In the lancet assembly prior to pricking, the stopper protrusion functions as a stopper that fits into the elongated opening and thus prevents the lancet body from coming off the holder. On the other hand, upon pricking, the stopper protrusion does not hamper the launching of the pricking component. Furthermore, after the pricking, the stopper protrusion acts to prevent the tip of the pricking component from protruding from the pricking opening. In other words, each stopper protrusion is caused to deform inwardly toward the pricking component by the force exerted onto the each stopper protrusion upon launching the lancet body with the protruding end, whereas the each stopper protrusion returns to its original shape after the tip of the pricking component has pricked and been retracted into the lancet holder. As a result, the each stopper protrusion, upon pricking, does not contact with a stopper provided on an inner surface of the lancet holder, whereas the each stopper protrusion, after pricking, can contact with the stopper provided on the inner surface of the lancet holder, and thereby the tip of the pricking component would not protrude from the pricking opening after pricking. It is noted that, although the stopper protrusion (for example, "stop arm") fits into the elongated opening and protrude from the elongated opening, it preferably does not protrude as much as the separator protrusion does.

In a further preferred embodiment of the lancet assembly of type B, similarly to the lancet assembly of type A, the lancet holder has, on its inner wall, a guide channel for guiding the lancet body in the pricking direction, and the lancet body has a guided component that slots into the guide channel of the lancet holder. A protrusion A formed on the guided component and a protrusion B formed within the guide channel are in contact with each other so that the lancet body is attached or secured to the lancet holder. The protrusion A formed on the guided component of the lancet body is not caused to ride over the protrusion B formed within the guide channel by the force with a strength that is just capable of breaking the bridging component. However, when the lancet holder is inserted further into the injector after the lancet cap has been separated from the lancet body, the force acting on the rear end portion of the lancet body enables the protrusion A to ride over the protrusion B within the guide channel, and thereby the contact between the protrusion A and the protrusion B ceases. In other word, upon the loading of the lancet assembly into the injector, the plunger is prevented from further being retracted after the lancet cap is separated from the lancet body, so that the lancet body being in engagement with the plunger is prevented from being further inserted into the injector, and subsequently when the lancet holder is forced to move further in the direction of insertion, the contact between the protrusion A and the protrusion B ceases so that the lancet body can move along the guide channel in the pricking direction.

The injector of type B can be used in combination with the lancet assembly of type B. The injector of type B comprises substantially the same components or parts as those of the injector of type A. For example, the injector of type B comprises a plunger for launching the lancet body in the pricking direction, a trigger lever that is pressed to launch the pricking component, and a pricking depth adjusting mechanism for adjusting the depth of pricking. A difference is that the injector type B has such a configuration that an protruding part of the lancet cap is pressed forward upon loading the lancet assembly in the injector. That is, with respect to the injector of type B, the lancet holder can be inserted into the injector through an front end opening of the injector while the protruding part of the lancet cap and the front end portion of the injector are still in contact with each other, and thereby the lancet cap is separated from the lancet body, and the separated lancet cap moves forward in the lancet holder to the position that is off the pricking pathway of the pricking component.

It is preferable that the plunger provided in the injector of type B has such a configuration that it can grasp the rear end portion of the lancet body upon inserting the lancet holder further after the lancet cap has been separated from the lancet body. It is also preferable that the injector is provided with a hook part. On the hook part, an inward force is exerted so that the hook part is forced to move inwardly. The hook part can fit with the rear edge of the elongated opening from outside of the lancet holder toward the inside thereof so as to lock the lancet holder. The phrase "inward force is exerted" means that the hook part is biased so that the inward force is generated.

In a further preferred embodiment of the injector of type B, similarly to the injector of type A, a spring is provided around the plunger between a flange formed around an intermediate portion of the plunger and a partition provided in an injector housing;

upon the loading of the lancet assembly into the injector, the rear end portion of the lancet body engages with the front end portion of the plunger so that the plunger is retracted, and thereby the spring is compressed as the plunger is retracted; and when the flange of the plunger moves to a position located backward relative to the rear end portion of the trigger lever, and then the flange of the plunger can engage with the rear end portion of the trigger lever while the spring is still in a compressed state.

It will be noted that the rear end portion of the lancet body is finally grasped by the front end portion of the plunger, and that such grasping may take place at a certain point either before or after the flange of the plunger and the rear end portion of the trigger lever engage with each other.

In a further preferred embodiment, the injector of type B comprises a slider part extending backward from the front end opening of the injector. The slider part has a function of inwardly deforming one of the stopper protrusions of the lancet body upon inserting the lancet holder backward through the front end opening of the injector, and of maintaining the deformed state of the one of the stopper protrusions.

When the lancet assembly has been loaded into the injector, the other stopper protrusion is positioned inward from the front portion of the trigger lever. Therefore, the other stopper protrusion is deformed inwardly by the front portion of the trigger lever when the trigger lever is pressed inwardly upon pricking. Specifically, when the front portion of the trigger lever is pressed inwardly upon pricking, the other stopper protrusion is deformed similarly to the one stopper protrusion, and at the same time the engagement of the rear end of the trigger lever and the flange of the plunger is released. As a result, the lancet body (namely, the lancet body with the tip of the pricking component exposed) is launched forward due to the spring force (attributable to an expansion of the compressed spring). In other word, the injector of type B is characterized in that the engagement of the rear end of the trigger lever and the flange of the plunger ceases at the same time as or after the other stopper protrusion is deformed by pressing the trigger lever.

The present invention provides the lancet and the lancet holder that constitute the lancet assembly of type B, similarly to the case of type A. The present invention also provides the pricking device constituted by combining the lancet assembly of type B and the injector of type B.

The lancet assembly of the present invention is combined with the injector of the present invention so as to provide the pricking device. In this case, the pricking device can be made ready for pricking only by inserting the lancet holder into the injector. Thus it is made possible to launch (or cock) the lancet without needing to remove the lancet cap by hand (or by fingers). Furthermore, the pricking device of the present invention makes it possible to discharge the used lancet holder (in which the used pricking component whose tip is exposed is contained) more safely from the injector, by simply operating the ejector (namely just by sliding the ejector) after pricking. As a result, the pricking operation can be completed through substantially three steps as follows: (i) step of loading the lancet assembly into the injector; (ii) step of pricking; and (iii) step of discharging of the lancet assembly by using the ejector.

The lancet assembly of the present invention (in particular, the lancet assembly of type A) makes it possible to keep the pricking depth substantially constant, since the pricking opening of the lancet holder is small so that the pricking depth is less likely to be affected by the pressing force applied upon pricking.

Furthermore, in the lancet assembly of type A according to the present invention, the lancet holder for housing the lancet body has no opening except for the opening end and the pricking opening. Due to this, the lancet is housed in the lancet holder such that the lancet does not protrude from the lancet holder. In other words, there is provided no openings in the side faces of the lancet holder, and thus the lancet is in a more hygienic state since the lancet is isolated to some extent from its surrounding environment.

BRIEF DESCRIPTION OF THE DRAWINGS

FIG. 6 is cut away. FIG. 8(a) shows that the lancet body of type A is secured to the lancet holder of type A, whereas FIG. 8(b) shows that the lancet body of type A is no longer secured to the lancet holder of type A.

FIG. 11(a) shows a plunger. FIG. 11(b) shows a lancet cap removing part. FIG. 11(c) shows a trigger lever. FIG. 11(d) shows an ejector.

FIG. 12(a) and FIG. 12(b) respectively show half members that constitute the housing of type A.

FIG. 13(b) also shows some components related to a pricking depth adjusting mechanism.

FIG. 24(a) shows the state around the time when the accommodation of the second wing parts 159 into the bow-shaped groove 206d is commenced. FIG. 24(b) shows the state of the after-loading wherein the second wing parts 159 lie in the bow-shaped groove 206d.

DETAILED DESCRIPTION OF THE INVENTION

Figure 1A:
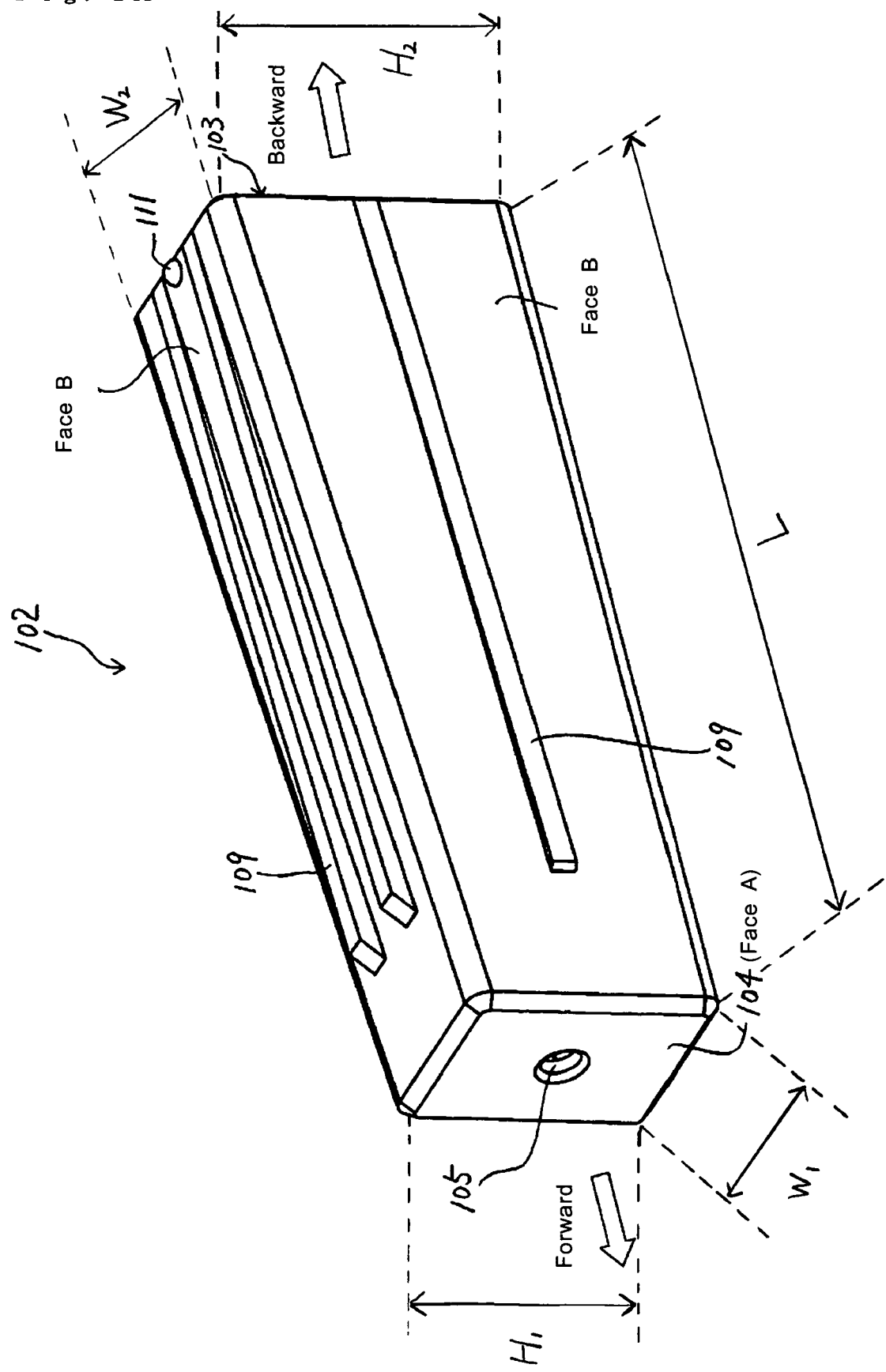
FIG. 1A is a schematic perspective view of lancet holder of type A.

With reference to the accompanying drawings, the lancet assembly of the present invention as well as the lancet and the lancet holder that constitute the lancet assembly will be described in detail. The injector used in combination with the lancet assembly also will be described in detail. In conjunction with the description of the lancet assembly, the lancet, the lancet holder and the injector, the pricking device and the pricking device kit comprising the lancet assembly and the injector will also be described. Hereinafter, there will be provided a description of the lancet assembly, followed by a description of the pricking device together with a description of the injector. As described previously, "type A" will be described with respect to an embodiment wherein the lancet is housed in the lancet holder with no protrusion of the lancet from the lancet holder and the lancet cap is pushed by the lancet cap removing part of the injector, whereas "type B" will be described with respect to an embodiment wherein the lancet is housed in the lancet holder with the lancet protruding from the lancet holder, and the lancet cap is pushed by the front end portion of the injector while the protruded portion of the lancet cap and the front end portion of the injector are in contact with each other upon loading the lancet assembly into the injector. Description will be given chiefly on the lancet assembly and the injector of type A, followed by the description of the lancet assembly and the injector of type B. Description without a particular account or a specific matter of either type should be regarded as applying to both type A and type B.

Throughout the claims, the description and the abstract, the word "forward" means the pricking direction in which the lancet moves for pricking (namely the direction in which the pricking component moves for pricking), and the word "backward" means the direction opposite to "forward". These directions and the transverse direction are indicated in the drawings. It should be noted that "pricking direction" corresponds to a direction from the opening end of the lancet holder toward the pricking opening of the lancet holder.

[Lancet Assembly and Injector of Type A]

Figure 2A:
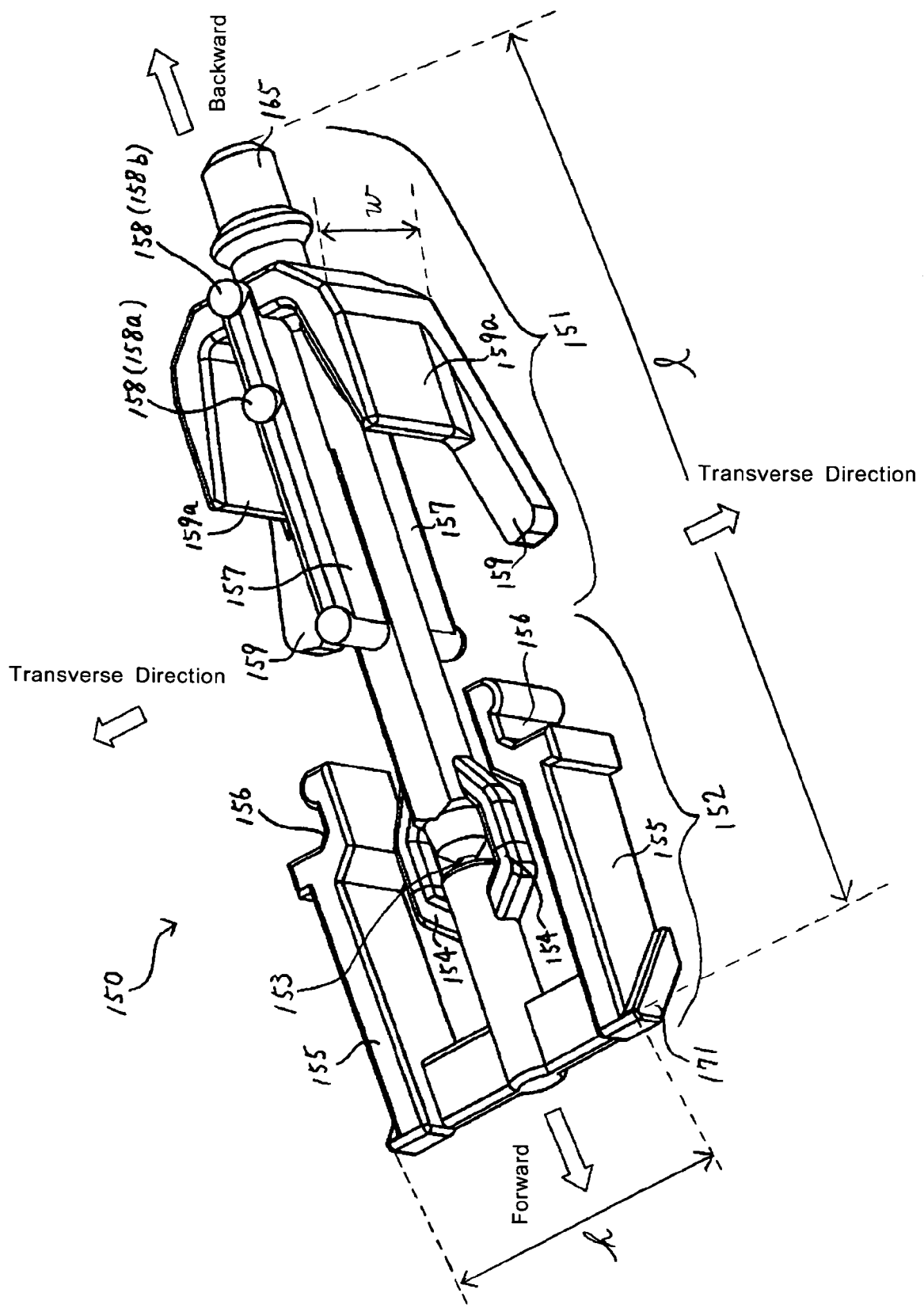
FIG. 2A is a schematic perspective view of lancet of type A.
Figure 3:
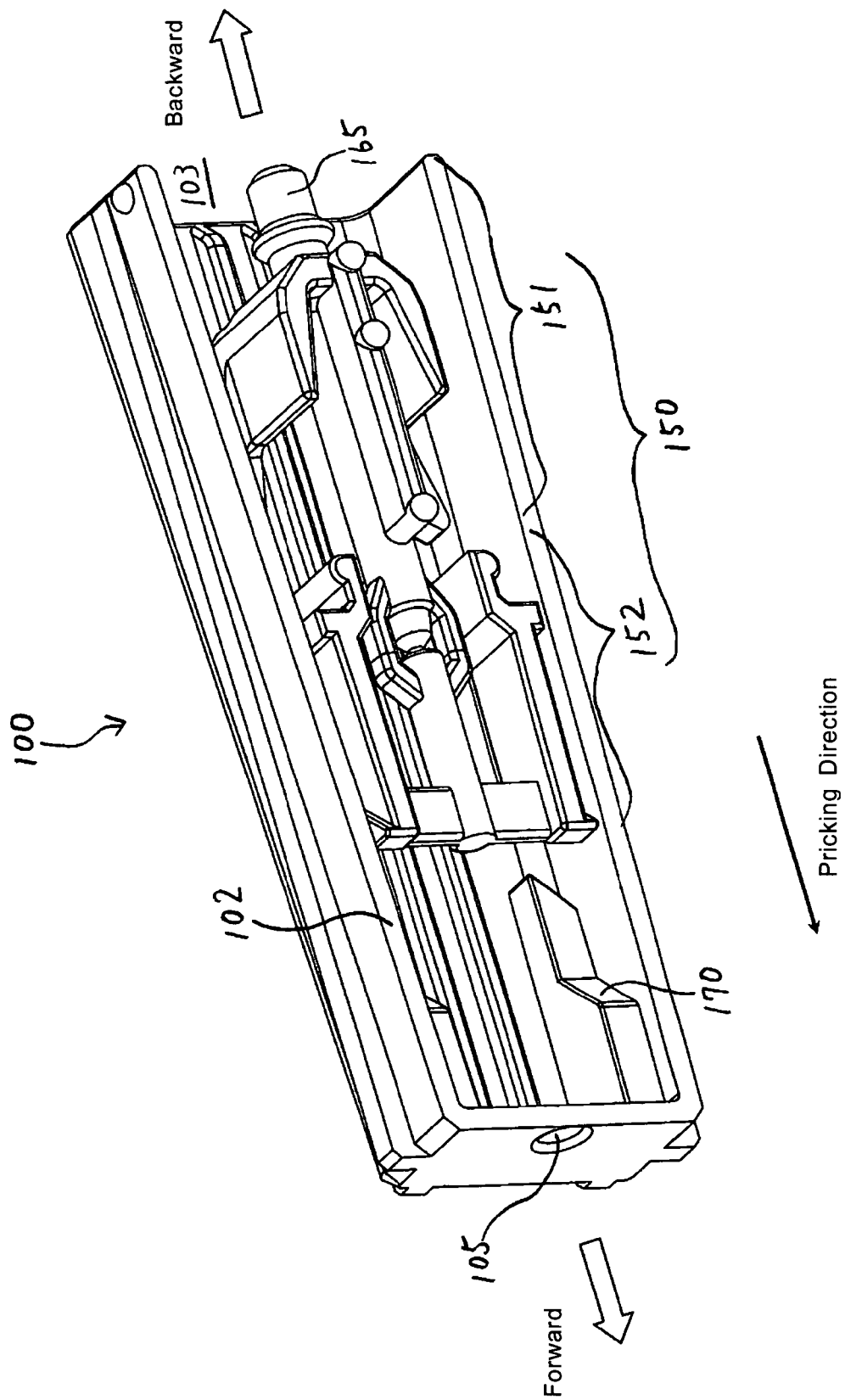
FIG. 3 is a schematic perspective view of the lancet assembly of type A wherein the lancet holder of type A has been cut away in half along the longitudinal direction thereof.

The lancet assembly of type A according to the present invention is used in such a state that a lancet 150 shown in FIG. 2A is secured to a lancet holder 102 shown in FIG. 1A. FIG. 3 schematically shows a lancet assembly 100 of type A. It will be noted that, for the ease of understanding the structure of the lancet assembly 100, the lancet holder 102 is shown in FIG. 3 with a half thereof cut away along the longitudinal direction.

Figure 4A:
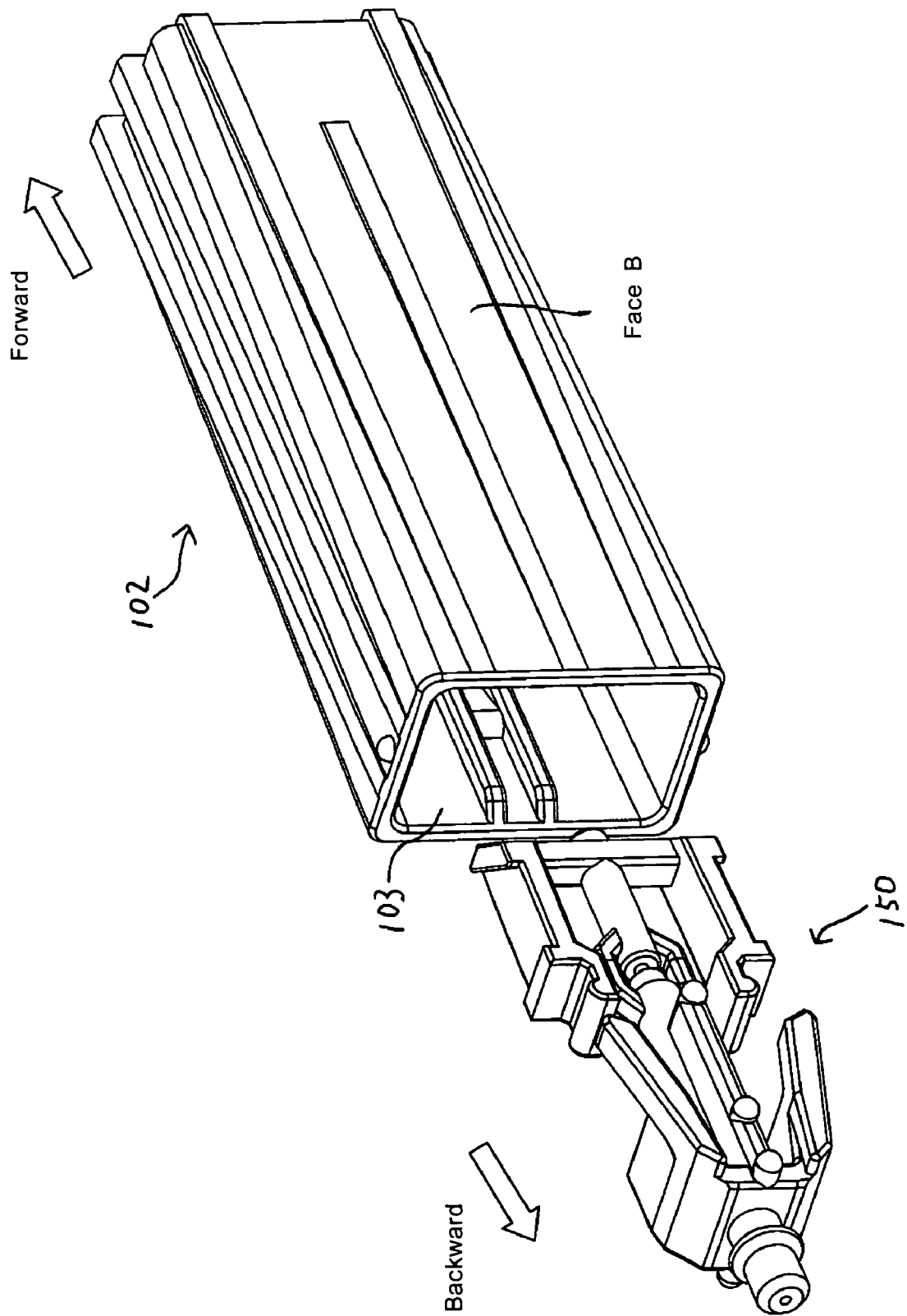
FIG. 4A is a schematic perspective view of the state immediately before inserting the lancet of type A into the lancet holder.
Figure 4B:
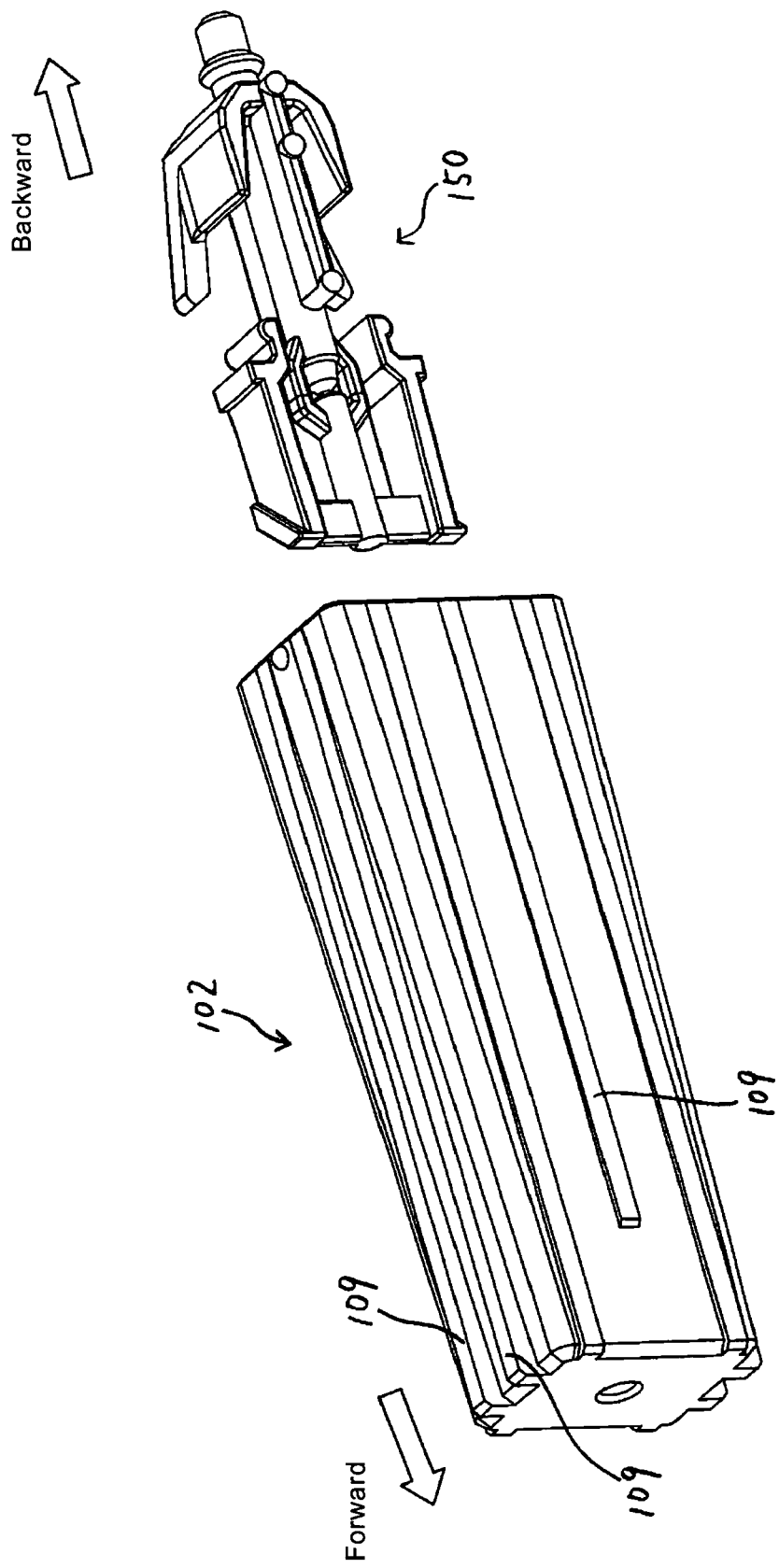
FIG. 4B is a schematic perspective view of the state immediately before inserting the lancet of type A into the lancet holder, viewed in a direction different from that of FIG. 4A.
Figure 4C:
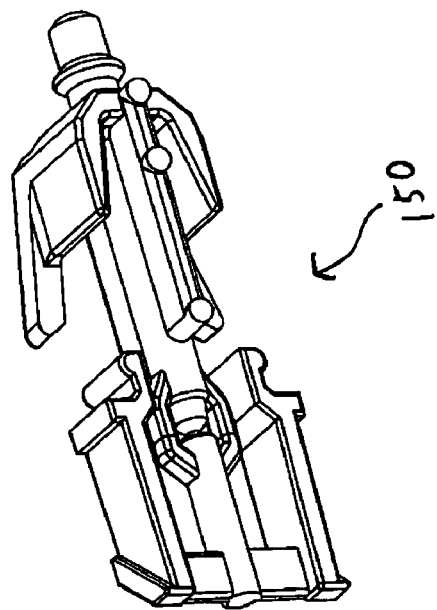
FIG. 4C is a schematic perspective view of the same state as that of FIG. 4B, wherein the lancet holder of type A has been cut away in half along the longitudinal direction thereof.
Figure 4C:
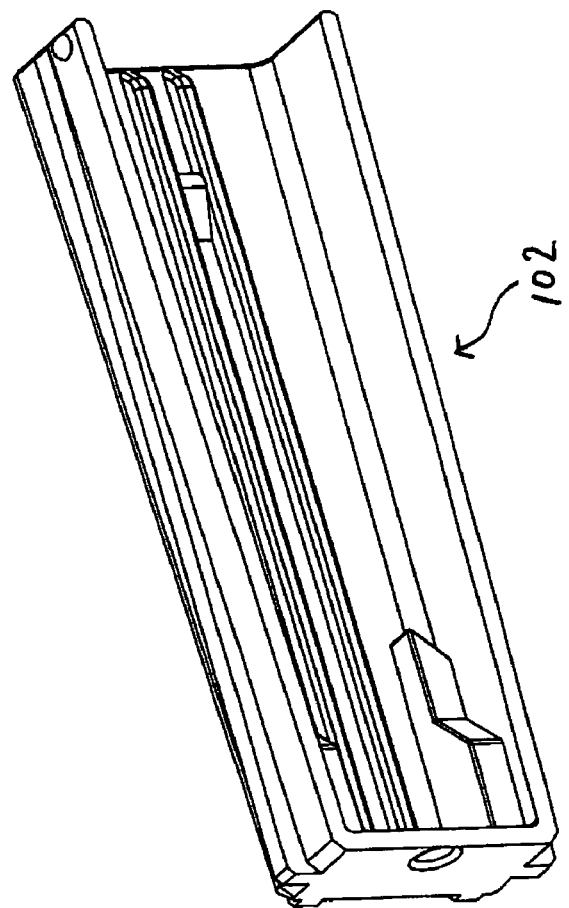
Figure 4D:
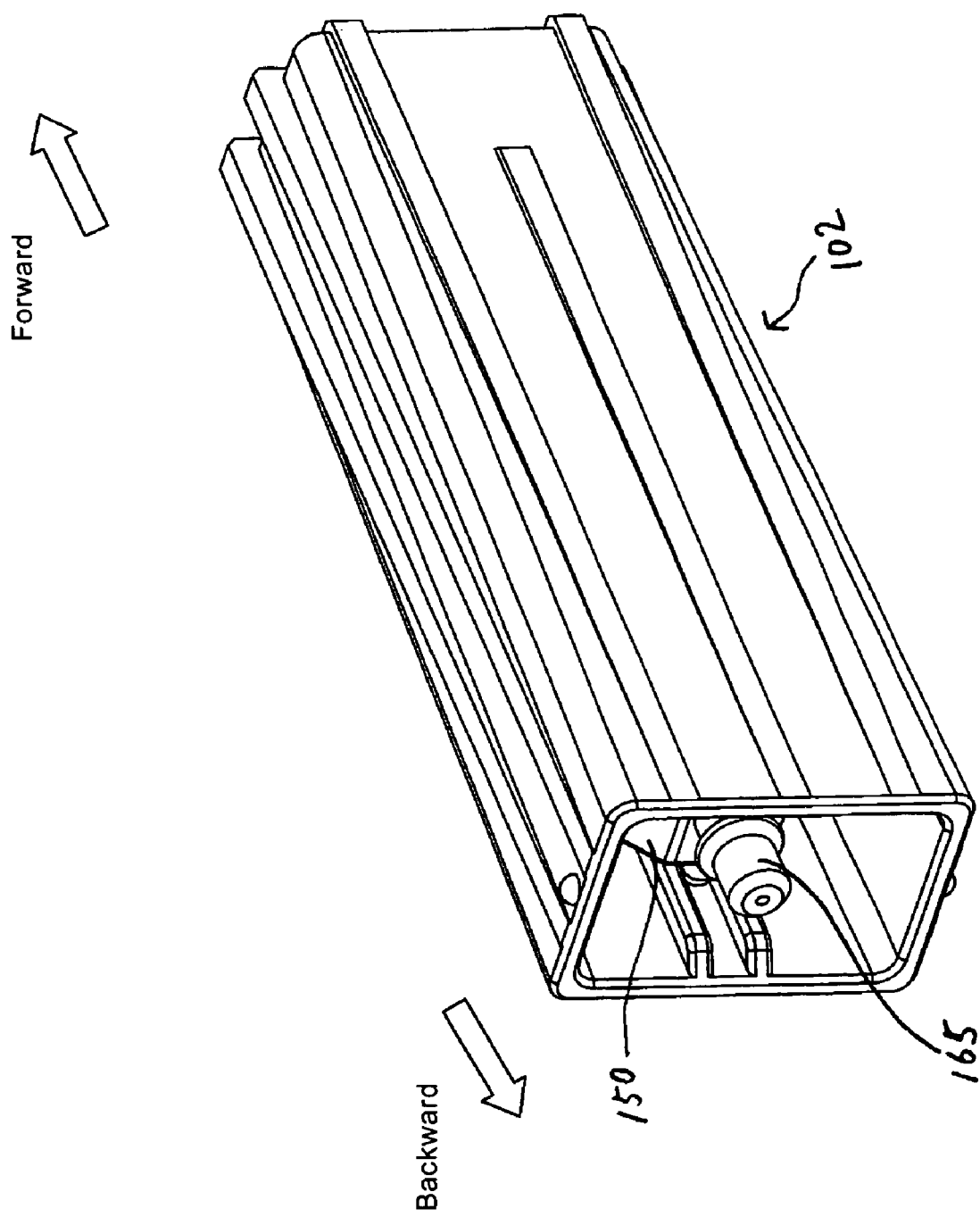
FIG. 4D is a schematic perspective view showing the state where the lancet of type A has been inserted into the lancet holder of type A, viewed from behind the lancet holder.

The lancet holder 102 of type A has, as a whole, a shape of square box or square tube as shown in FIG. 1A, for example. The lancet holder 102 has small dimensions. For example, length-height-width (L, $H_1$, $H_2$, $W_1$, $W_2$) shown in FIG. 1A may be as follows: "L" is in the range from 27.4 to 36.6 mm (for example, 29.9 mm), "$H_1$" is in the range from 6.9 to 10.4 mm (for example, 9.4 mm), "$H_2$" is in the range from 8.6 to 12.4 mm (for example, 11.1 mm), "$W_1$" is in the range from 4.2 to 7.9 mm (for example, 6.7 mm) and "$W_2$" is in the range from 4.7 to 8.5 mm (for example, 7.2 mm). However, the shape of the lancet holder 102 is not limited to the square box or square tube, and may be a cylinder. The drawings show two embodiments of the lancet holder 102 as follows: one is the embodiment in which a continuous protrusion 109 formed on the external surface of the lancet holder 102 does not terminated at the end of the holder as shown in FIG. 1A; and the other is the embodiment in which the continuous protrusion 109 is terminated at the end of the holder as shown in FIG. 4B. It is, however, noted that both embodiments represent substantially the same lancet holder 102 ("continuous protrusion 109" will be described in detail later). The lancet holder 102 may be formed of any kind of resin material which is used for lancets in general. The lancet holder 102 has an opening end 103 (most clearly shown in FIG. 4A being a rear view of the lancet holder 102) and a pricking opening 105 provided in a face 104 opposed to "opening end 103". That is, the lancet holder 102 has the openings (i.e. the opening end 103 and the pricking opening 105) only on each of its end faces (i.e. face A and the face opposed to the face A as indicated in FIG. 1A), and has no openings on its side faces (i.e. face B as indicated in FIG. 1A and FIG. 4A). The pricking opening 105 is a portion applied to the region (e.g. finger) to be pricked. The lancet assembly 100 of the present invention is assembled by inserting the lancet 150 through the opening end 103 into the lancet holder 102, and then securing the lancet 150 to the lancet holder 102. FIGS. 4A to 4D schematically show the states of the assembling to provide the lancet assembly 100 of type A. FIG. 4A shows the state immediately before the lancet 150 is inserted into the lancet holder 102. FIG. 4B shows the state of FIG. 4A viewed in a different direction from that of FIG. 4A. FIG. 4C shows the lancet holder 102 of FIG. 4B with one half thereof being cut away. FIG. 4D shows that the lancet 150 completely has been inserted into the lancet holder 102, viewed from the rear thereof.

Figure 5:
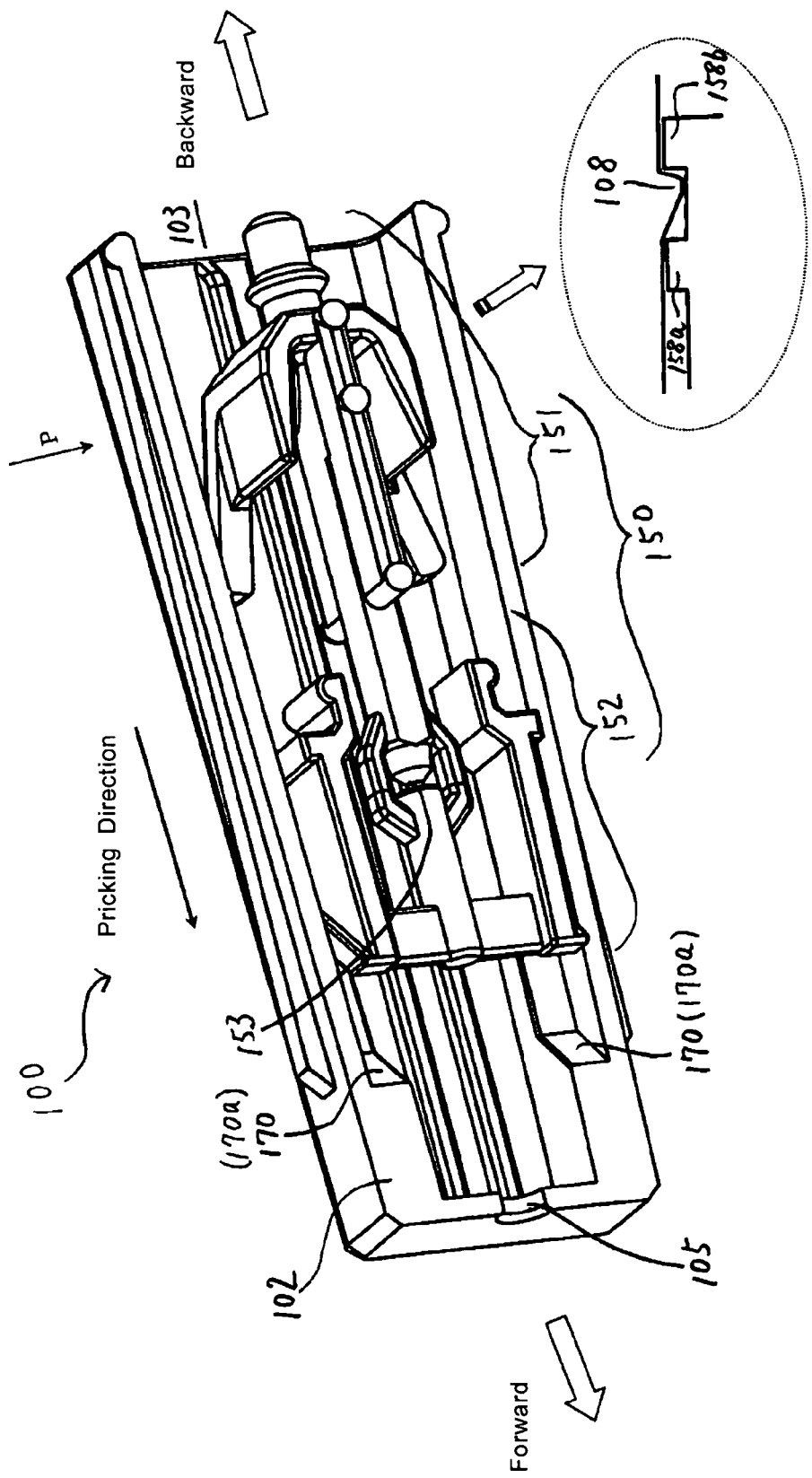
FIG. 5 is a schematic perspective view of the lancet assembly of type A, showing the state before the lancet cap of type A is separated. The enclosure by dashed line schematically shows that protrusions A (158a, 158b) and protrusion B (108) are in contact with each other, viewed in direction P.
Figure 6:
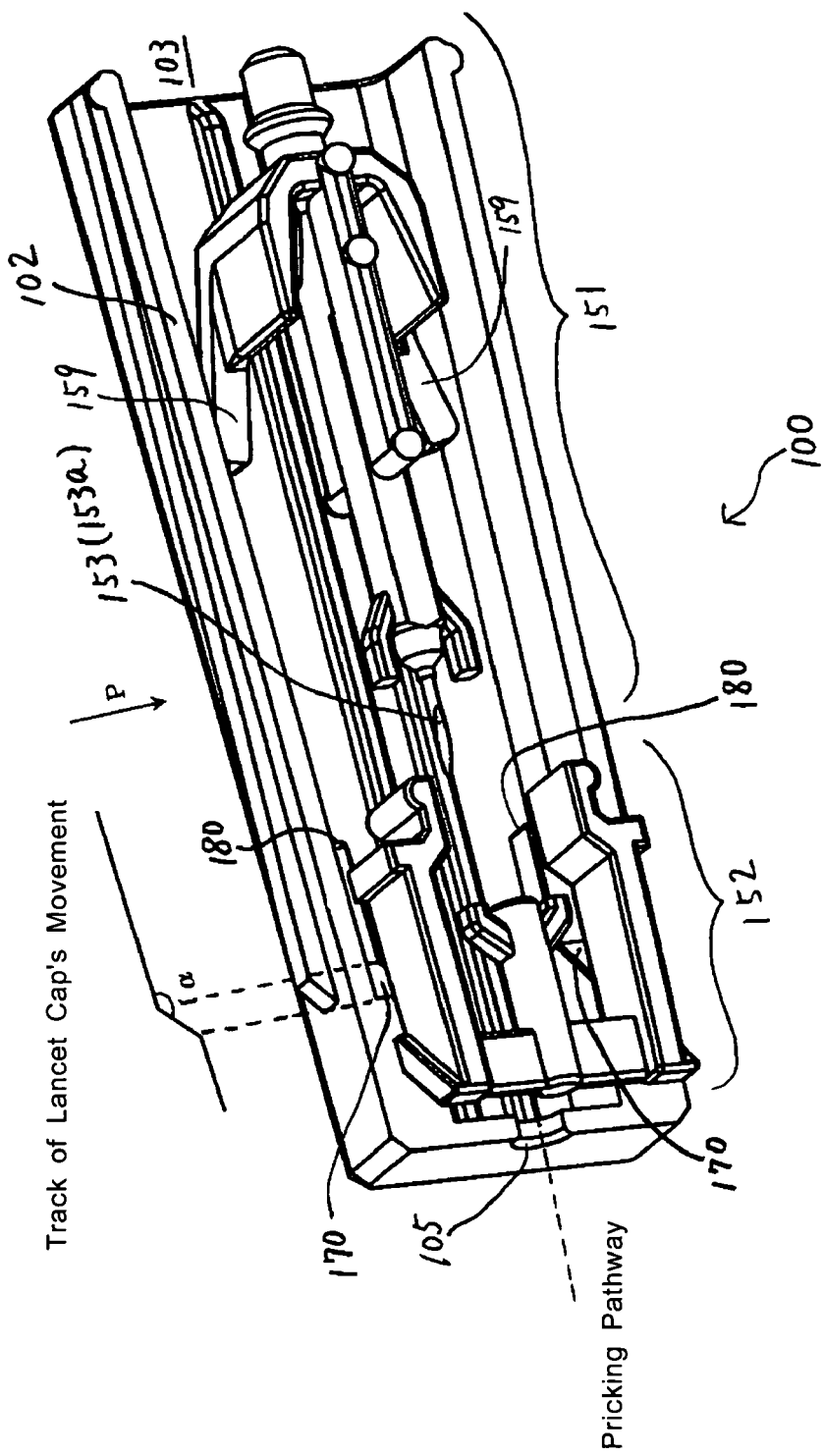
FIG. 6 is a schematic perspective view of the lancet assembly of type A, showing that the separated lancet cap has moved to a position off from the pricking pathway of the pricking component.
Figure 7:
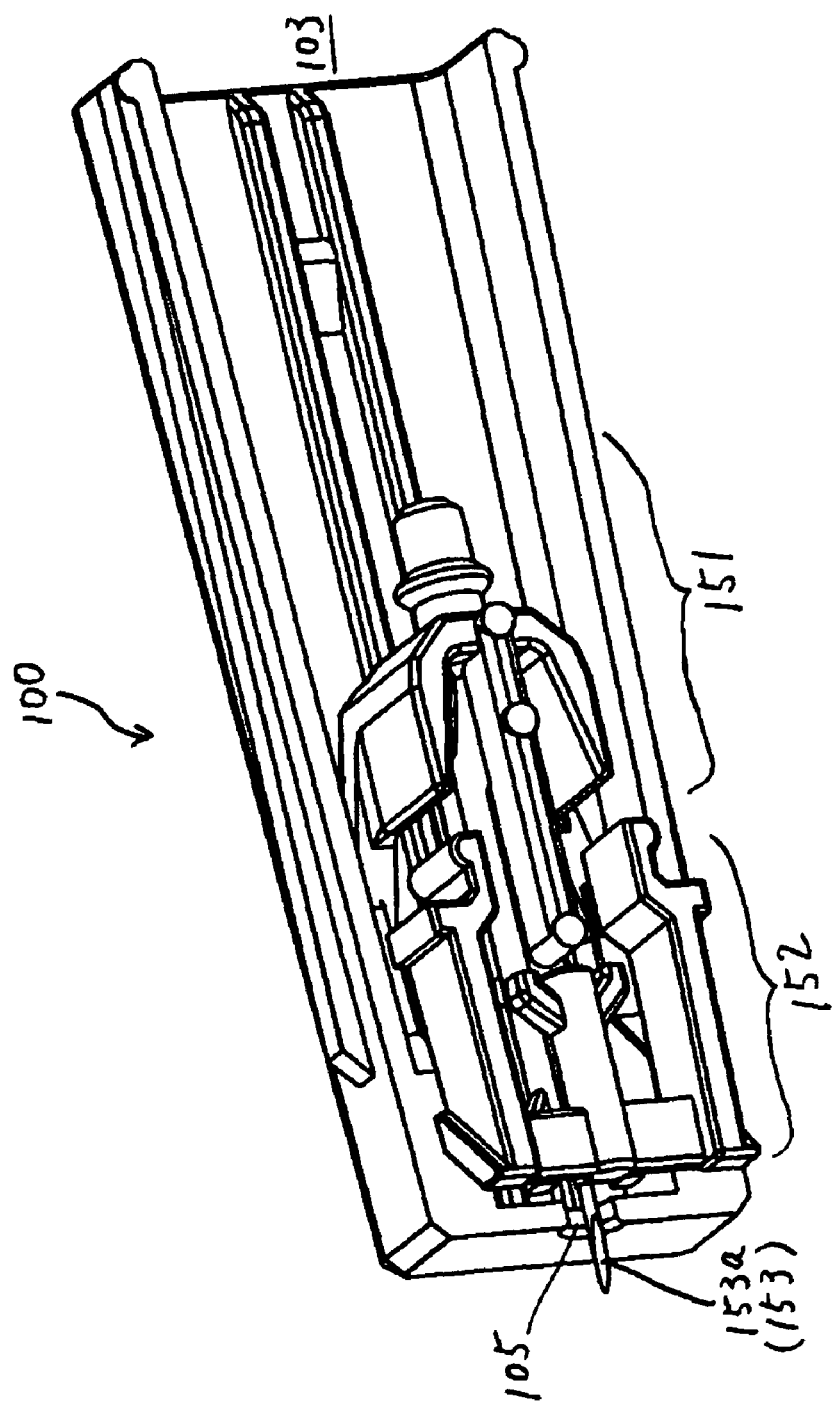
FIG. 7 is a schematic perspective view of the lancet assembly of type A upon pricking, showing that the tip of the pricking component is protruding from the pricking opening of the lancet holder.
Figure 9A:
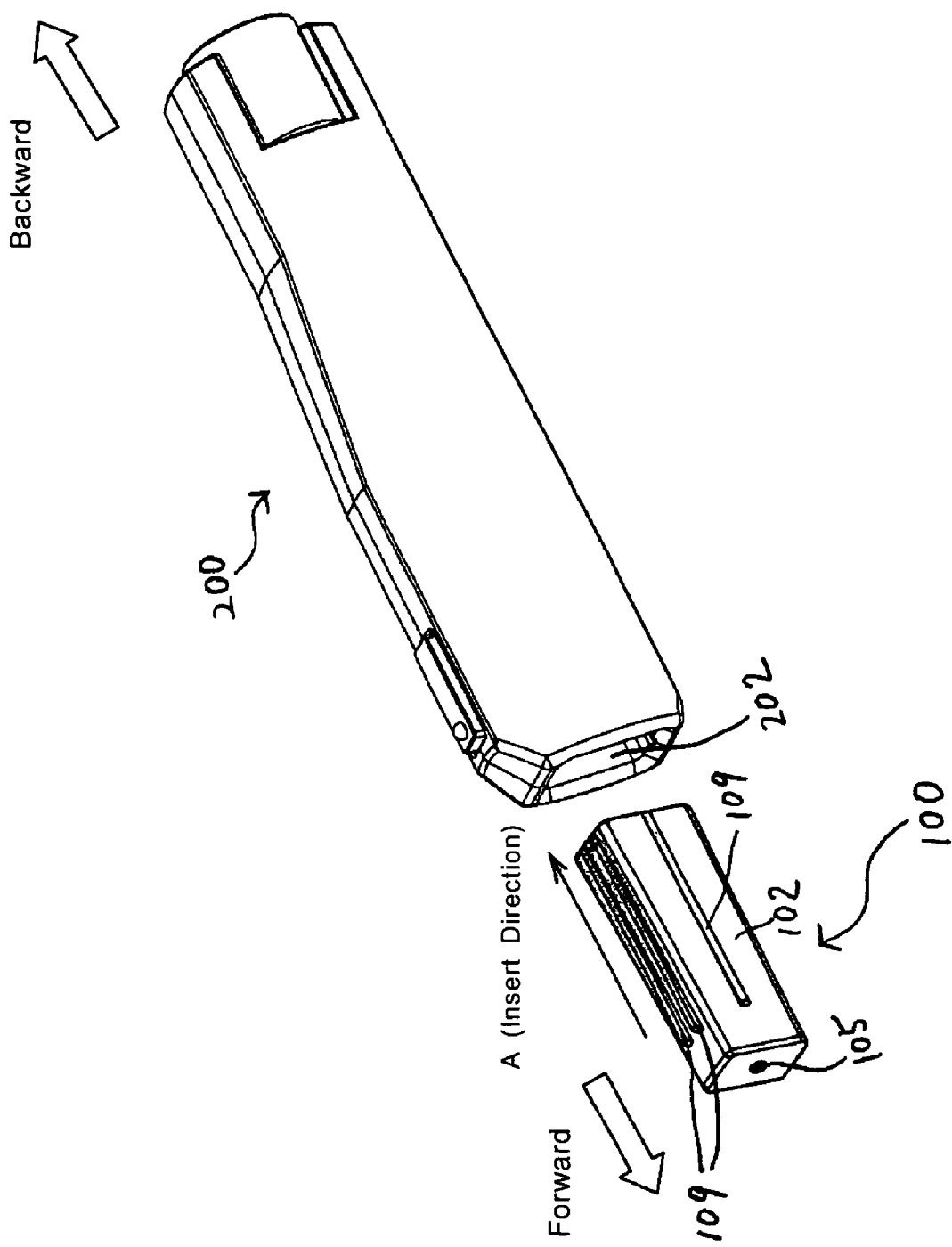
FIG. 9A is a schematic perspective view of the state immediately before the lancet assembly of type A is loaded into the injector of type A.

Use of the lancet assembly 100 of type A will now be described. In use of the lancet assembly 100, a lancet cap removing part (such part is provided in an injector 200 for launching the pricking component, and denoted with reference numeral 206 in FIG. 10B and FIG. 11(b) is inserted into the lancet holder 102 through the opening end 103 of the lancet holder 102. When the lancet assembly 100 is loaded (i.e. charged) in the injector, the lancet holder 102 is inserted through the front end opening 202 of the injector 200 in such an orientation that the pricking opening 105 faces forward and the opening end 103 faces backward as shown in FIG. 9A. By inserting the lancet holder 102 into the injector 200, the lancet cap removing part 206 can enter the lancet holder 102 through the opening end 103 of the lancet holder 102 (see FIG. 14(a) for example). As will be understood from FIGS. 5 to 7 showing that the state of the lancet assembly 100 varies with time, a pricking direction (in which the pricking component 153 or the lancet body 151 moves for pricking) corresponds to a direction from the opening end 103 to the pricking opening 105. FIG. 5 shows the state of the lancet assembly 100 prior to pricking. FIG. 6 shows the state where the separated lancet cap 152 has moved to the position that is off the pricking pathway. FIG. 7 shows the state where the tip 153a of the pricking component 153 is protruding from the pricking opening 105 after the pricking component 153 (namely the lancet body 151 with the tip 153a of the pricking component 153 exposed) has been launched.

As previously mentioned, the pricking opening 105 of the lancet holder 102 is applied to the region (e.g. a finger tip) to be pricked upon pricking. It should be noted that the pricking opening 105 of the lancet assembly 100 of type A according to the present invention is formed with a small size so that the pricking depth is kept constant, regardless of the strength of the force with which the lancet holder 102 is applied to the region (e.g. finger tip) to be pricked. Small size of the pricking opening 105 makes it less likely that a part of the finger to which the pricking opening 105 is applied swells into the lancet holder 102, even if the lancet holder is pressed strongly. This makes it possible to keep the depth of pricking substantially constant, virtually without the influence of the pressing force. For example, diameter of the pricking opening 105 is preferably from 0.5 to 2.0 mm, and more preferably from 1.0 to 1.5 mm. The term "diameter" is used with respect to the pricking opening having a circular shape. However, shape of the pricking opening 105 is not limited to the circle. In a case where the pricking opening has a shape other than the circle, it is preferable that the pricking opening 105 has an equivalent diameter of preferably from 0.5 to 2.0 mm, and more preferably from 1.0 to 1.5 mm. The term "equivalent diameter" used herein means the diameter of a circle having the same area as that of the intended pricking opening (in this case "area" is the area of the pricking opening in a plane perpendicular to the pricking direction).

Figure 1B:
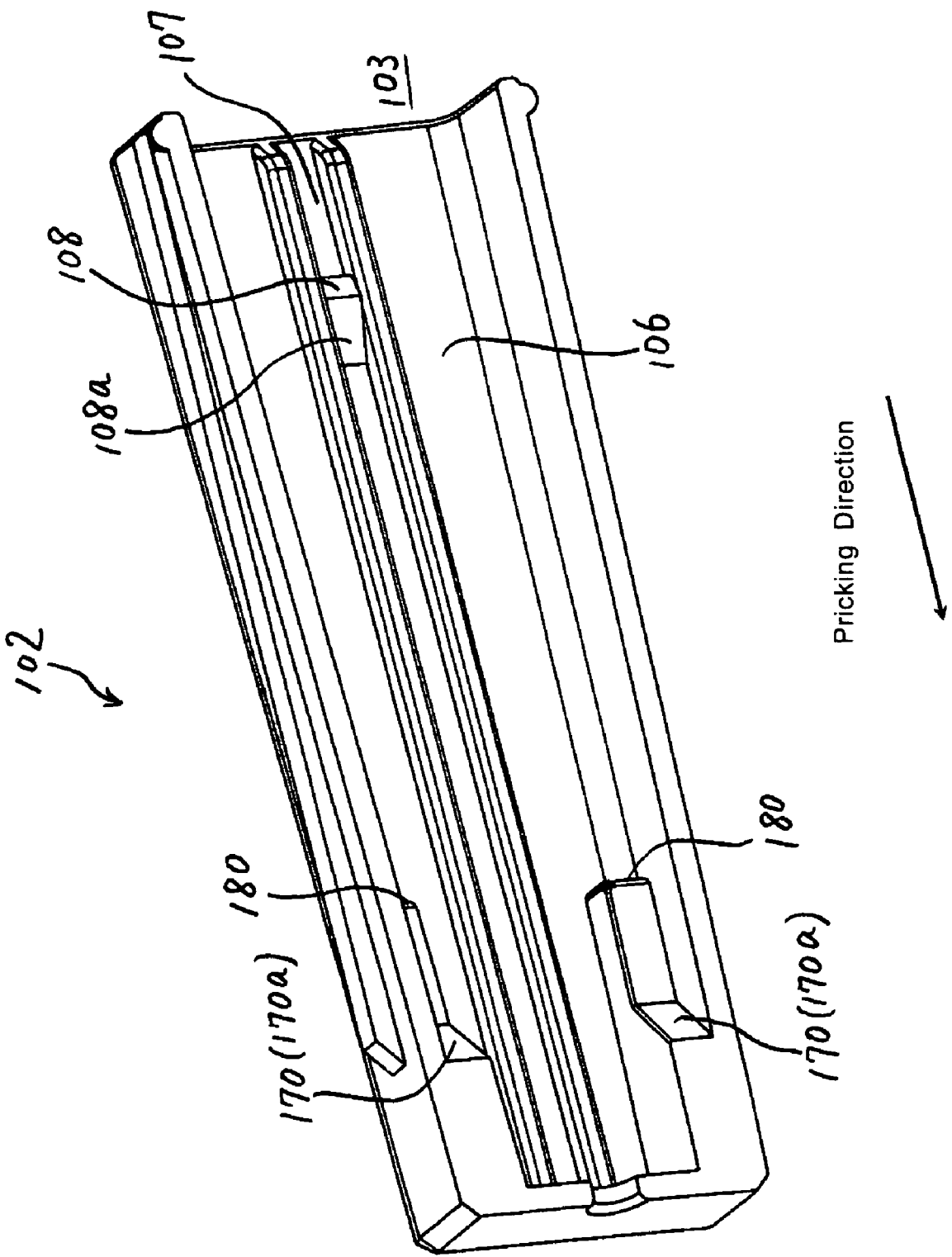
FIG. 1B is a schematic perspective view of the lancet holder of type A, cut away in half along the longitudinal direction of the lancet holder.

FIG. 1B shows the lancet holder 102 of type A as cut away in half along the longitudinal direction to help understand the internal structure of the lancet holder. The lancet holder 102 has a guide 107, preferably a guide channel 107 (for example, two rails shown in the drawings). The guide or guide channel 107 serves to guide the lancet body 151 of the lancet 150 in the pricking direction ("lancet body" is shown in FIG. 2A, for example). The guide or guide channel 107 is provided on each of the opposing inner walls 106 of the lancet holder 102 (the inner wall in this case is ones that are opposed to each other in the direction perpendicular to the direction in which the opening end 103 and the pricking opening 105 are opposed to each other). While on the other hand, the lancet body 151 has a pair of guided components 157 capable of slotting into the guide channel 107, as shown in FIG. 2A (only one of the pair of the guided components 157 is shown in FIG. 2A). When one of the pair of guided components 157 slots into the guide channel 107 of the lancet holder 102, the lancet body 151 can move in the pricking direction upon the pricking. As will be described in detail later, a protrusion B 108 (see FIG. 1B) is formed within the guide channel 107 of the lancet holder 102 (at a position located between the two rails and near the opening end 103 of the lancet holder 102), whereas a protrusion A (reference numeral 158 (158a, 158b) in FIG. 2A) is formed on the guided component 157 of the lancet body 151. The lancet body 151 can be secured so as not to move within the lancet holder 102 by bringing the protrusions A and B into contact with each other (such a secured state is most clearly shown in FIG. 8(a)).

Figure 2B:
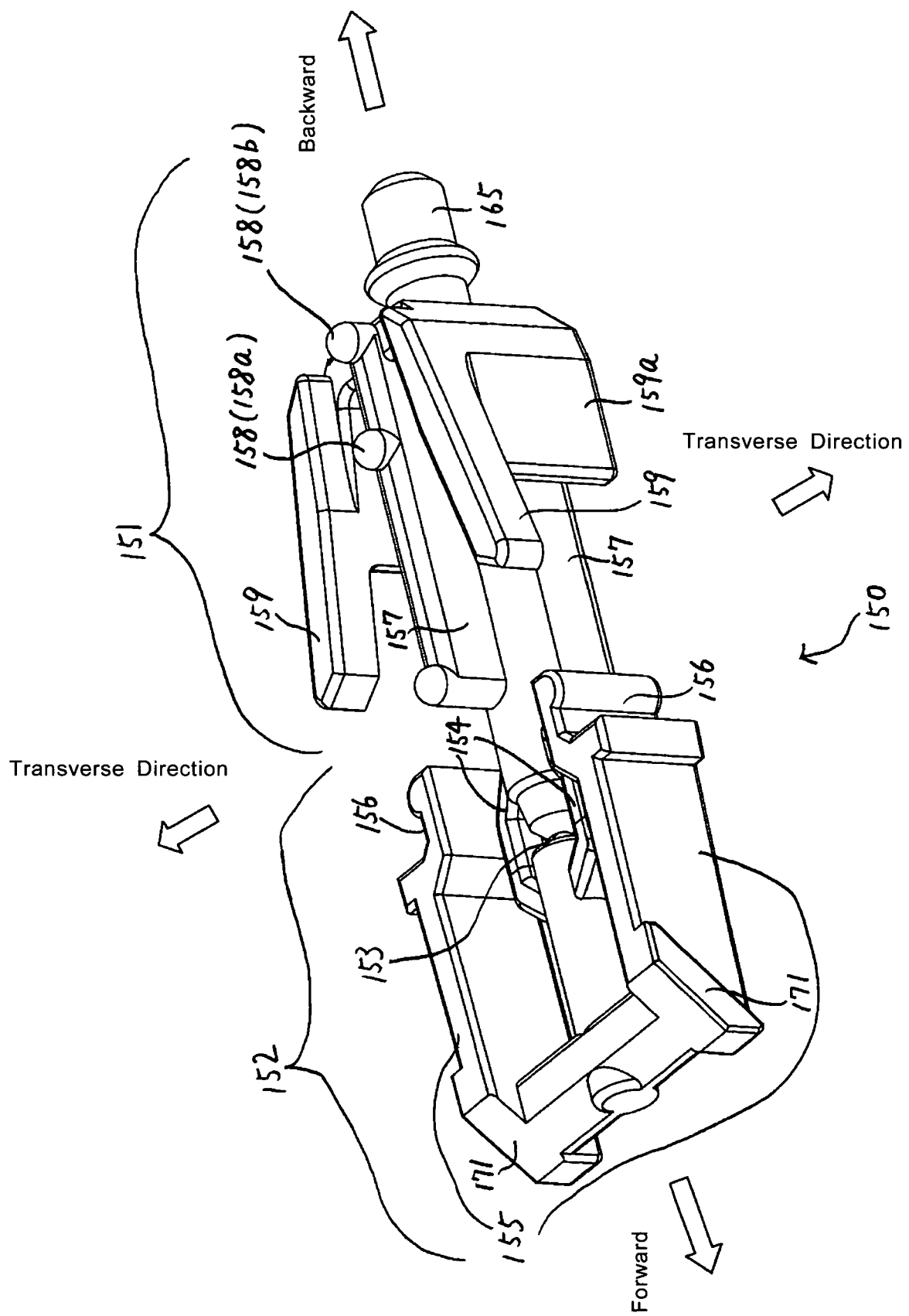
FIG. 2B is a schematic perspective view of the lancet of type A, viewed sideways in a direction different from that of FIG. 2A.
Figure 2C:
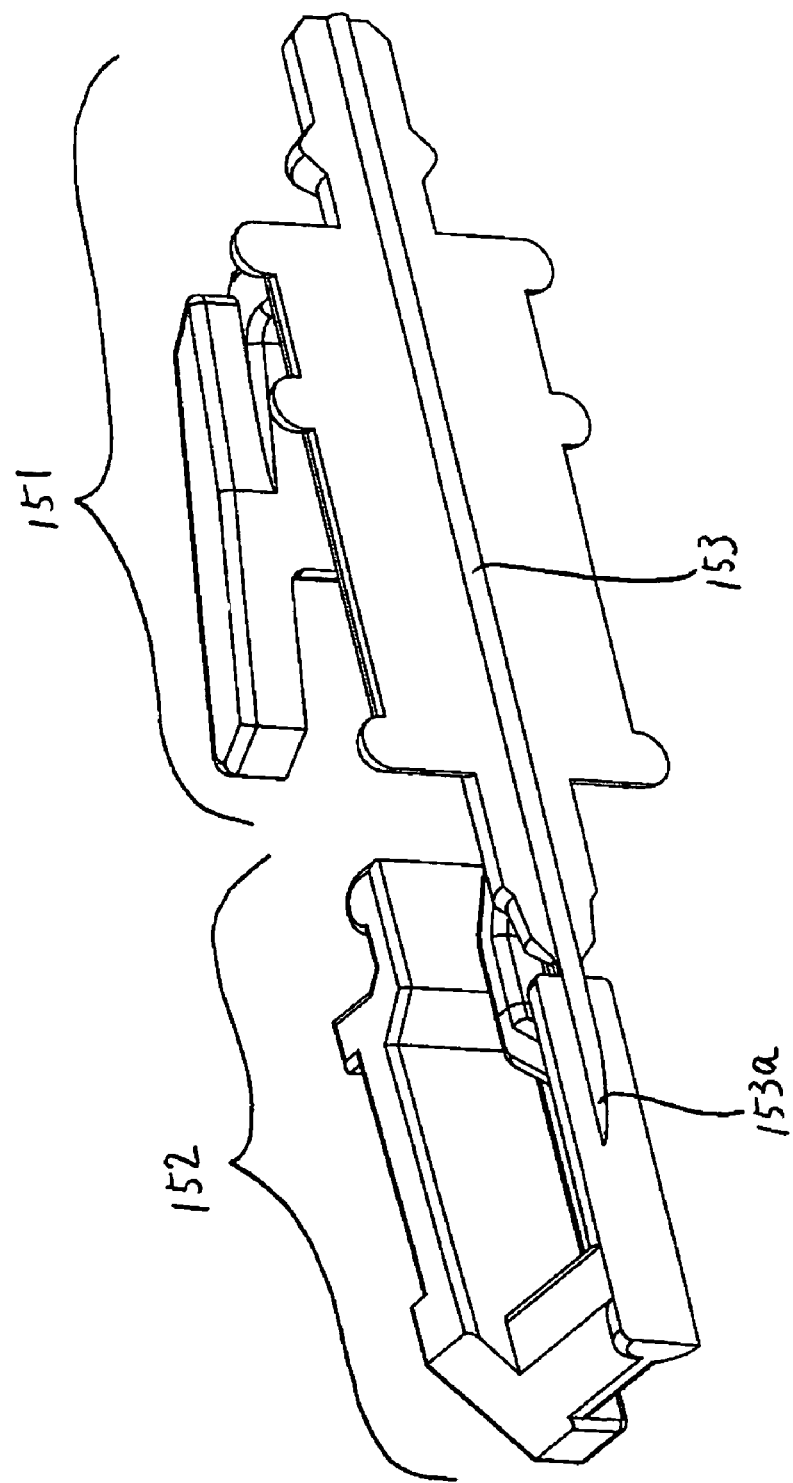
FIG. 2C is a schematic perspective view of the lancet of type A, cut away in half along the longitudinal direction of the lancet.

The perspective view of the lancet 150 of type A is shown in FIG. 2A and FIG. 2B. FIG. 2A and FIG. 2B respectively show the lancet 150 as viewed sideways in different directions. Similarly to the lancet holder 102, the lancet 150 is also small. For example, the dimensions of the lancet 150 (l, h, w) shown in FIG. 2A may be as follows: "l" is in the range from 18.3 to 25.5 mm (for example, 20.8 mm), "h" is in the range from 5.5 to 8.6 mm (for example, 8.0 mm), and "w" is in the range from 1.8 to 5.3 mm (for example, 4.3 mm). The lancet 150 comprises the lancet body 151, the lancet cap 152 and the pricking component 153 as shown in the drawings. The pricking component 153 is a metal needle, for example. As shown in FIG. 2C, the pricking component 153 is situated in both of the lancet body 151 and the lancet cap 152 made of resin wherein the tip 153a of the pricking component 153 is covered with the lancet cap 152. Since the pricking component 153 is situated within the lancet body 151 and the lancet cap 152, only a part of the pricking component 153 is shown in FIG. 2A and FIG. 2B. As shown in FIG. 2A and FIG. 2B, the lancet cap 152 and the lancet body 151 are integrally connected via the bridging component 154. The lancet 150 can be formed of resin (such as polyethylene or polypropylene) by inserting the pricking component 153 into a die, in a so-called insert molding process. In this case, the bridging component 154 can be formed upon carrying out the insert molding process. Accordingly, the bridging component 154 can be formed of the same resin as that of the lancet cap 152 and the lancet body 151. As shown in FIG. 2A and FIG. 2B, the bridging component 154 may be a rod-like component with small diameter. In this case, it is preferable that the rod-like component is provided so as to bridge between the lancet cap 152 and the lancet body 151. The bridging component 154 may have a notch (for example, a V-shaped notch) so that the bridging component 154 can be easily broken.

Figure 15A:
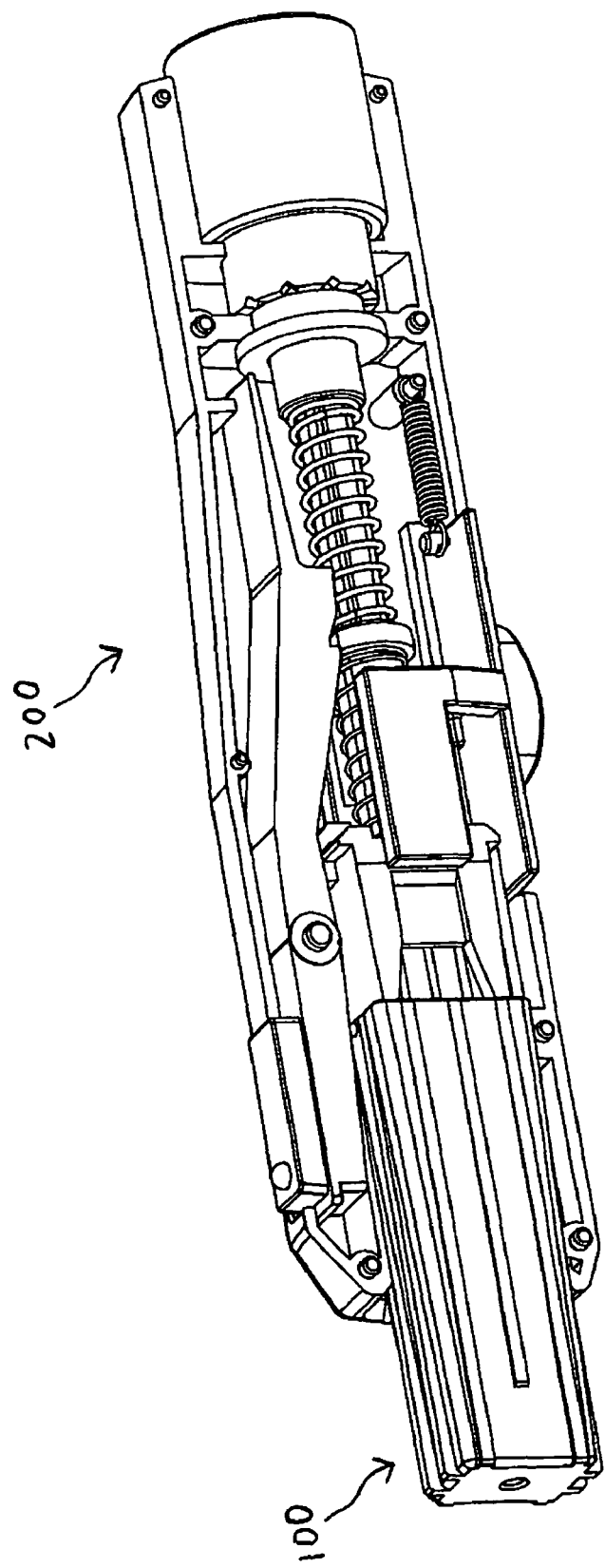
FIG. 15(a) is a schematic perspective view (type A) of the state where the lancet assembly is being inserted into the injector.
Figure 15B:
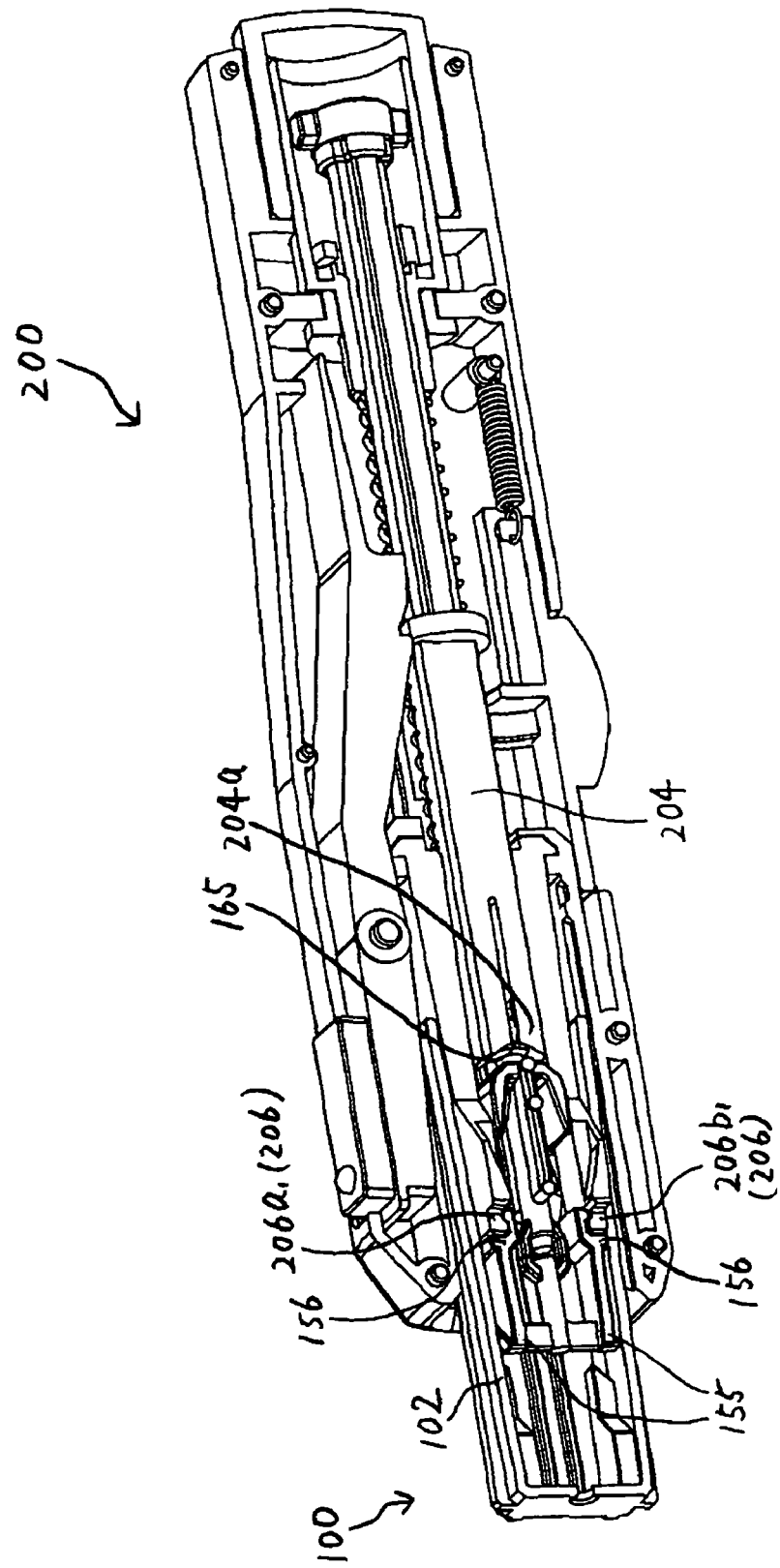
FIG. 15(b) is a schematic perspective view (type A) of the state where the lancet assembly is being inserted into the injector, and the lancet cap and the lancet removing part are in engagement with each other.

The lancet cap 152 of type A preferably has a pair of first wing parts 155. As shown in FIG. 2A and FIG. 2B, the pair of first wing parts 155 firstly extends in the transverse direction of the pricking component 153 and then extends toward the rear of the pricking component 153 in substantially symmetrical configuration with respect to the pricking component 153 (i.e. in a symmetrical configuration with respect to the longitudinal axis of the lancet 150). More preferably, each of the first wing parts 155 has, at the edge thereof, an engagement portion 156 for engaging with the end of the lancet cap removing part 206 in a complementary relationship. As seen from the drawings, the pair of first wing parts 155 has a substantially C-letter shape as a whole. Consequently, the lancet cap 152 makes it possible to engage with a lancet cap removing part 206. When the lancet cap removing part 206 enters the lancet holder 102 upon loading the lancet assembly 100 into the injector 200 (see FIG. 15(a)), the lancet cap removing part 206 and the lancet cap 152 engage with each other. The engagement between the engagement portion 156 of the lancet cap 152 and lancet cap removing part 206 is shown in FIG. 15(b), for example.

The lancet body 151 has the pair of guided components 157 capable of slotting into the guide channel 107 of the lancet holder 102, as described previously. As shown in FIG. 2A and FIG. 2B, the pair of guided components 157 is preferably a pair of plate-like portions extending toward the outside in a symmetrical configuration with respect to the pricking component 153. As shown in FIG. 2A, it is also preferable that the pair of guided components 157 extends in a direction perpendicular to the direction in which the first wing parts 155 are opposed to each other. On the side edge of each of the guided components 157, the protrusion A 158 is formed. The protrusion A 158 can make contact with the protrusion B 108 formed within the guider channel 107. As the protrusion A 158, two protrusions (158a, 158b) are preferably provided near the rear of the guided component as shown in FIG. 2A and FIG. 2B. The protrusions A (158a, 158b) and the protrusion B 108 are brought into contact with each other so that the protrusions A (158a, 158b) sandwiches therebetween the protrusion B 108 of the lancet holder 102, and thereby the lancet body 151 is secured to the lancet holder 152 (see FIG. 8(a) and the schematic illustration enclosed by dashed line in FIG. 5). When the force acting between the lancet holder 102 and the lancet body 151 exceeds a predetermined threshold, the protrusion B 108 provided within the guide channel 107 of the lancet holder 102 rides over the protrusion A 158 (specifically protrusion 158b) of the guided component 157 of the lancet body 151 (in other words, the protrusion A 158b of the guided component 157 rides over the protrusion 108), which causes the cease of the contact with protrusion B 108 and the protrusion A 158 (see FIG. 8(b)). As a result, the lancet body 151 can move along the guide channel 107 in the pricking position and the opposite direction thereto. For example, when the lancet holder 102 is further inserted while the lancet body 151 is still prevented from being inserted further, there is generated the force causing the lancet holder 102 and the lancet body 151 to move away from each other, and thereby the protrusion B 108 rides over the protrusion A 158b (in other words, the protrusion A 158b of the guided component 157 rides over the protrusion B 108). When the situation is viewed as the protrusion A 158b riding over the protrusion B 108, it is preferable that a forward face 108a of the protrusion B 108 is in a sloped form (see FIG. 1B). In a case where the protrusion B 108 is in a sloped form, the protrusion A 158b can be surely guided into the guide channel 107 after the protrusion A 158b has ridden up the protrusion B 108 (see FIGS. 8(a), (b)).

As shown in FIG. 2A and FIG. 2B, the lancet body 151 of type A has a pair of second wing parts 159. The pair of second wing parts 159 forward expands gradually toward the outside in substantially symmetrical configuration with respect to the pricking component 153 (i.e. in symmetrical configuration with respect to the longitudinal axis of the lancet 150). The pair of second wing parts 159 prevents the tip 153a of the pricking component 153 from protruding from the pricking opening 105 after pricking. That is to say, the pair of second wing parts 159 makes it impossible for the operator to touch the tip 153a of the pricking component 153 through the pricking opening 105 of the lancet holder 102. Specifically in the lancet assembly 100 that has been removed from the injector 200 after pricking, the pair of second wing parts 159 is capable of making contact with (i.e. abutting on) or hitting a stopper surface (indicated by reference numeral 180 in FIG. 1B) provided in the lancet holder 102 so as to restrict the movement of the pricking component 153 in the pricking direction. Due to the restricted movement of the pricking component 153, the tip 153a of the pricking component 153 does not protrude from the pricking opening 105. As shown in FIG. 2A and FIG. 2B, it is preferable that a base portion 159a of each of the second wing parts 159 has width larger than that of the edge portion thereof so as to improve the strength of the second wing parts 159.

Figure 24:
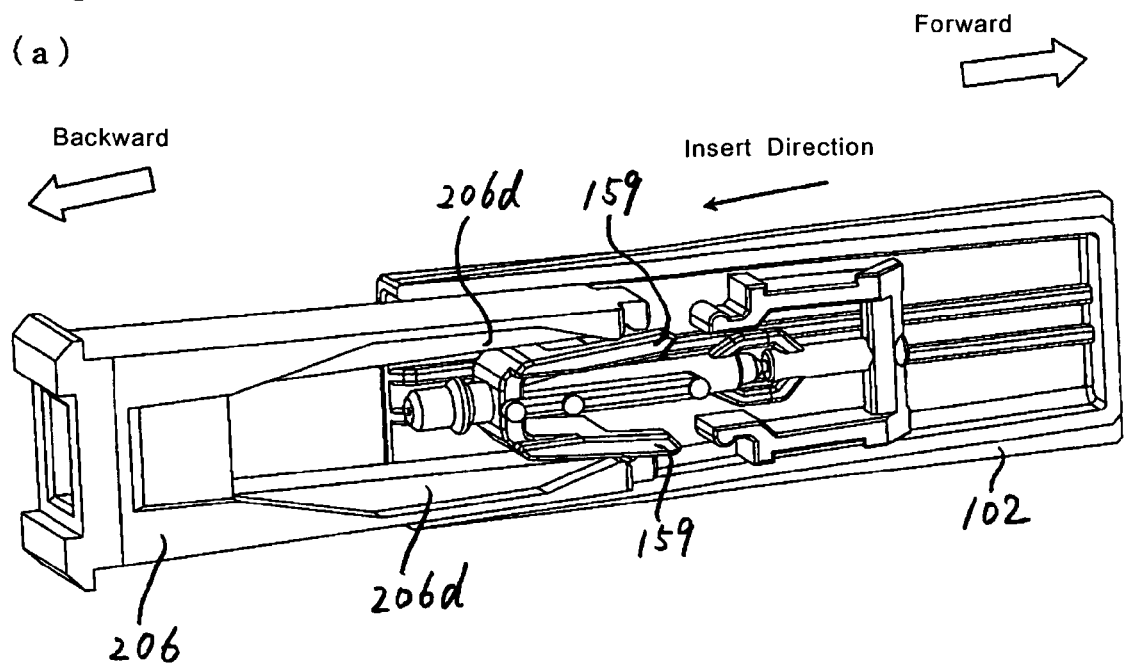
FIG. 24 shows a process (type A) of the accommodation of a pair of second wing parts in the bow-shaped groove.
Figure 24:
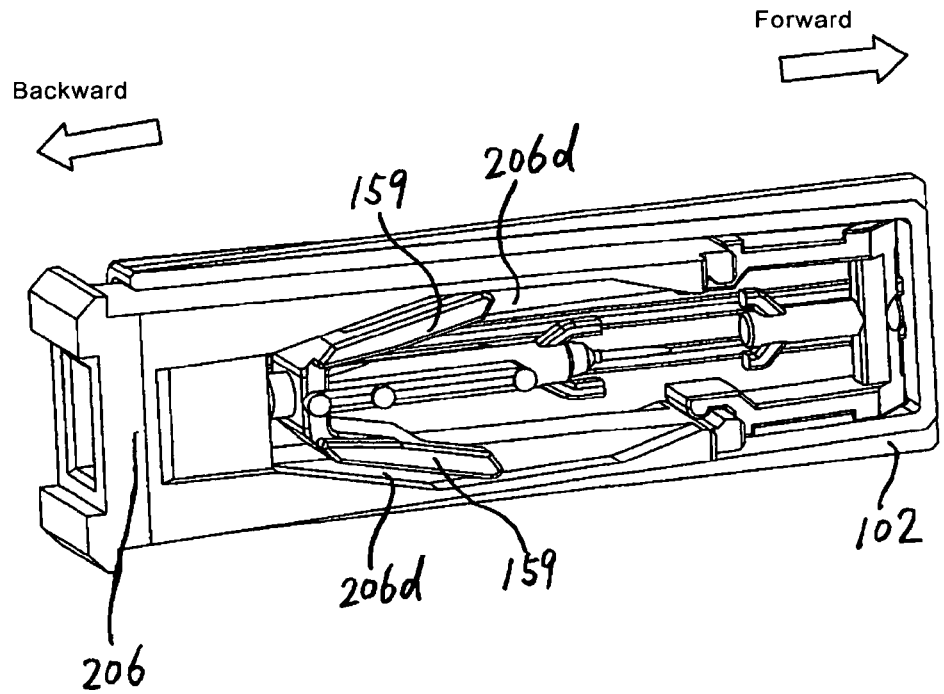

In the lancet cap removing part 206 of type A, the bow-shaped groove is provided. As the bow-shaped groove, there is provided a continuous recess or a continuous notch 206d having bow-shape as shown in FIG. 11(b). The bow-shaped groove serves to accommodate the pair of second wing parts 159. Consequently, the pair of second wing parts 159 can be placed in the bow-shaped groove 206d while preventing the second wing parts from being significantly deformed, when the lancet cap removing part 206 enters the lancet holder 102 upon loading the lancet assembly 100 into the injector 200. In other words, when the pricking component 153 is ready to be launched, the second wing parts 159 lie in the bow-shaped groove 206d without being virtually deformed, preferably with being not deformed at all (namely, there is occurred no deformation attributable to the creeping effect). FIG. 24(b) most clearly shows the state where the second wing parts 159 lie in the bow-shaped groove 206d of the lancet cap removing part 206. Since the pair of second wing parts 159 is kept in a non-deformed state as described above, the pair of the second wing parts 159 retains its original shape after the lancet cap removing part 206 is pulled out of the lancet holder 102. This makes it possible for the pair of the second wing parts 159 to surely make contact with or hit the stopper surface 180 of the lancet holder 102. The bow-shaped groove 206d is shown on the foreground in FIG. 11(b) for the ease of understanding, although the bow-shaped groove is actually disposed on the background of the drawing (only a part of the bow-shaped groove disposed on the background of the drawing is shown in FIG. 11(b)). It will be understood that the bow-shaped groove 206d for accommodating the second wing parts 159 is actually disposed on the background of the drawing, by making reference to FIG. 13(b) or FIG. 14(b). FIG. 13(b) or FIG. 14(b) show that the second wing parts 159 being within the lancet holder 102 are located on the background of the drawing.

FIG. 3 shows the state where the lancet 150 is housed in the lancet holder 102 and the lancet 150 is secured to the lancet holder 102 (for the ease of understanding, the lancet holder 102 is shown with one half thereof being cut away along the longitudinal direction). The lancet cap 152 is positioned on the side of the pricking opening 105 of the lancet holder 102, whereas the lancet body 151 is positioned on the side of the opening end 103 of the lancet holder 102. As described previously, the guided component 157 of the lancet body 151 slots into the guide channel 107 of the lancet holder 102, and the protrusion B 108 provided within the guide channel 107 is located between and in contact with the two protrusions A (158a, 158b) of the guided component 157, and thereby the lancet 150 is secured to the lancet holder 102 (such contact cannot be seen in FIG. 3, but is most clearly shown in FIG. 8(a)). That is to say, the lancet body 151 is secured to the lancet holder 102, while on the other hand the lancet cap 152 is not secured to the lancet holder 102. As a result, pressing only the lancet cap 152 in the pricking direction generates the force for departing the lancet cap 152 and the lancet body 151 from each other. Due to this force, the bridging component 154 is broken so that the lancet cap 152 and the lancet body 151 are separated from each other and the tip of the pricking component 153 is exposed.

Subsequently, when the separated lancet cap 152 is pressed in the pricking direction, the cap 152 moves forward. In the inside of the lancet holder 102 and near the pricking opening 105 thereof, there is provided a slope component 170 for guiding the separated lancet cap 152 to a position that is off the pricking pathway. While on the other hand, the lancet cap 152 is provided with a sloped portion 171 having a shape corresponding to the slope component 170. Specifically, the slope component 170 and the sloped portion 171 respectively have flat surfaces that allow them to make complementary contact with each other (i.e. abut against each other). The slope component 170 is clearly shown not only in FIG. 3 but also in FIG. 1B. The sloped portion 171 is clearly shown in FIG. 2A and FIG. 2B. Due to the slope component 170 and the sloped portion 171, when the separated lancet cap 152 is forced to move further forward, the sloped portion 171 of the lancet cap 152 slides while making contact with the slope component 170 of the lancet holder 102, thus allowing the lancet cap 152 to move to the position that is off the pricking pathway. FIG. 6 shows the state where the separated lancet cap 152 has deviated from the pricking pathway.

Figure 8:
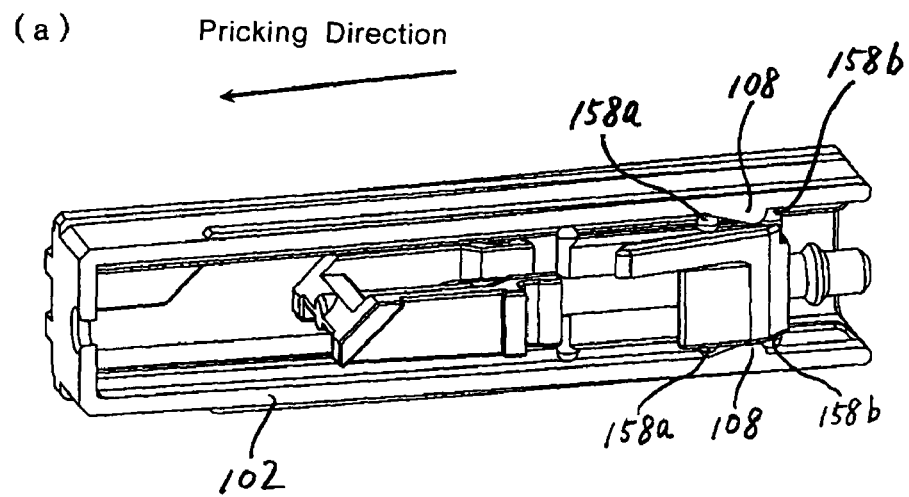
FIG. 8 is a schematic perspective view showing the state of the lancet of type A being housed in the lancet holder of type A, viewed from above in direction P indicated in FIG. 5 or FIG. 6 wherein the upper half of the lancet holder of FIG. 5
Figure 8:
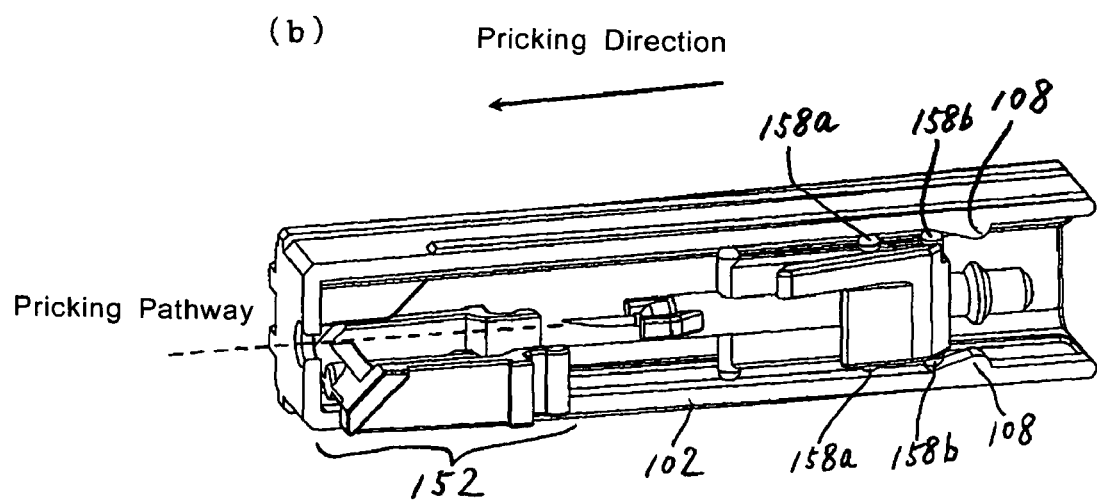

The movement of the lancet cap 152 will now be described in more detail. The slope component 170 of the lancet holder 102 is provided with a sloped surface 170a (see FIG. 1B and FIG. 5) disposed at an angle to the pricking pathway. Whereas and the sloped portion 171 of the lancet cap 152 has a surface capable of making complementary contact with the sloped surface 170a. Therefore, when the separated lancet cap 152 is pushed in the pricking direction, the lancet cap 152 slides forward while surface 170a of the lancet holder and the surface of the lancet cap are in contact with each other, which results in a forward and oblique movement of the lancet cap. For example, FIG. 8(a) and FIG. 8(b) show the states before and after the movement of the separated lancet cap 152. As the lance cap 152 moves from the position shown in FIG. 8(a) to the position shown in FIG. 8(b), it will be understood that the lancet cap 152 moves to the position that is off the pricking pathway. Track or route of the lancet cap's movement is shown in the upper portion of FIG. 6 wherein the track or route is viewed in the direction of P (i.e. from above). This track or route of the movement also indicates that the lancet cap 152 eventually moves and deviates from the pricking pathway of the pricking component 153. The angle of the sloped surface 170a with respect to the pricking pathway (namely, angle α of the track or route of the movement as shown in FIG. 6) is preferably in the range from 30° to 60°, more preferably in the range from 40° to 50°.

Since the lancet cap 152 moves forward in an oblique direction to deviate from the pricking pathway as described above, the pricking component 153 (more specifically, the lancet body 151 with the pricking component 153 exposed) can be launched forward without being obstructed by the lancet cap 152. FIG. 7 schematically shows the lancet assembly 100 upon pricking (namely at the time when the pricking component is being launched). As will be seen from FIG. 7, the tip 153a of the pricking component 153 is protruding from the pricking opening 105 without being obstructed by the lancet cap 152.

Figure 9B:
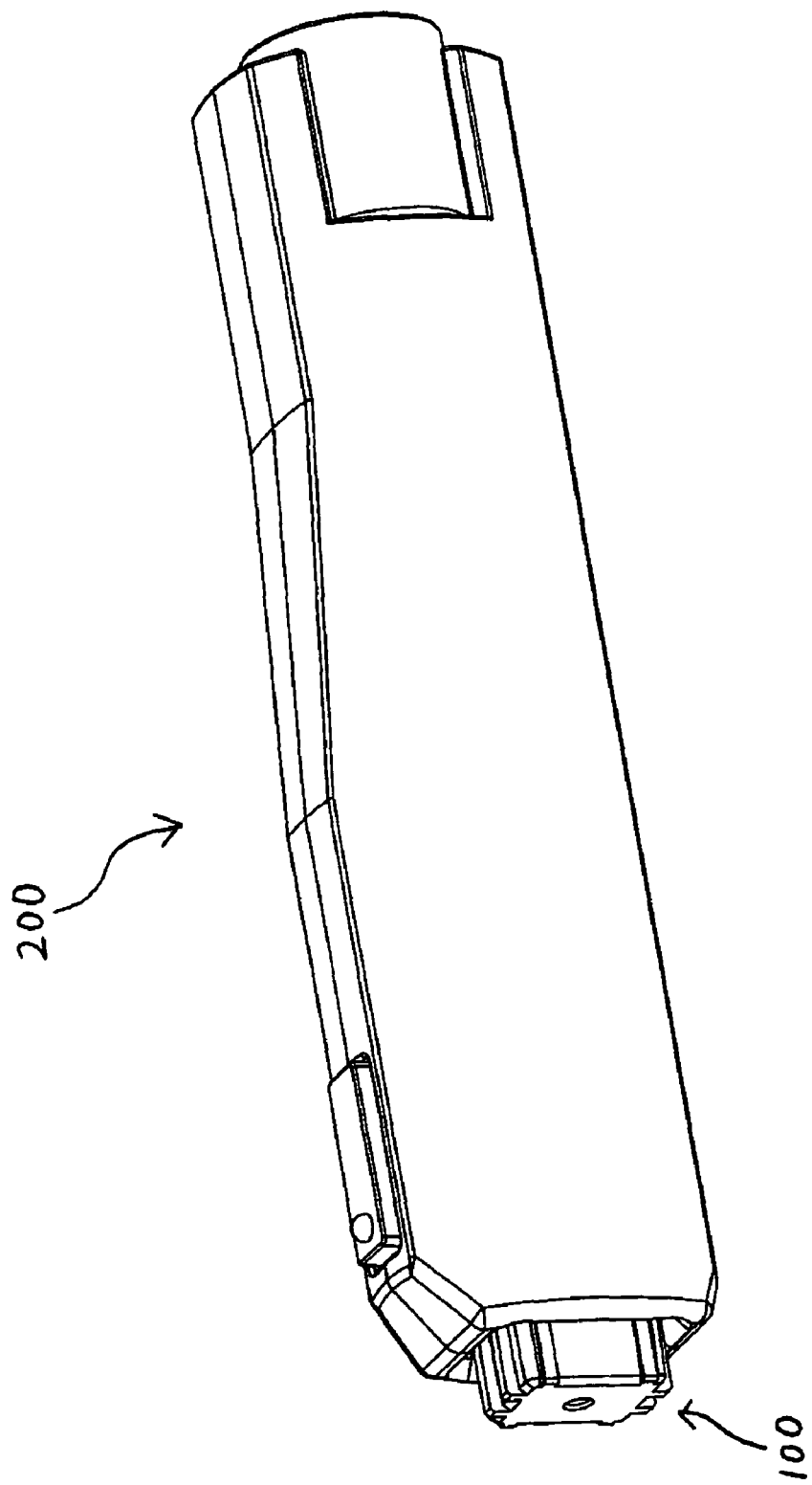
FIG. 9B is a schematic perspective view of the state where the lancet assembly of type A has been completely loaded into the injector of type A.

When the lancet assembly 100 of type A is loaded into the injector 200 of type A for use, the assembly 100 is inserted through the front end opening 202 of the injector 200 backward (in the direction indicated by arrow A) as shown in FIG. 9A. This loading operation is carried out by holding the lancet holder 102 with one hand and then inserting the lancet holder 102 through the front end opening 202 of the injector 200 while holding the injector 200 with the other hand. The loading is complete when the lancet holder 102 cannot be inserted further by the force exerted by an ordinary person. The state when loading has been completed is shown in FIG. 9B. By carrying out the loading operation, the plunger of the injector 200 is retracted and thereby the force required for launching the pricking component 153 is stored in the plunger. The retracting of the plunger is accompanied by the following actions:

(1) The bridging component 154 is broken so that the lancet cap 152 is separated from the lancet body 151; and then
(2) The separated lancet cap 152 moves and deviates from the pathway of the pricking.

Figure 10A:
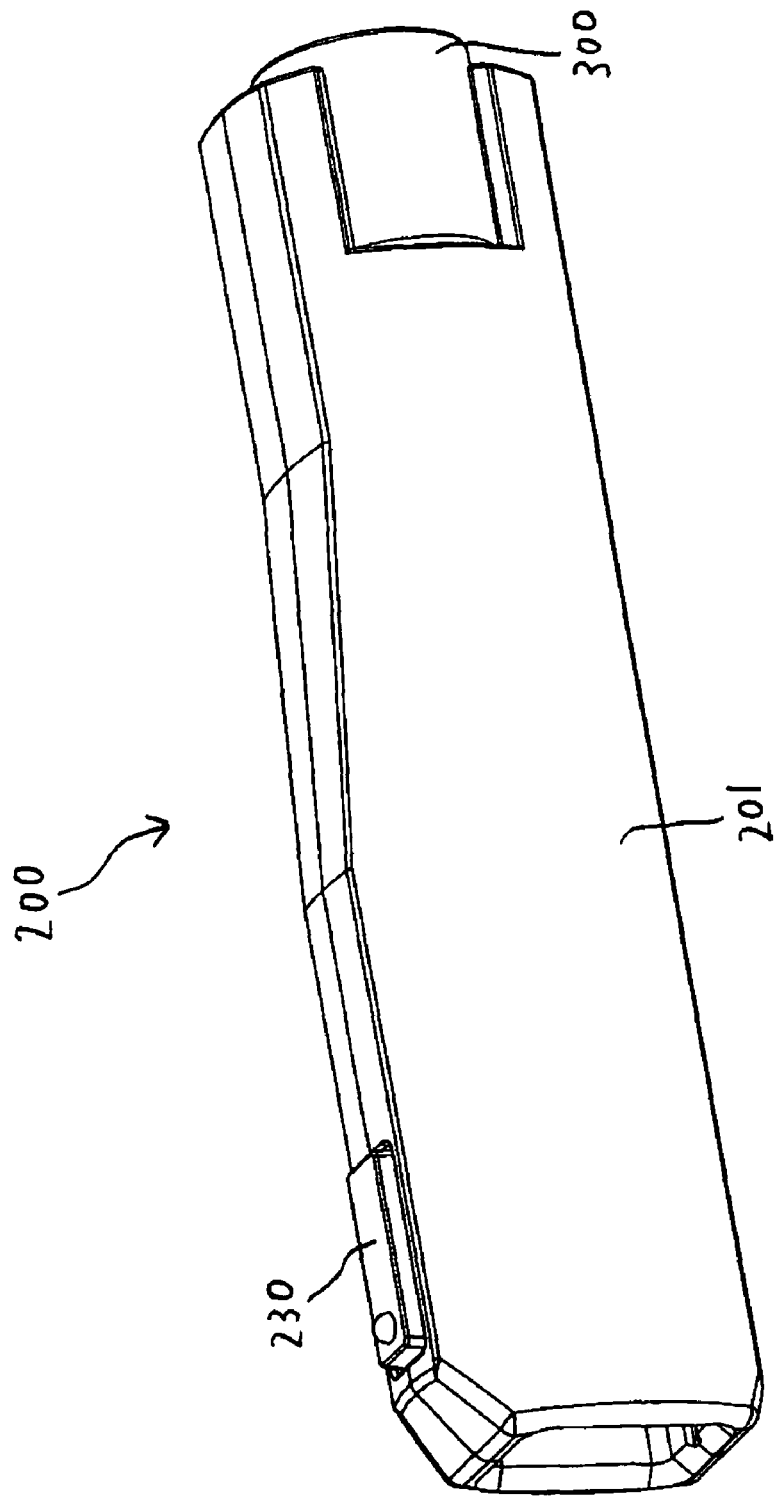
FIG. 10A is a schematic perspective view of the external appearance of the injector of type A.
Figure 10B:
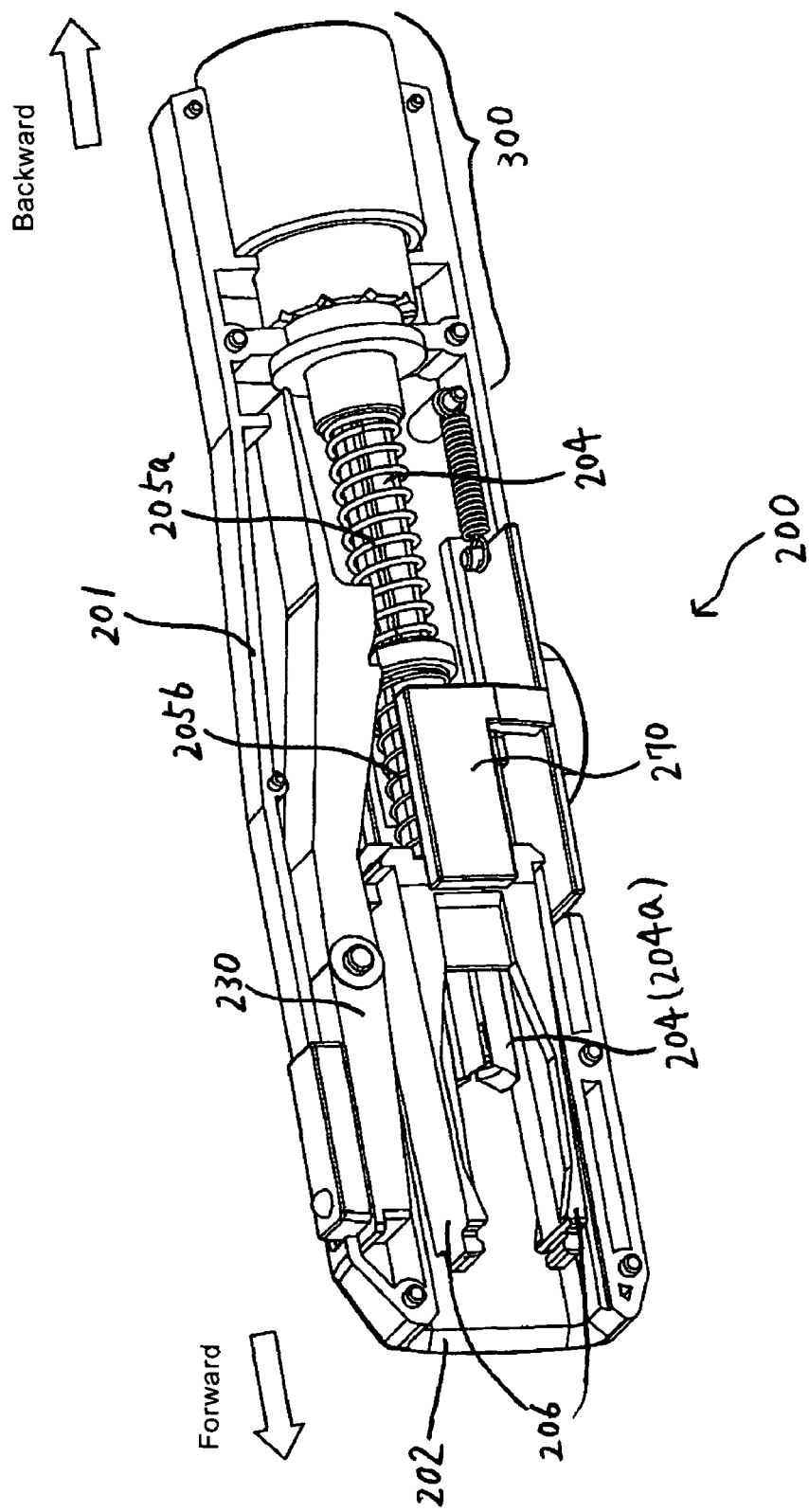
FIG. 10B is a schematic perspective view of the inner structure of the injector of type A.
Figure 10C:
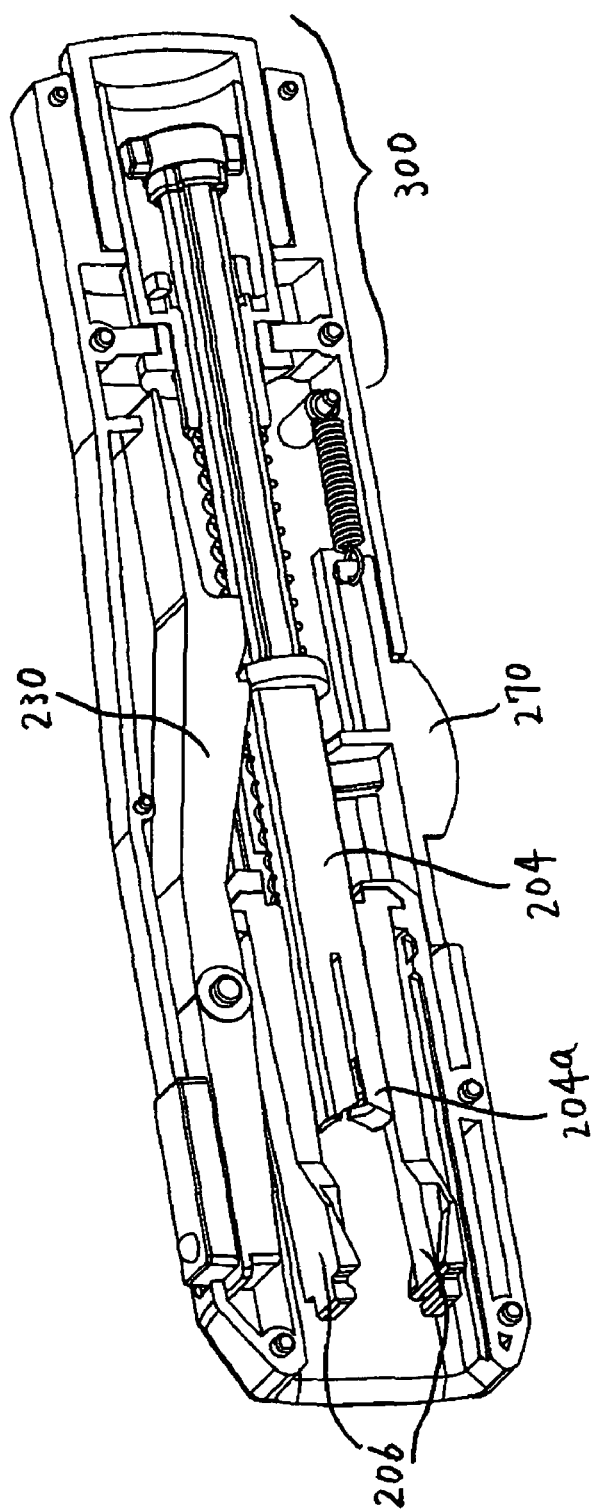
FIG. 10C is a schematic perspective view of the inner structure of the injector of type A, with a part thereof shown in FIG. 10B cut away.
Figure 11:
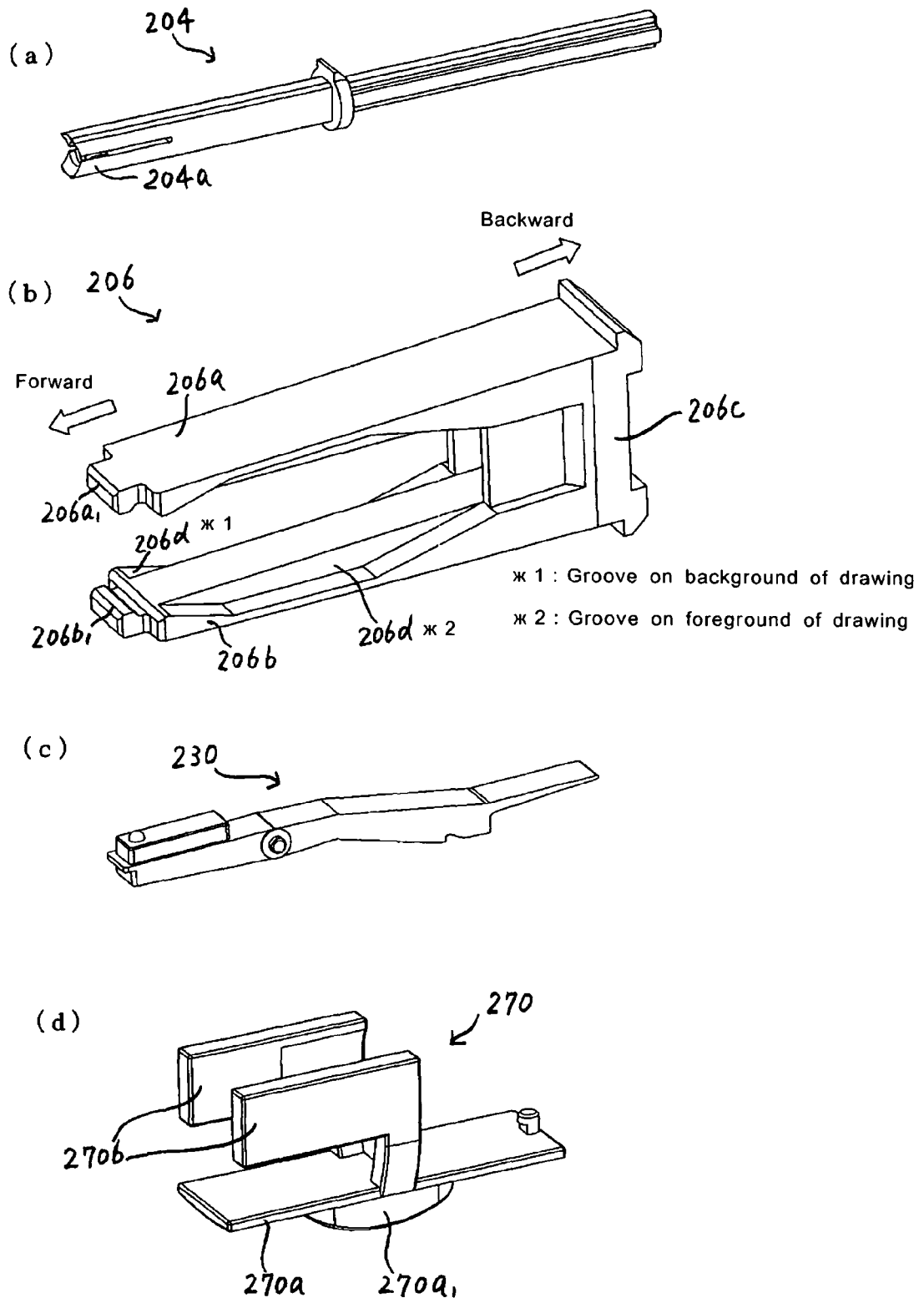
FIG. 11 is a schematic perspective view of components of the injector of type A.

FIGS. 10A to 10C show the injector 200 of type A of the present invention. FIG. 10A shows an external appearance of the injector 200, and FIGS. 10B and 10C show the inside of the injector 200. As shown in FIGS. 10B and 10C, the injector 200 has the plunger 204, the lancet cap removing part 206, the trigger lever 230, the ejector 270, the release spring 205a, the return spring 205b and the pricking depth adjusting mechanism 300. The schematic perspective views of the plunger 204, the lancet cap removing part 206, the trigger lever 230 and the ejector 270 are respectively shown in FIG. 11 (a) to 11(d).

Figure 12:
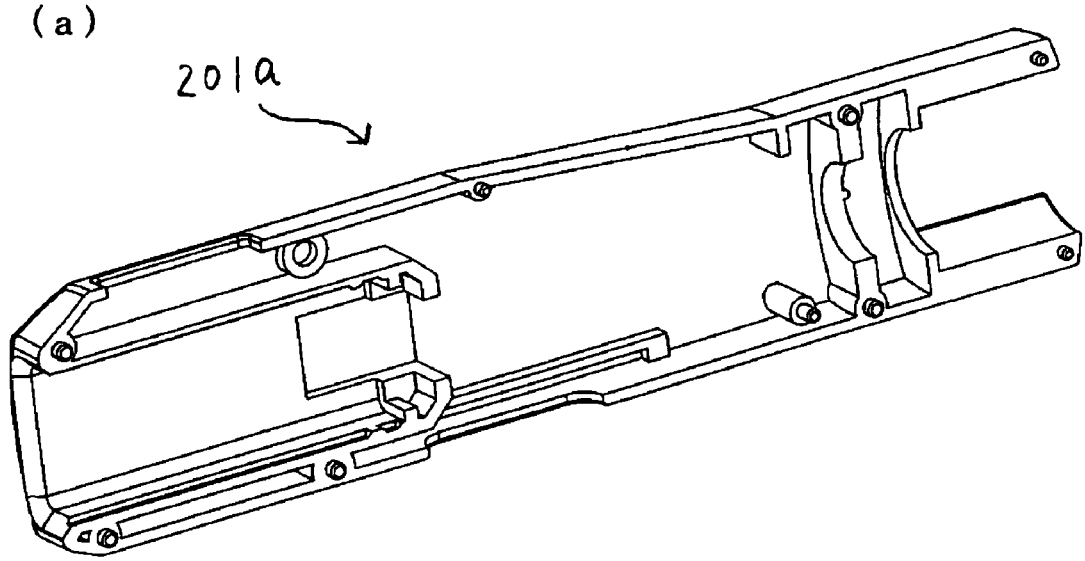
FIG. 12 is a schematic perspective view of an injector housing of type A.
Figure 12:
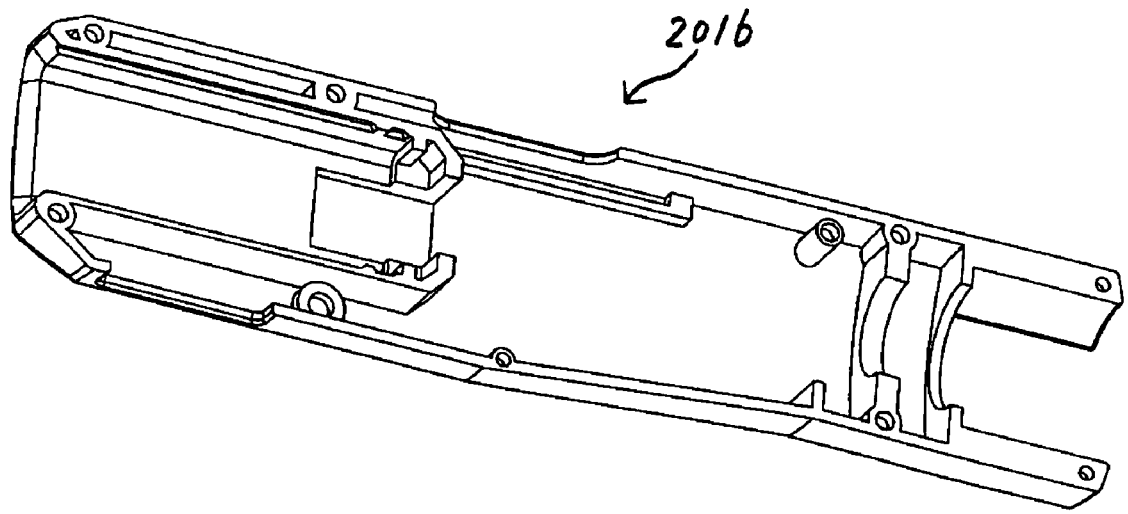

The housing 201 of the injector 200 is preferably constituted from the halved members. For example, a member 201a shown in FIG. 12(a) and a member 201b shown in FIG. 12(b) are integrally combined to form the housing 201.

The plunger 204 is disposed along the longitudinal direction of the injector 200. The plunger 204 has a function of launching the lancet body 151 in the pricking direction. As shown in FIG. 10C and FIG. 11(a), the front end portion 204a of the plunger 204 is configured to engage with the rear end of the lancet body 151 (i.e. the engaging portion of the rear end of the lancet body is indicated by reference numeral 165 in FIG. 2A and FIG. 4D). By inserting the lancet body 151 into the injector 200 upon loading the lancet assembly 100 into the injector 200, the front end portion 204a of the plunger 204 engages with the rear end 165 of the lancet body 151. Subsequently, as the lancet body 151 is inserted further backward, the plunger 204 is thrust backward. As a result, the spring 205a provided on the plunger 204 is compressed, and the force required for launching the pricking component 153 can be stored in the plunger 204.

The lancet cap removing part 206 can engage with the lancet cap 152, and thus it functions to remove the lancet cap 152 upon loading the lancet assembly 100 in the injector 200. As shown in FIG. 11(b), the lancet cap removing part 206 has such a configuration that two long members 206a and 206b protrude forward (hence the lancet cap removing part 206 may be called "protruding rod") The edge portions $206a_1$, $206b_1$ of the long members 206a and 206b are capable of engaging with the pair of first wing parts 155 of the lancet cap 152. The lancet cap removing part 206 is installed in the injector 200 in such a manner that the edge portions $206a_1$, $206b_1$ of the lancet cap removing part 206 are positioned near the front end opening 202 of the injector 200 whereas the base portion 206c of the lancet cap removing part 206 is positioned on the rear end side of the injector 200 (see FIG. 10B). Due to this, the lancet cap 152 and the lancet cap removing part 206 can engage with each other upon loading the lancet assembly 100 into the injector 200. It is preferable that each of the edge portions $206a_1$, $206b_1$ of the lancet cap removing part 206 have such a shape that is complementary with each of the edges 156 of the first wing parts 155 of the lancet cap 152 so as to achieve a more reliable engagement therebetween.

The injector 200 has the ejector 270 for removing the lancet holder 102 from the injector 200 after pricking. The ejector 270 is provided in the injector 200 in such a manner that only a part $270a_1$ of the sliding portion 270a protrudes from the injector housing 201 (see FIG. 11(d)). When the loading of the lancet holder 102 into the injector 200 is completed, the front portion 270b of the ejector 270 makes it possible to contact with (i.e. abut on) the edge of the opening end 103 of the lancet holder 102. Thus, as the part $270a_1$ is pressed to slide forward, the front portion 270b of the ejector 270 acts to push the lancet holder 102 so that the lancet holder 102 is ejected from the injector 200.

In the spent lancet holder 102 which has been ejected from the injector 200 by the ejector 270 after pricking, the separated lancet cap 152 and the lancet body 151 with the tip of the pricking component 153 exposed are contained. Since the pair of second wing parts 159 of the lancet body 151 is capable to make contact with (i.e. abut against) or hit the stopper surface 180 of the lancet holder 102 as described previously, the pricking component 153 will not protrude from the pricking opening 105. As a result, the spent lancet assembly 100 can be safely disposed of.

With reference to FIGS. 13 to 23, the procedure of operation will now be described serially from the loading of the lancet assembly 100 of type A through the completion of loading and the pricking until the ejection of the spent lancet assembly 100 after pricking. FIGS. 13 to 23 show the time changes of the lancet assembly 100 and the injector 200 in the sequential order of the figure numbers. FIGS. 13(a) to 23(a) and FIGS. 13(b) to 23(b) show the same states, respectively, when the figure number is the same.

Figure 13A:
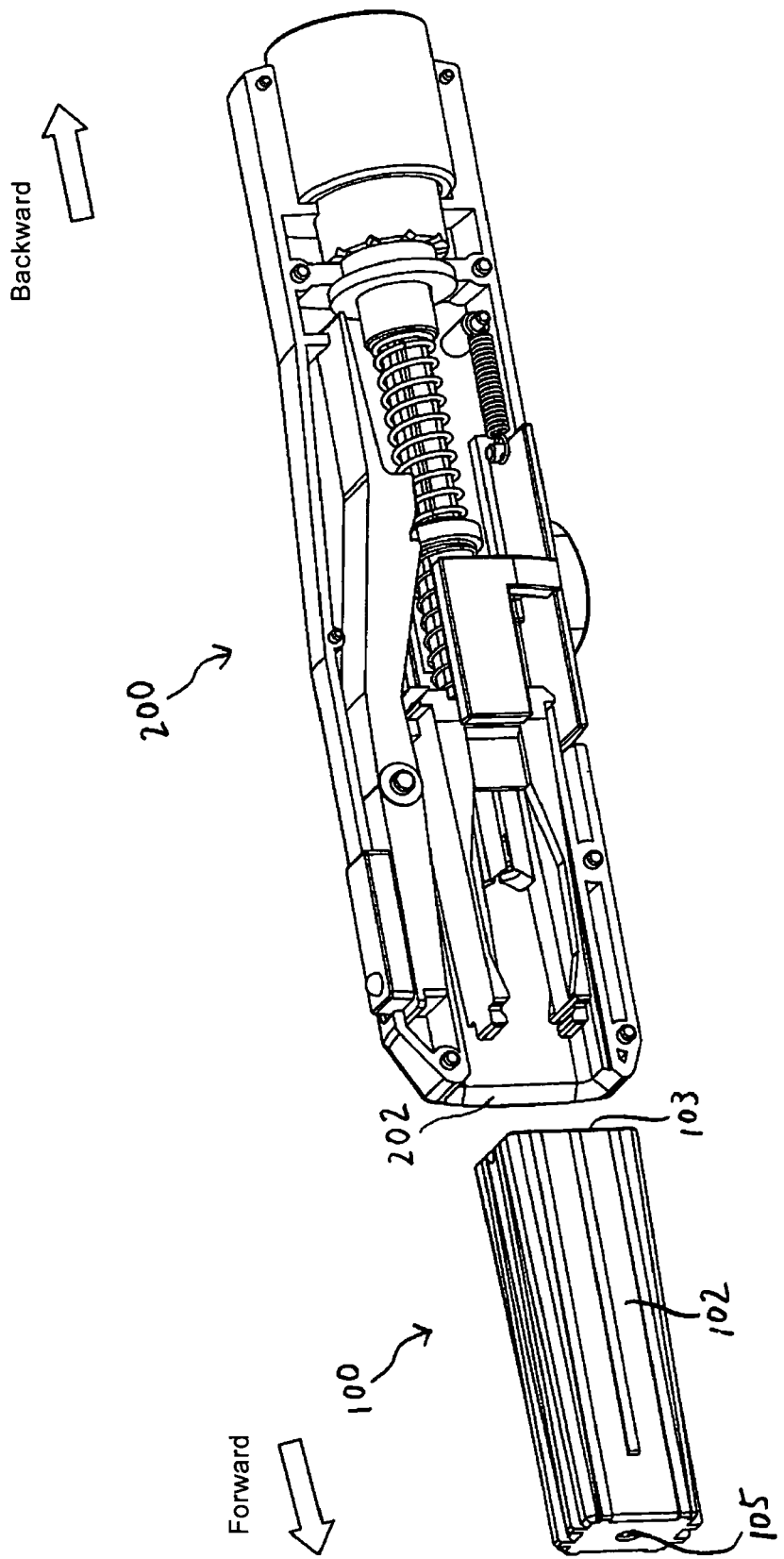
FIG. 13(a) is a schematic perspective view (type A) of the state before the lancet assembly is inserted into the injector.
Figure 13B:
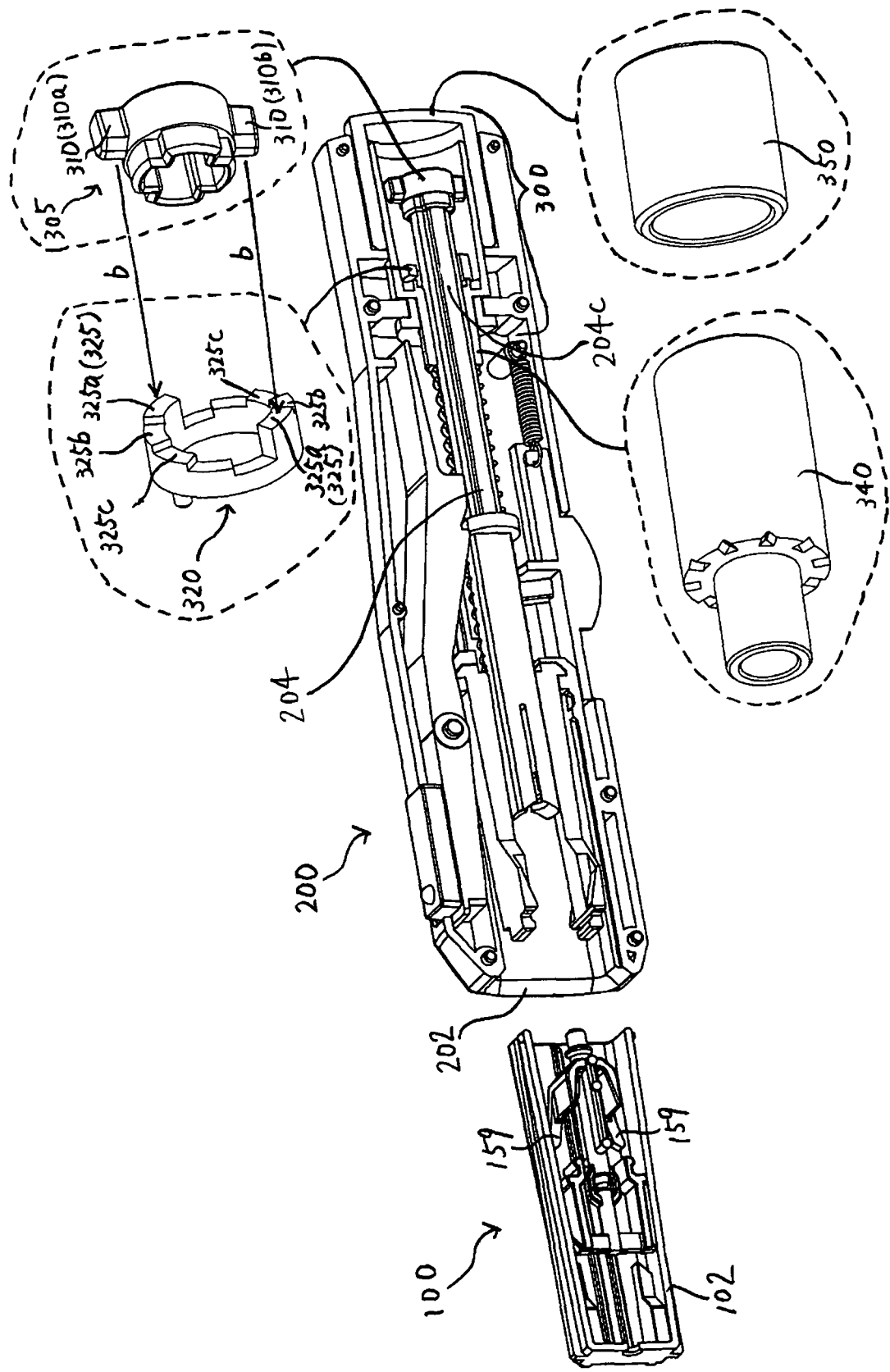
FIG. 13(b) is a schematic perspective view (type A) of the state before the lancet assembly is inserted into the injector.

First, as shown in FIGS. 13(a) and 13(b), the lancet assembly 100 and the injector 200 are prepared. In this case, the prepared lancet assembly 100 is one in which the lancet is housed in the lancet holder 102 and the lancet body 151 is secured to the lancet holder 102. Then, the lancet holder 102 is inserted into the injector 200 through the front end opening 202 of the injector 200 to commence the loading of the lancet assembly 100. Upon loading, the lancet holder 102 is inserted in such an orientation that the pricking opening 105 of the lancet holder 102 faces forward and the opening end 103 of the lancet holder 102 faces backward, as shown in FIG. 13(a). In other words, the opening end 103 of the lancet holder 102 firstly passes through the front end opening of the injector 200.

Figure 14A:
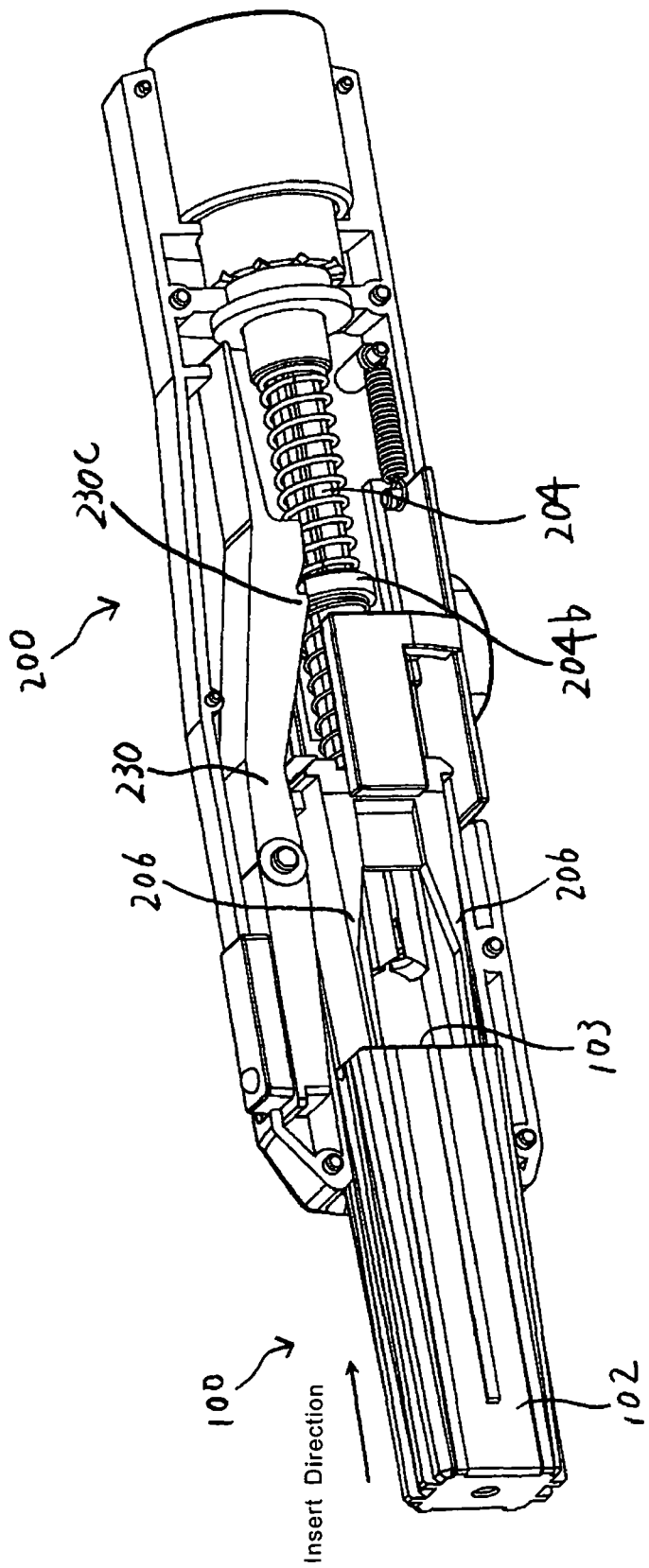
FIG. 14(a) is a schematic perspective view (type A) of the state around the time when insertion of the lancet assembly into the injector is commenced.
Figure 14B:
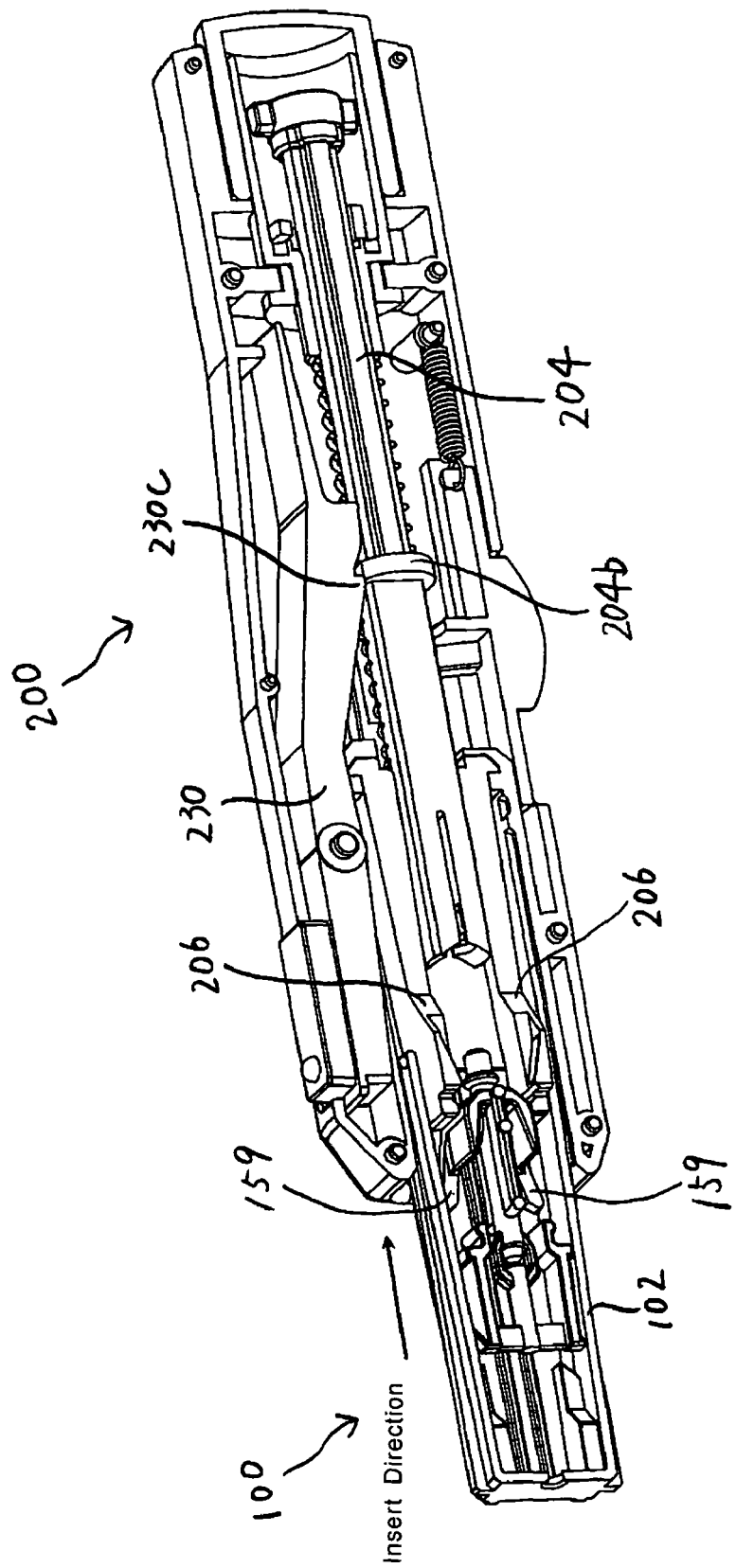
FIG. 14(b) is a schematic perspective view (type A) of the state around the time when insertion of the lancet assembly into the injector is commenced, showing that the lancet removing part has been inserted into the lancet holder.

Upon loading the lancet assembly 100, the lancet cap removing part 206 enters the lancet holder 102 through the opening end 103 of the lancet holder 102, as shown in FIGS. 14(a) and 14(b). As the insertion is continued, edges 156 of the pair of first wing parts 155 of the lancet cap 152 are brought into contact with the edge portions $206a_1$, $206b_1$ of the lancet cap removing part 206. As the insertion is continued further, the edges 156 of the first wing parts 155 engage integrally with the edge portions $206a_1$, $206b_1$ of the lancet cap removing part 206, as shown in FIG. 15(a) and FIG. 15(b) (particularly see FIG. 15(b)). Substantially simultaneously as this engagement takes place, the engagement portion 165 of the rear end of the lancet body makes contact with (i.e. abuts on) the front end 204a of the plunger 204 of the injector 200 (see FIG. 15(b)). The engagement portion 165 and the front end 204a are finally interconnected integrally. It is shown in FIG. 16(b) that the rear end portion 165 of the lancet body 151 and the front end 204a of the plunger 204 have been completely interconnected. When the lancet holder 102 is further inserted after the lancet body 151 and the plunger 204 make contact with each other, the lancet body 151 secured to the lancet holder 102 acts to press the plunger 204, which results in the retracting of the plunger 204.

Figure 16A:
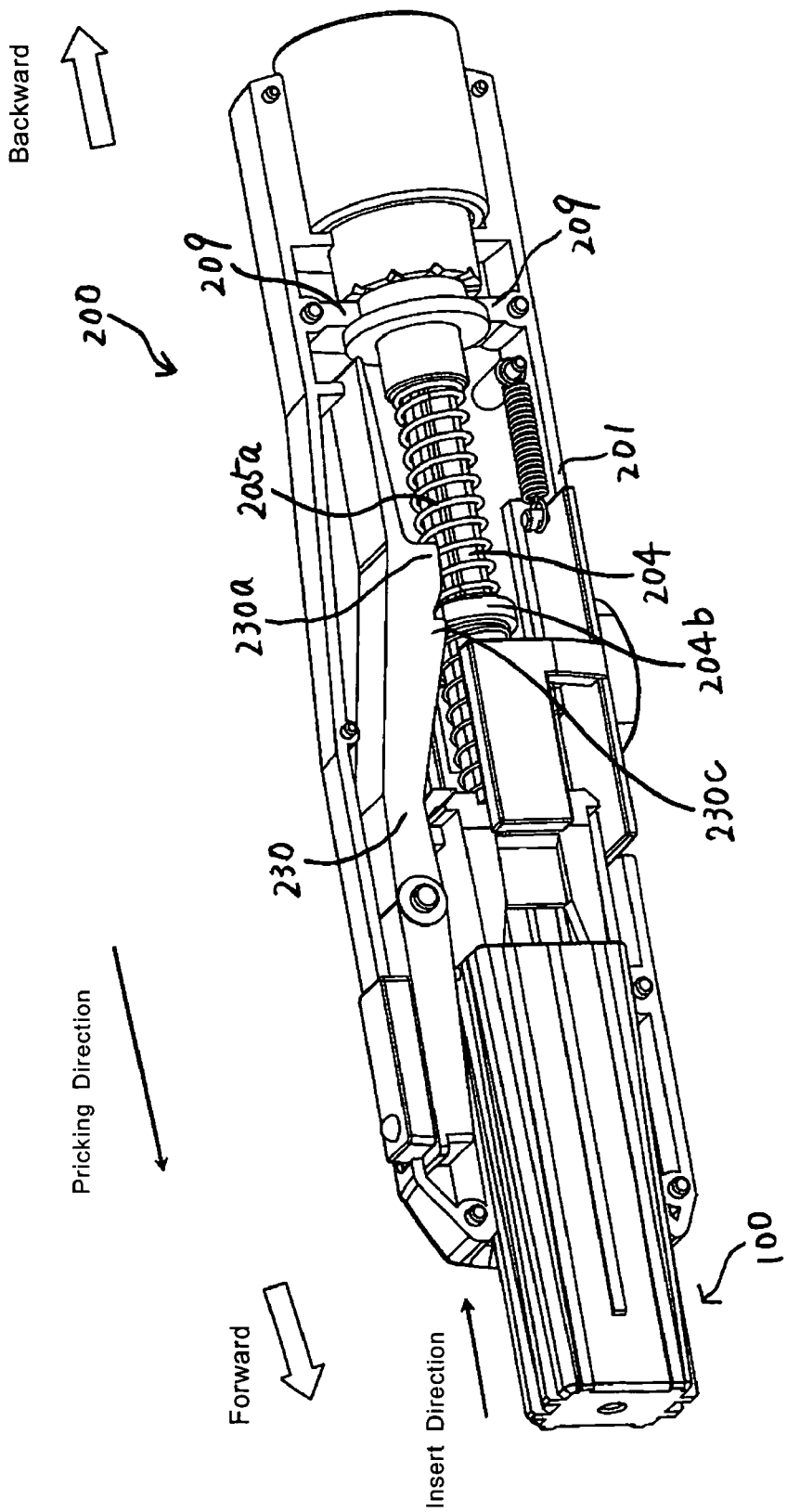
FIG. 16(a) is a schematic perspective view (type A) of the state where the lancet assembly is being inserted into the injector.
Figure 16B:
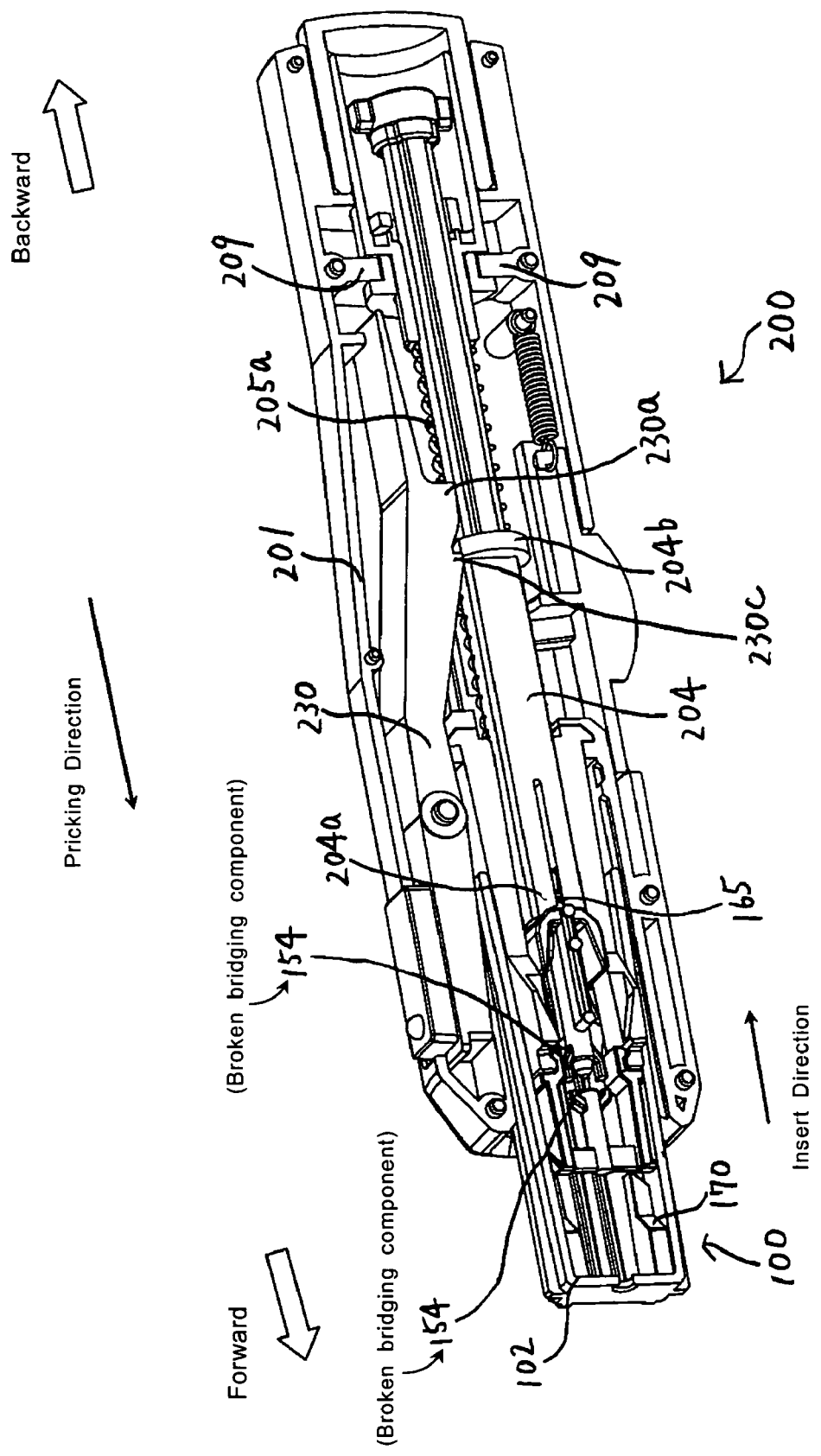
FIG. 16(b) is a schematic perspective view (type A) of the state where the lancet assembly is being inserted into the injector, and the rear end portion of the lancet body and the front end of the plunger have been completely interconnected.

As shown in FIG. 16(a) and FIG. 16(b) (particularly in FIG. 16(a)), the plunger 204 has a flange 204b formed at the intermediate portion thereof. A release spring 205a is provided around the plunger 204 and between the flange 204b and a partition 209 provided within the injector housing 201. The spring 205a functions to move the plunger 204 forward (namely in the pricking direction) when there is no external force acting on the plunger 204. In the initial state where no external force is acting, the flange 204b of the plunger 204 and the engagement portion 230c (or the front stepped portion 230c) of the trigger lever 230 are in engagement, as shown in FIG. 14(a) and FIG. 14(b). Such engagement between the flange 204b and portion 230c makes it possible to restrict the forward movement of the plunger 204. The rear end portion 165 of the lancet body 151 can press the plunger 204 backward against the force of the spring 205a urging the plunger 204 to return forward. The retracting of the plunger eventually causes the spring 205a of the plunger 204 to be compressed and the force required for launching the pricking component 153 is stored in the plunger 204.

Whereas the lancet body 151 is secured to the lancet holder 102, the lancet cap 152 is not secured to the lancet holder 102. The further insertion of the lancet holder from the state shown in FIG. 15(b) causes the lancet cap 152 to be pressed by the lancet cap removing part 206 in the pricking direction. That is, there is generated the force causing the lancet cap 152 and the lancet body 151 to depart from each other, and thereby the bridging component 154 for interconnecting the lancet cap 152 and the lancet body 151 is broken in two so that the lancet cap 152 is separated from the lancet body 151. It is shown in FIG. 16(b) that the lancet cap 152 has been separated from the lancet body. Since the lancet cap 152 is separated while leaving the pricking component 153 in the lancet body 151, the breaking of the bridging component 154 provides the lancet body 151 with the tip of the pricking component 153 exposed.

Figure 17A:
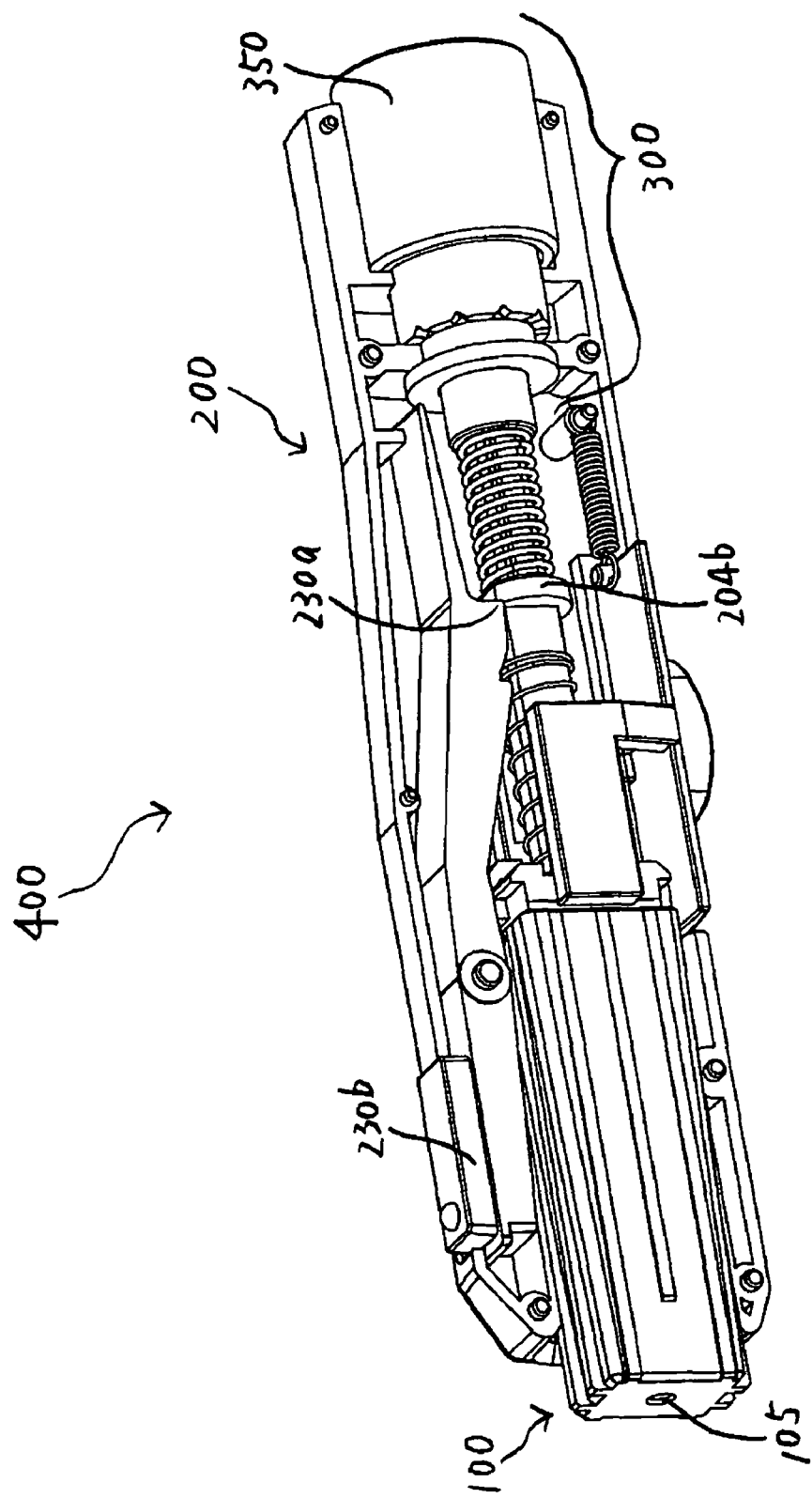
FIG. 17(a) is a schematic perspective view (type A) of the state where the lancet assembly has been completely loaded into the injector.
Figure 17B:
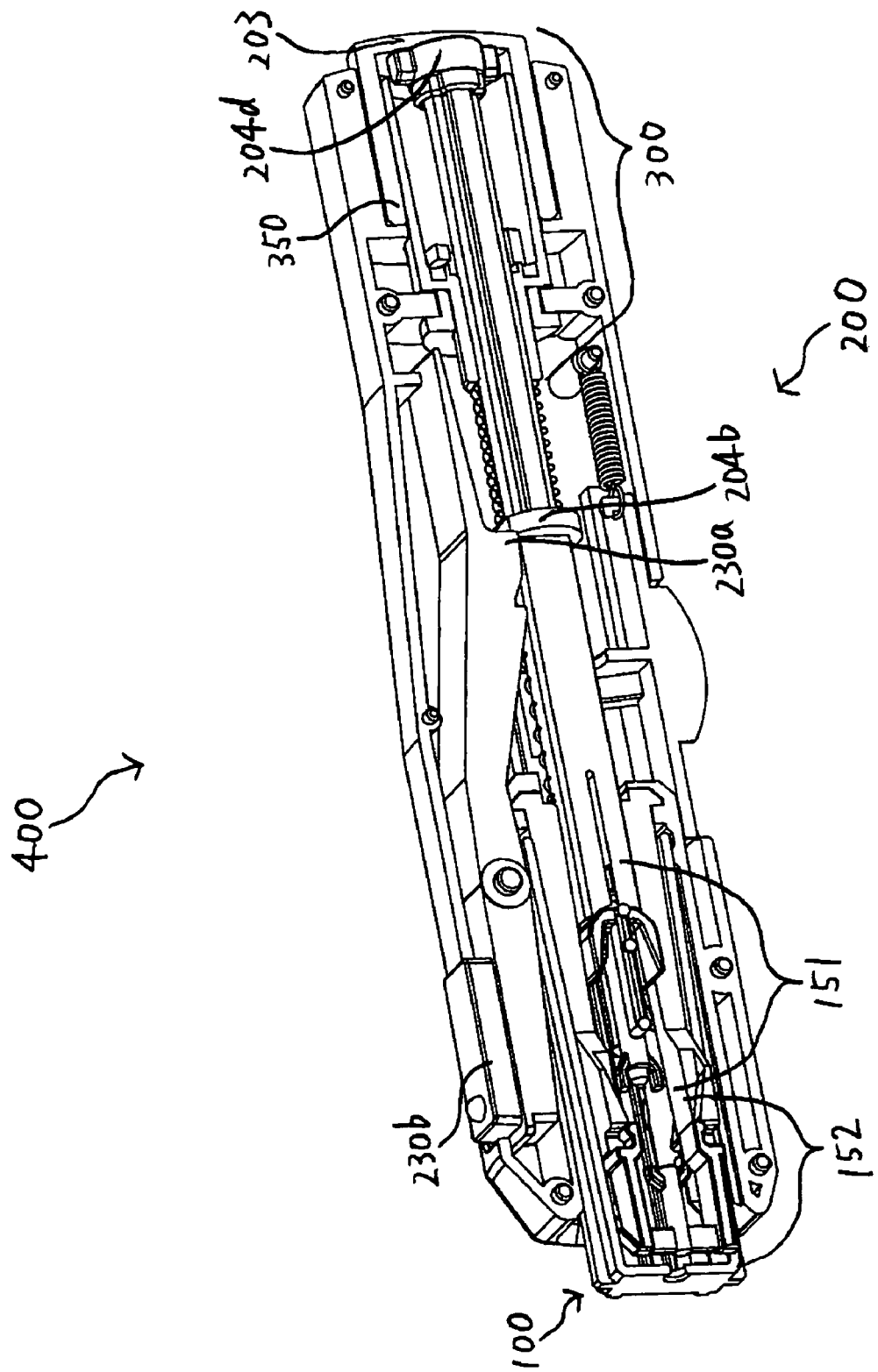
FIG. 17(b) is a schematic perspective view (type A) of the state where the lancet assembly has been completely loaded into the injector.

When the lancet holder 102 is inserted further into the injector 200 following the separation, the separated lancet cap 152 is further pressed forward by the lancet cap removing part 206. Thus, the separated lancet cap 152 moves forward within the lancet holder 102 toward the position that is off the pricking pathway while keeping contact with and sliding on the slope component 170. The slope component 170 provided within the lancet holder 102 is clearly shown in FIG. 16(b). It is shown in FIG. 17(b), FIG. 6 and FIG. 8(b) that the separated lancet cap 152 has moved to the position that is off the pricking pathway.

The injector 200 has the trigger lever 230 (see FIG. 16(a) or FIG. 16(b)) that is pressed to launch the pricking component. The trigger lever 230 is configured to be subject to the force acting inwardly. For example, the trigger lever 230 is configured to be subject to the inward force toward the inside of the injector 200 by a leaf spring thereof (not shown). After the flange 204b of the plunger 204 moves backward while pressing the rear stepped portion 230a of the trigger lever 230 toward the outside, the front portion of the flange 204b of the plunger 204 is located adjacent to the rear stepped portion 230a of the trigger lever 230, which will lead to the cocking of the trigger lever 230 as shown in FIG. 17(a) and FIG. 17(b). In this state of the cocking, the distance between the rear end 204d of the plunger 204 and the inner wall surface 203 on the rear end of the injector 200 (specifically, "inner wall surface 203" is the inner wall surface of an outer drum 350 of the pricking depth adjusting mechanism 300 to be described later) may be very small, or may be zero meaning that the rear end 204d and the inner wall surface 203 are in contact with each other, as shown in FIG. 17(b).

The rear end 204d of the plunger 204 and inner wall surface 203 on the rear end of the injector 200 finally make full contact with each other (i.e. abut against each other), which prevents the plunger 204 from being retracting further. Therefore, when the lancet holder 102 is forced to move further in the direction of insertion, the lancet holder 102 receives the force causing it to move in the direction of insertion, whereas the lancet body 151 receives the force resisting it. In this state, an attempt to move the lancet body 151 in the direction of insertion by inserting the lancet holder 102 is prevented since the lancet body 151 is in engagement with the plunger 204 (which cannot be retracted further), and thereby the force causing the lancet cap 152 and the lancet body 151 to depart from each other is generated. In this case, when the force exceeds a predetermined threshold, the lancet body 151 is no longer secured to the lancet holder 102, which is shown in detail in FIG. 8(a) and FIG. 8(b). FIG. 8(a) shows that the lancet body 151 is secured to the lancet holder 102, whereas FIG. 8(b) shows that the lancet body 151 is no longer secured to the lancet holder 102. These will now be described in detail. As the lancet holder 102 is caused to move further in the direction of insertion, the protrusion B 108 provided within the guide channel 107 of the lancet holder 102 rides over the protrusion A 158 provided on the guided component 157 of the lancet body 151 (in other words, the protrusion A 158 of the guided component 157 rides over the protrusion B 108 provided within the guide channel 107 of the lancet holder 102), and thereby the contact between the protrusion B 108 and the protrusion A 158 of the guided component 157 ceases. That is, after the protrusion B 108 rides over the protrusion A 158, the protrusion B 108 and the protrusion A 158 are no longer in contact with each other, so that the lancet body 151 can move in the direction of pricking or in the opposite direction along the guide channel 107.

Upon inserting the lancet holder 102 into the injector 200 to the point where the lancet body 151 can move in the pricking direction and in the opposite direction, the lancet cap 152 is pressed by the lancet cap removing part 206 so that the lancet cap is separated from the lancet body 151 and finally the separated lancet cap reaches the position off the pricking pathway. FIG. 17(b) shows that the separated lancet cap 152 has moved to the position that is off the pricking pathway.

Upon loading the lancet assembly, the lancet cap removing part 206 enters the lancet holder 102 so that the pair of second wing parts 159 is accommodated in the bow-shaped groove 206d of the lancet cap removing part 206. It is shown in FIG. 24(a) and FIG. 24(b) that the pair of second wing parts 159 is accommodated in the bow-shaped groove 206d. In FIG. 24(a) and FIG. 24(b), the position is reversed from that of FIGS. 13 to 23 with respect to "forward" and "backward", and the back side of the lancet holder 102 is shown. FIG. 24(a) shows the state around the time when the accommodation of the pair of second wing parts 159 into the bow-shaped groove 206d is commenced, whereas FIG. 24(b) shows the state when the loading has been completed and the second wing parts 159 lie in the bow-shaped groove 206d. As can be seen from FIG.

24(b), the second wing parts 159 lie in the bow-shaped groove 206d without being in a deformed state.

The Loading of the lancet assembly by inserting the lancet holder 102 into the injector 200 is completed through the following steps (i) to (V):

(i) The lancet cap 152 is separated from the lancet body 151, so that the tip of the pricking component 153 is exposed whereas the pricking component 153 remains situated in the lancet body 151;

(ii) The separated lancet body 151 moves to the position that is off the pricking pathway;

(iii) The plunger is retracted;

(iv) The flange 204b of the plunger 204 and the trigger lever 230 becomes in a cocked state; and (v) The lancet body 151 is no longer secured to the lancet holder 102, and thus completing the loading operation. It should be noted that "steps (i) and (ii)" and "steps (iii) to (v)" proceed substantially concurrently. It should be also noted that the step (iv) and the step (v) may take place substantially simultaneously.

The state after the completion of the loading is shown in FIG. 17(a) and FIG. 17(b). In this state, the pricking device 400 of the present invention composed of the lancet assembly 100 and the injector 200 is ready for pricking. That is to say, the lancet body 151 (specifically the lancet body with the tip of the pricking component exposed) is ready to be launched. The lancet holder 102 is securely held in the injector 200, by engaging a semispherical protrusion 111 (see FIG. 1A) of the lancet holder with the recess (not shown) formed in the injector 200. The semispherical protrusion 111 may be provided on the external surface of the lancet holder 102 at a position adjacent to the opening end 103 of the lancet holder 102.

Figure 18A:
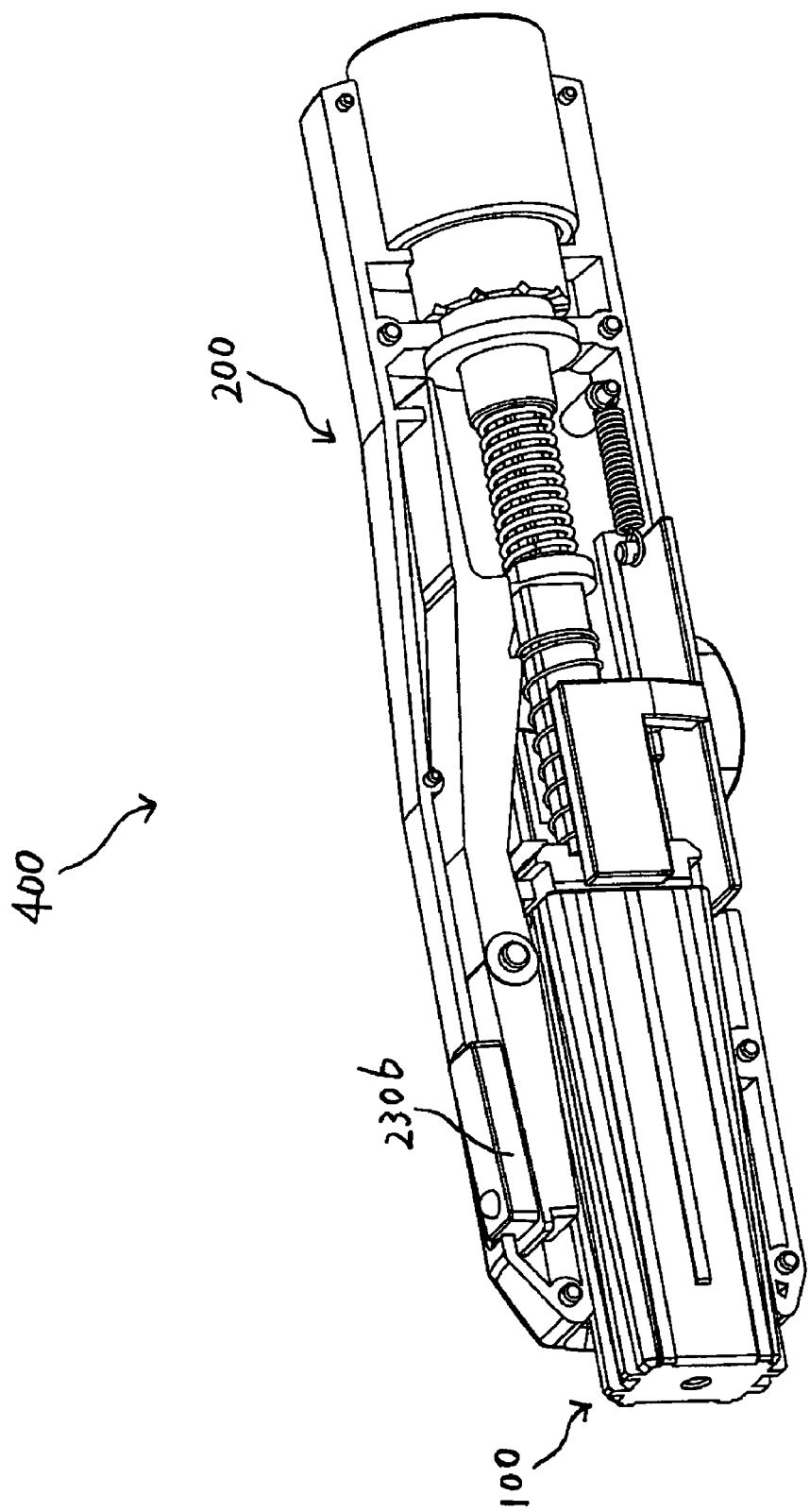
FIG. 18(a) is a schematic perspective view (type A) of the state at the point when the trigger lever is pressed to carry out the pricking.
Figure 18B:
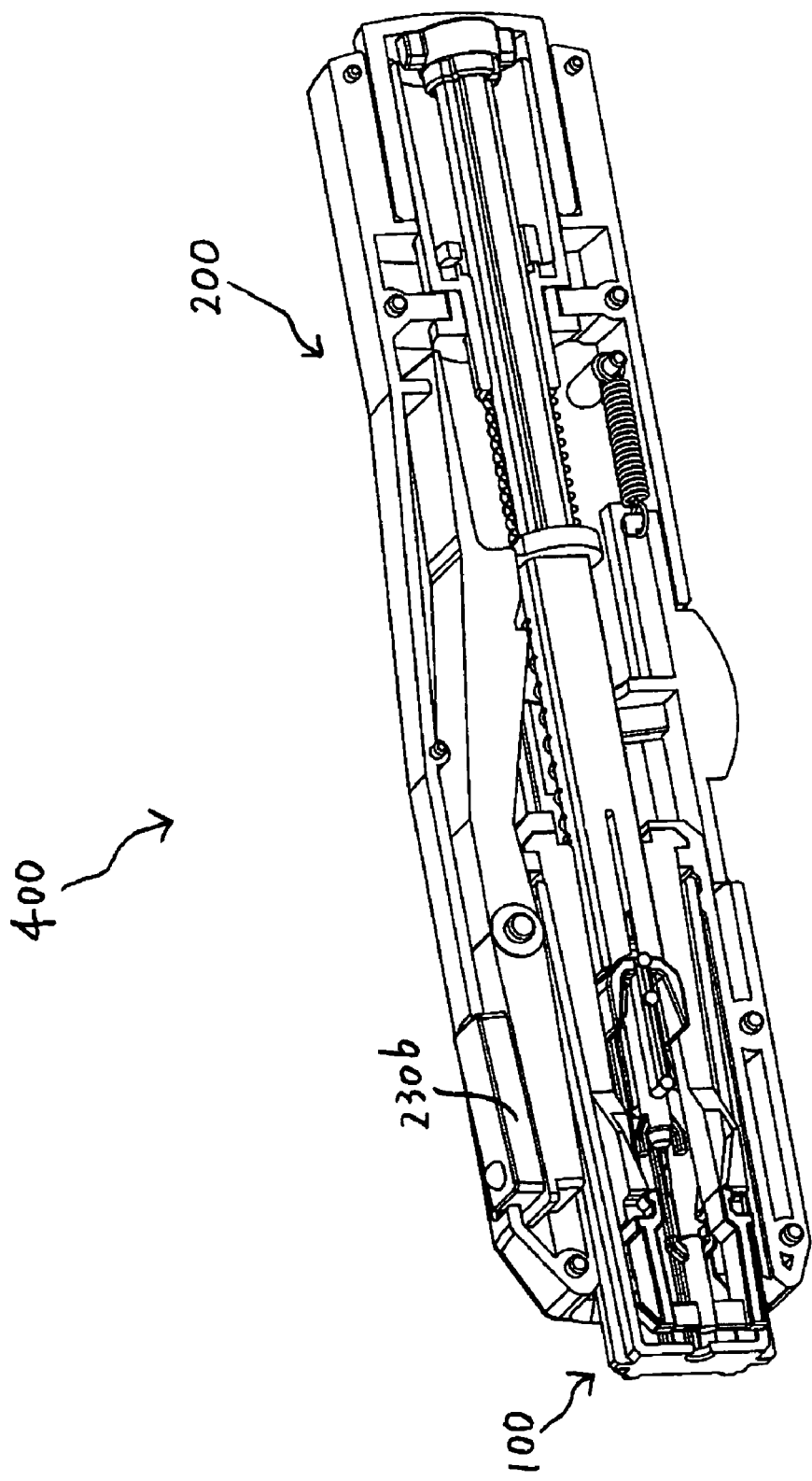
FIG. 18(b) is a schematic perspective view (type A) of the state at the point when the trigger lever is pressed to carry out the pricking.

The pricking is performed as follows: the pricking opening 105 is applied to a predetermined region to be pricked (for example, a finger tip). Subsequently, the front portion (indicated by reference numeral 230b in FIG. 17(a) and FIG. 17(b)) of the trigger lever 230 is pressed toward the inside of the injector 200 so as to cease the engagement between the rear stepped portion 230a of the trigger lever and the flange 204b of the plunger 204. This results in an instantaneous expansion of the compressed spring 205a, and thereby the lancet body 151 is launched in the pricking direction. FIG. 18(a) and FIG. 18(b) show the state immediately after the front portion 230b of the trigger lever 230 is pressed toward the inside of the injector 200.

In the course of the launching of the lancet body 151, the pair of second wing parts 159 (see FIG. 24(b)), which has been accommodated in the bow-shaped groove 206d of the lancet cap removing part 206, moves forward along the bow-shaped groove 206d in the pricking direction. Due to the groove 206d, the pair of second wing parts 159 can move forward without being expanded toward the outside, which enables the pair of second wing parts 159 to move forward without touching or hitting the stopper surface 180. In other words, the lancet cap removing part 206, which has been inserted into the lancet holder 102, serves to block the stopper surface 180 (more particularly, the edge of the lancet cap removing part 206 is in contact with the stopper surface 180), and thereby the pair of second wing parts 159, upon pricking, can move forward without touching or hitting the stopper surface 180. Therefore, the lancet body 151 can move forward without being obstructed by the second wing parts 159. This means that the tip 153a of the pricking component 153 can protrude from the pricking opening 105 to prick the predetermined region, as shown in FIG. 19(a) and FIG. 19(b).

Figure 19A:
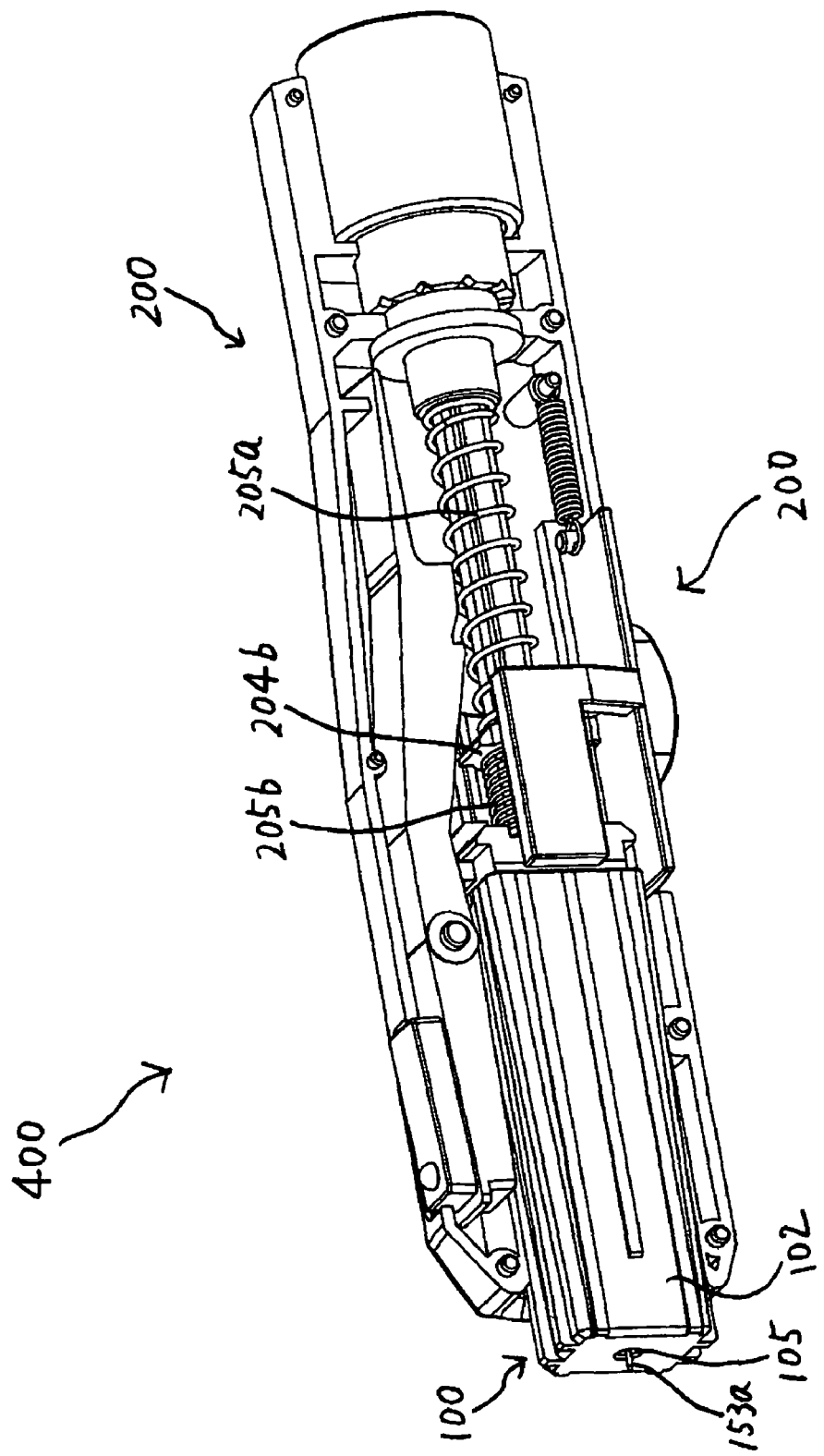
FIG. 19(a) is a schematic perspective view (type A), showing the pricking process wherein the tip of the pricking component is protruding from the pricking opening.
Figure 19:
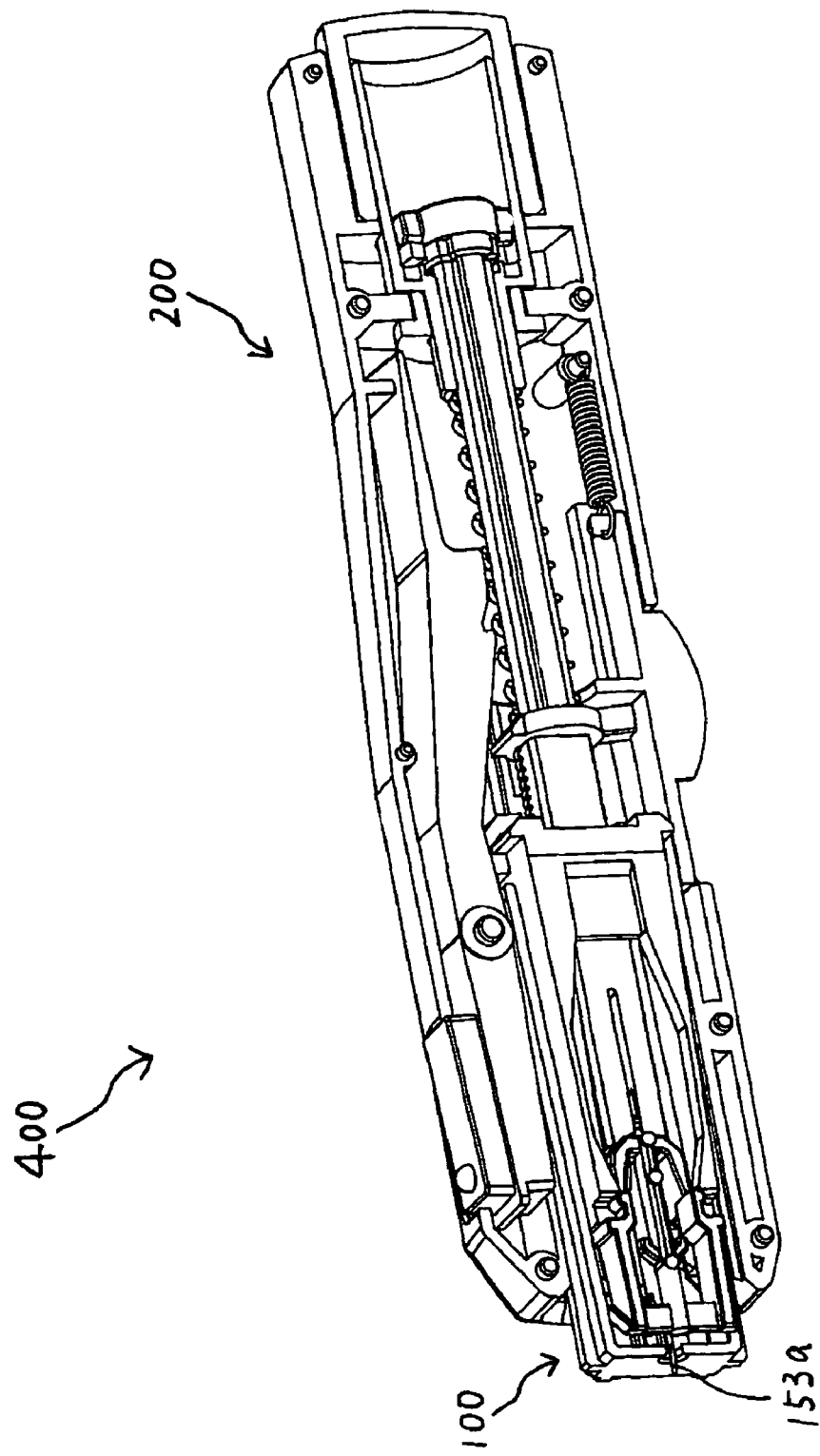
FIG. 19(b) is a schematic perspective view (type A), showing the pricking process wherein the tip of the pricking component is protruding from the pricking opening.
Figure 20:
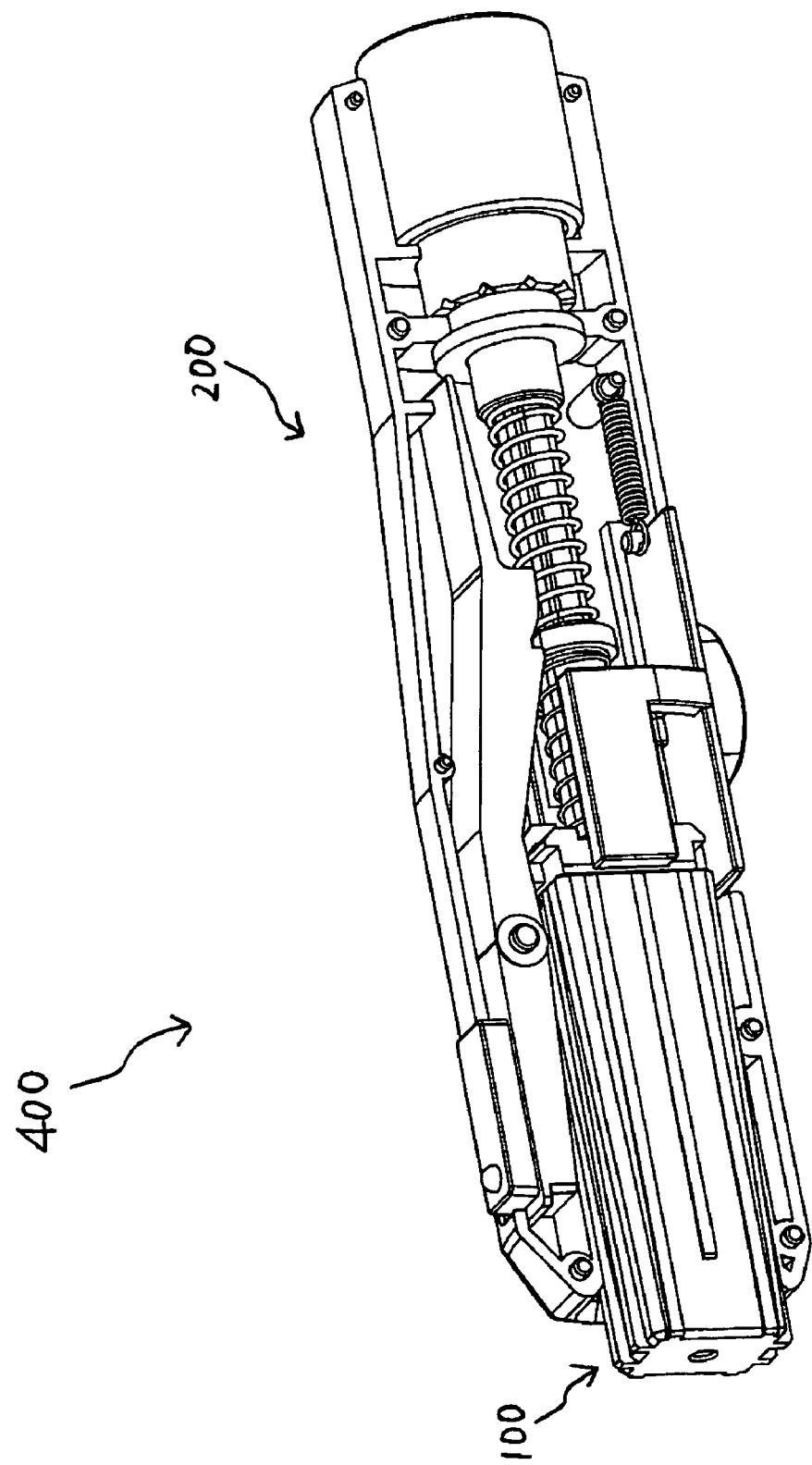
FIG. 20(a) is a schematic perspective view (type A) of the state after pricking.
FIG. 20(b) is a schematic perspective view (type A) of the state after pricking.
Figure 20B:
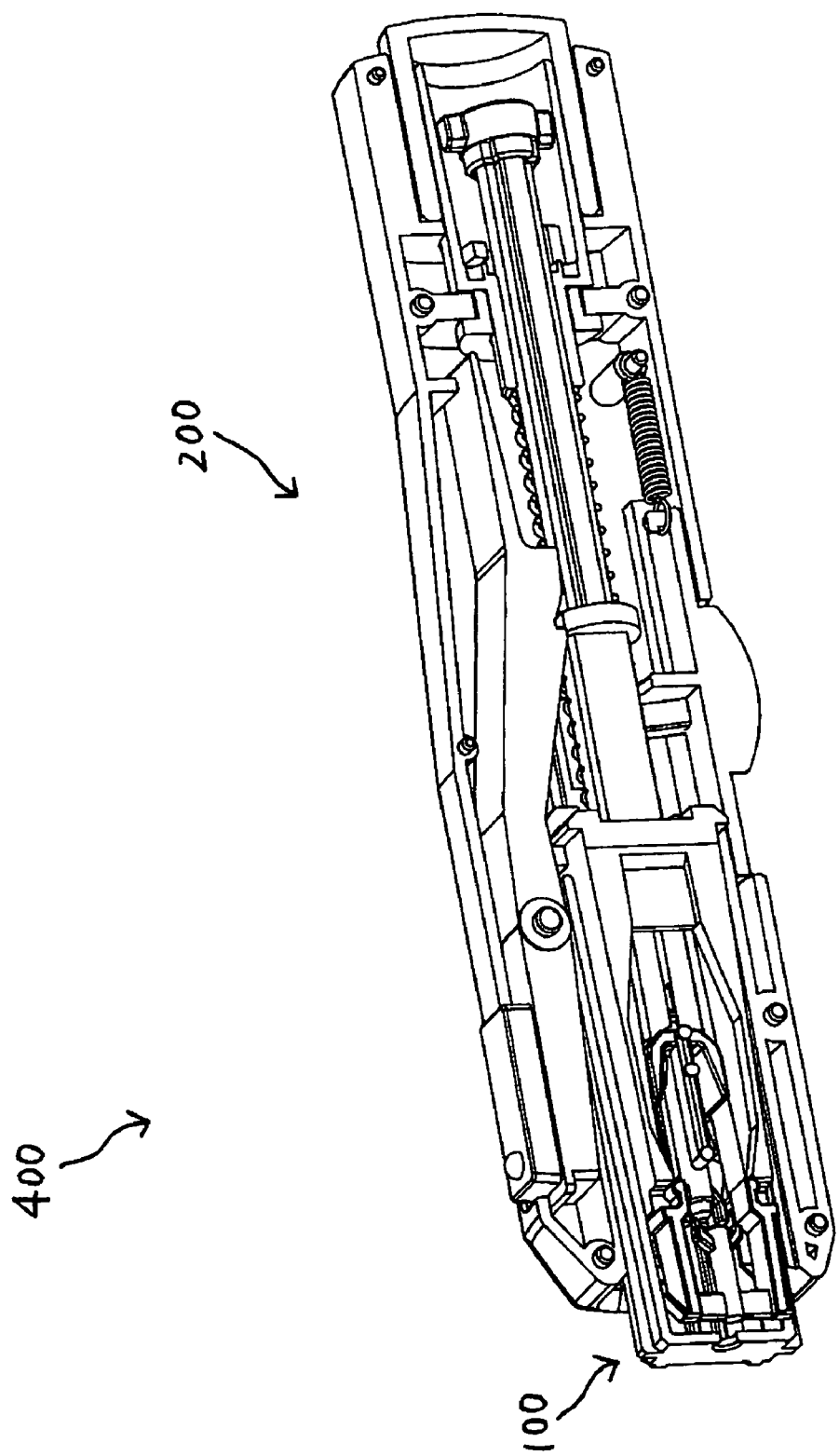

Upon pricking, the release spring 205a expands to the maximum whereas the return spring 205b is compressed, as shown in FIG. 19(a). After pricking, therefore, the release spring 205a attempts to returns to its original shape whereas the compressed return spring 205b serves to press the flange 204b of the plunger 204 to returns to its original shape. This causes the lancet body 151 (hence the pricking component 153) to be retracted quickly. The state after pricking is shown in FIG. 20(a) and FIG. 20(b).

Figure 21:
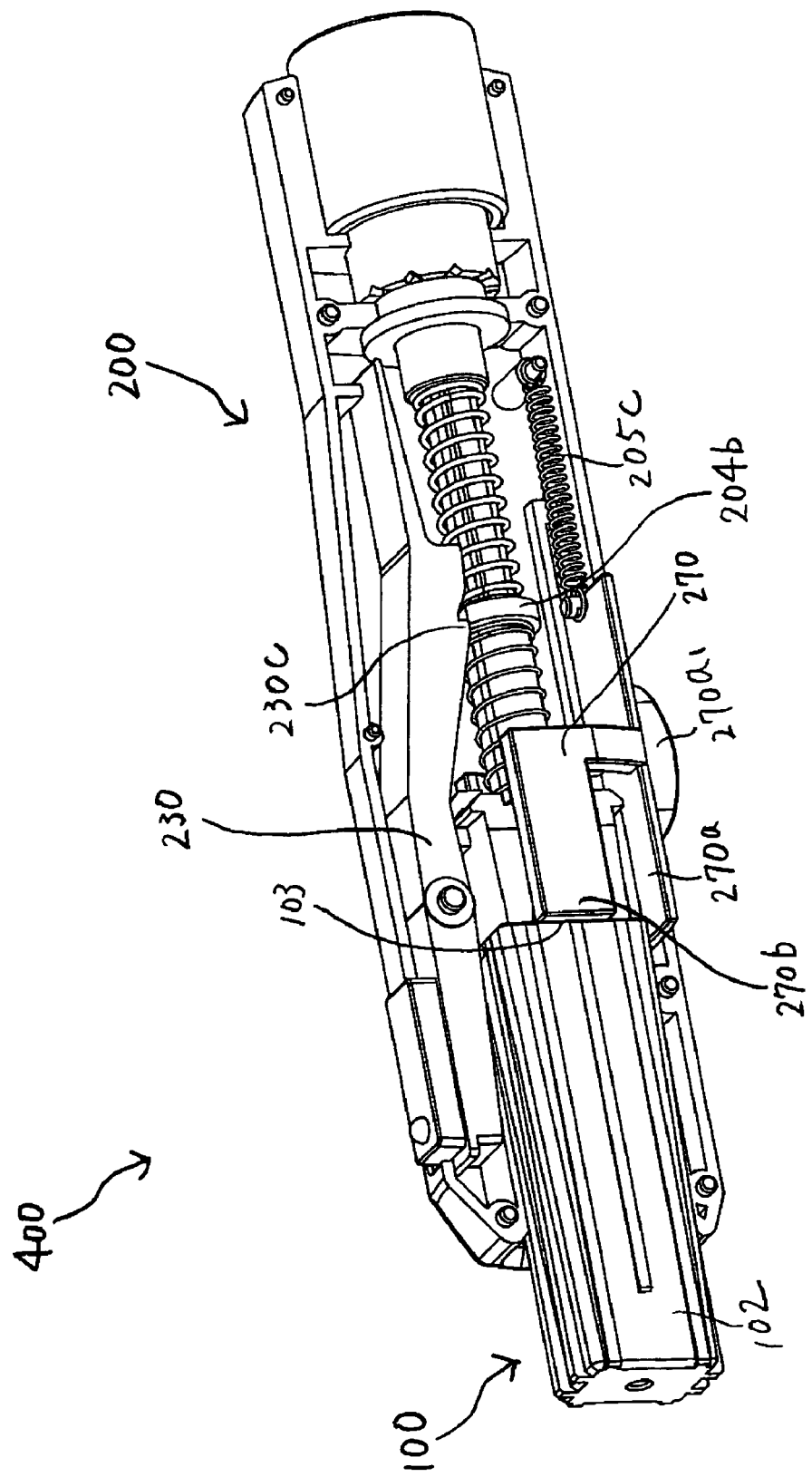
FIG. 21(a) is a schematic perspective view (type A) of the state after pricking, especially showing the state around the time when discharging of the lancet assembly from the injector is commenced by the ejector.
FIG. 21(b) is a schematic perspective view (type A) of the state after pricking, especially showing the state around the time when discharging of the lancet assembly from the injector is commenced by the ejector.
Figure 21:
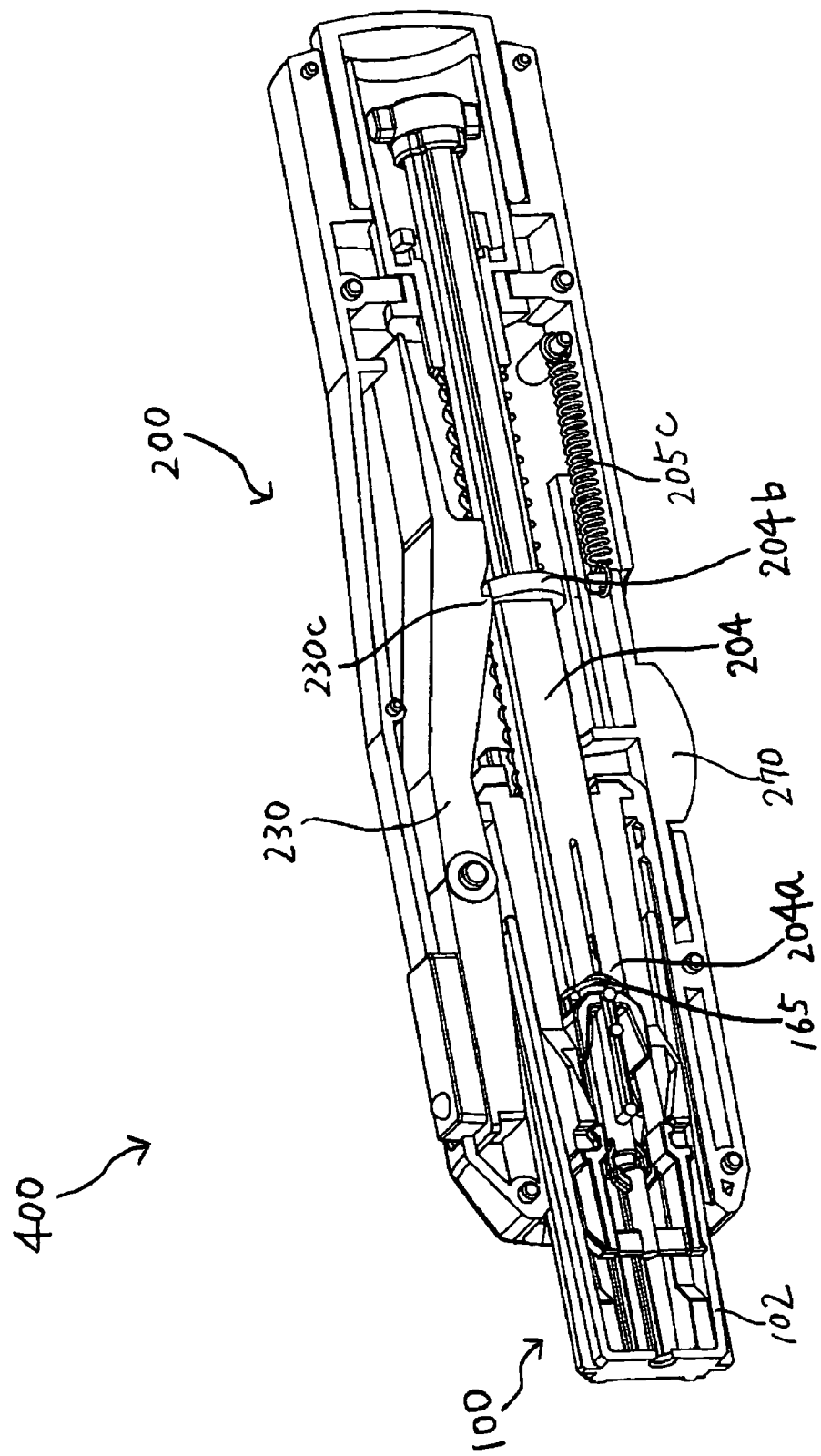
Figure 22A:
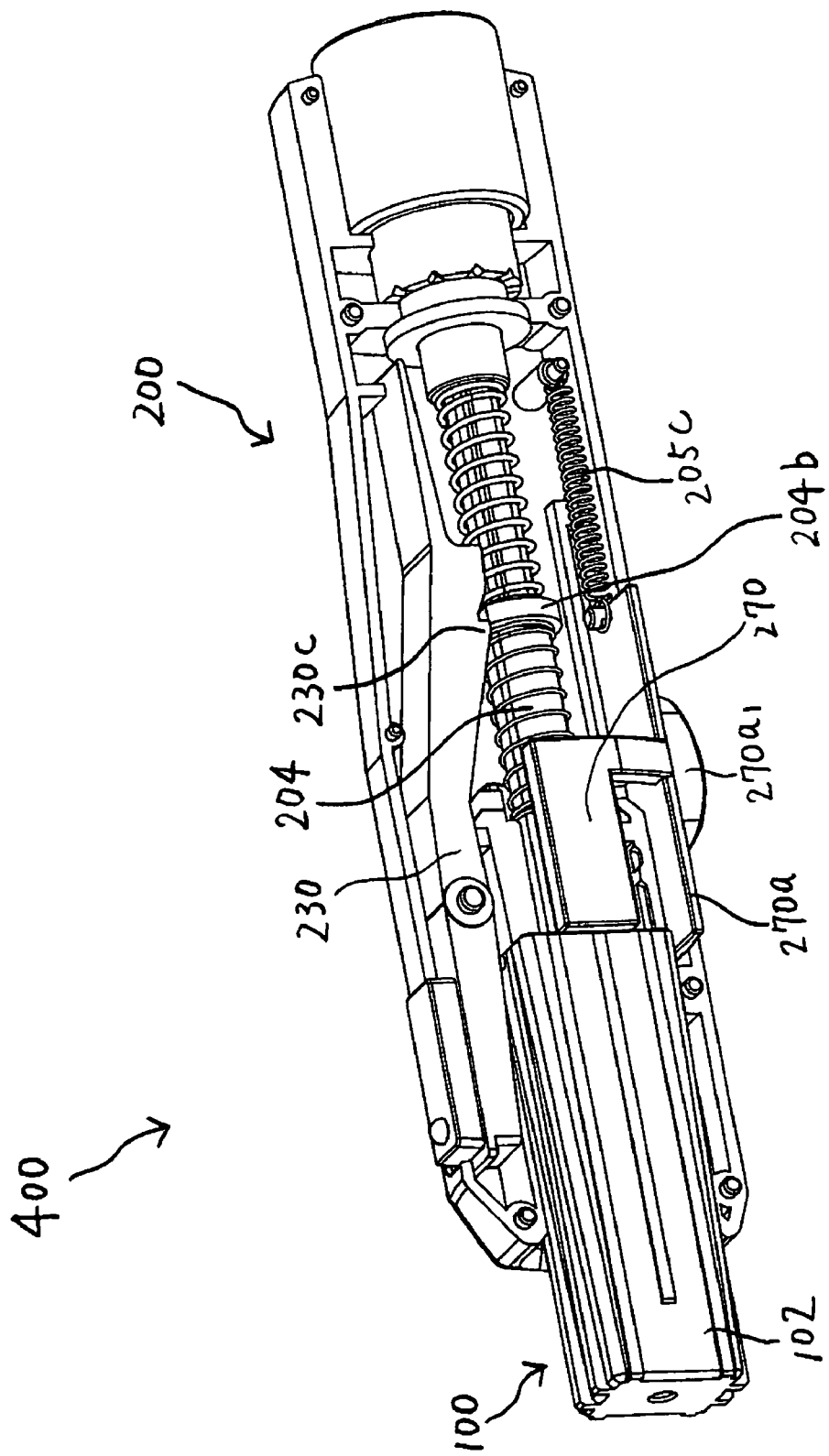
FIG. 22(a) is a schematic perspective view (type A) of the state after pricking, especially showing that the lancet holder is being discharged by the ejector.
Figure 22B:
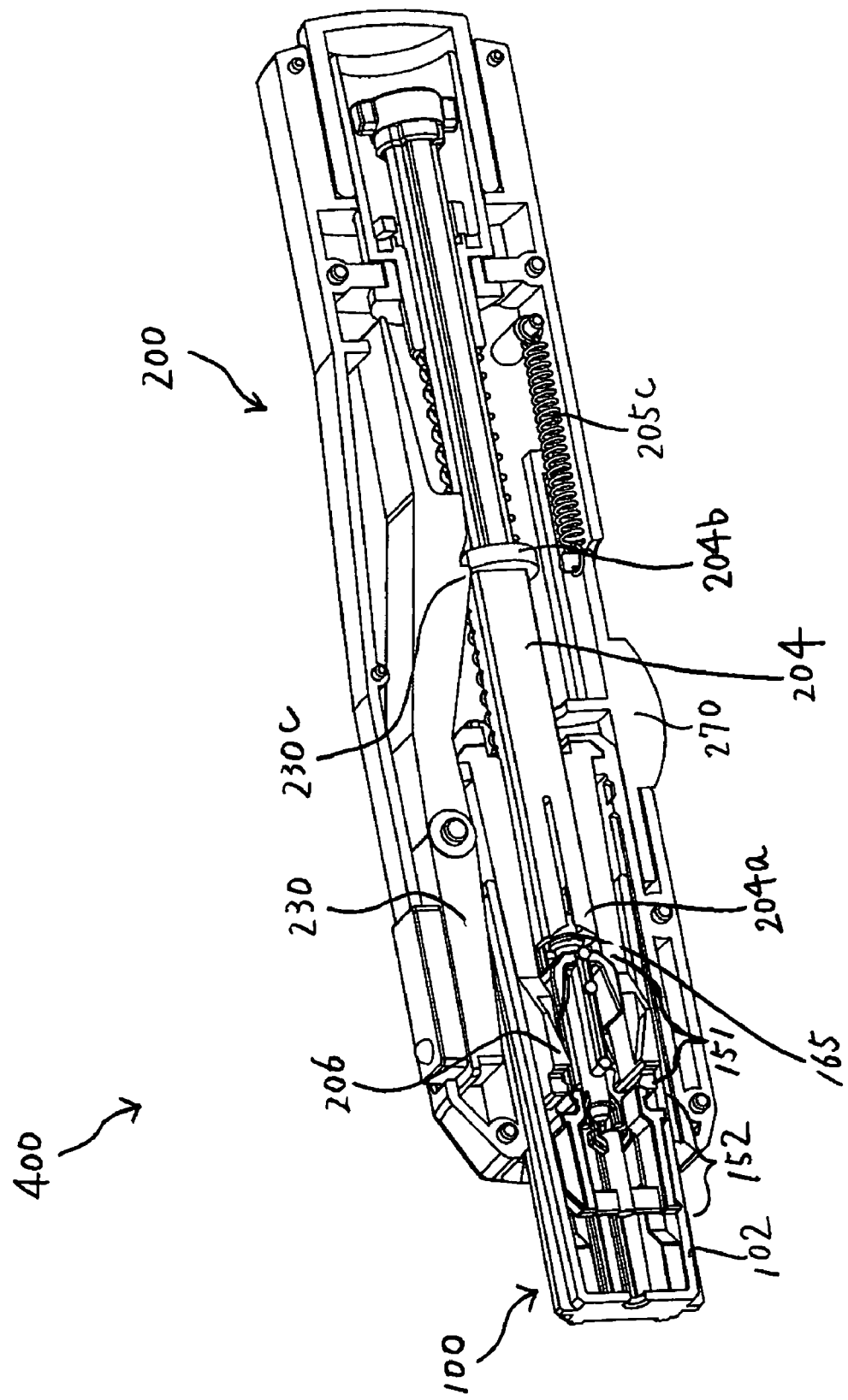
FIG. 22(b) is a schematic perspective view (type A) of the state after pricking, especially showing that the lancet holder is being discharged by the ejector.
Figure 23A:
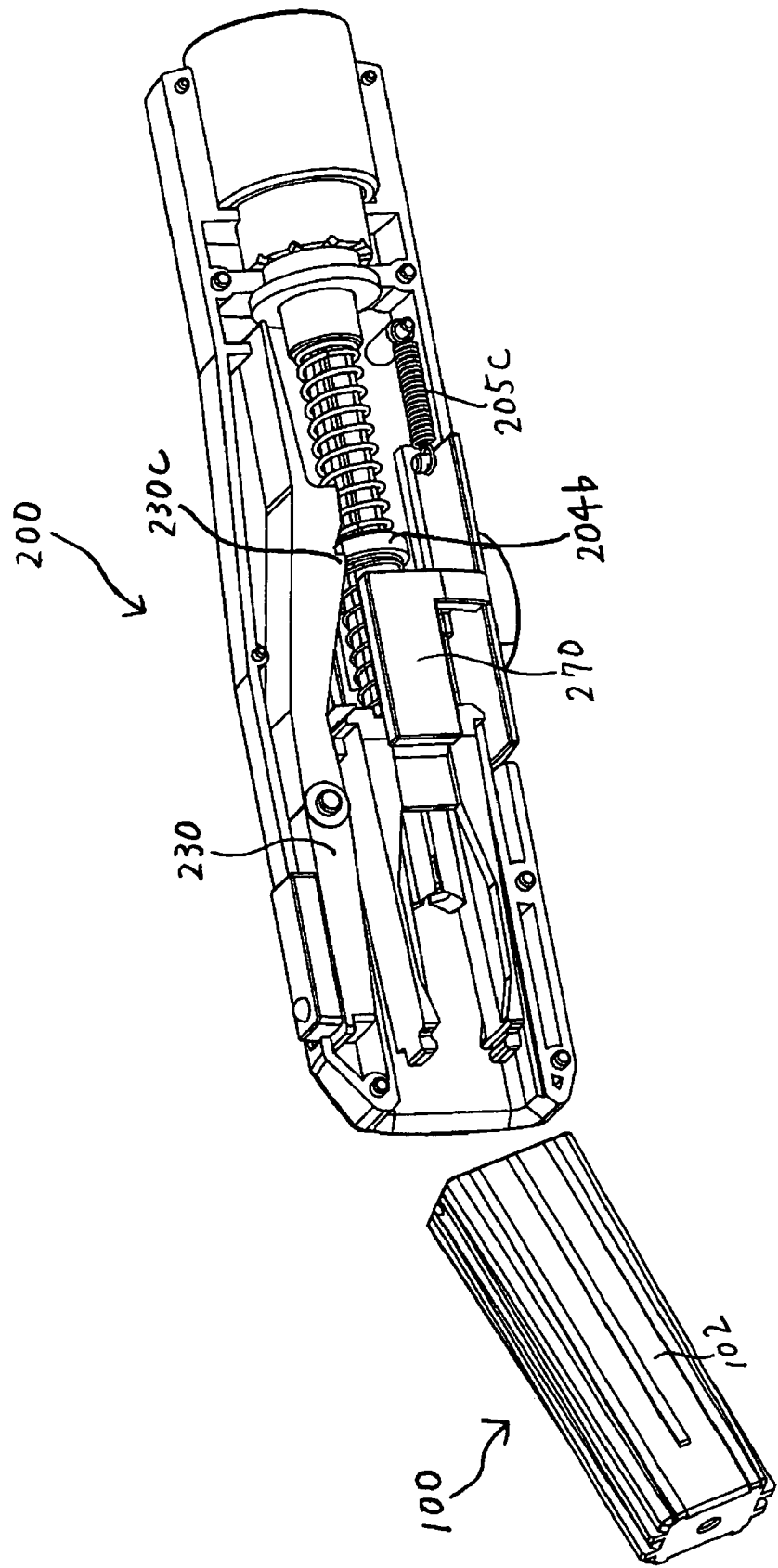
FIG. 23(a) is a schematic perspective view (type A) of the state where the lancet assembly has been completely discharged from the injector.
Figure 23:
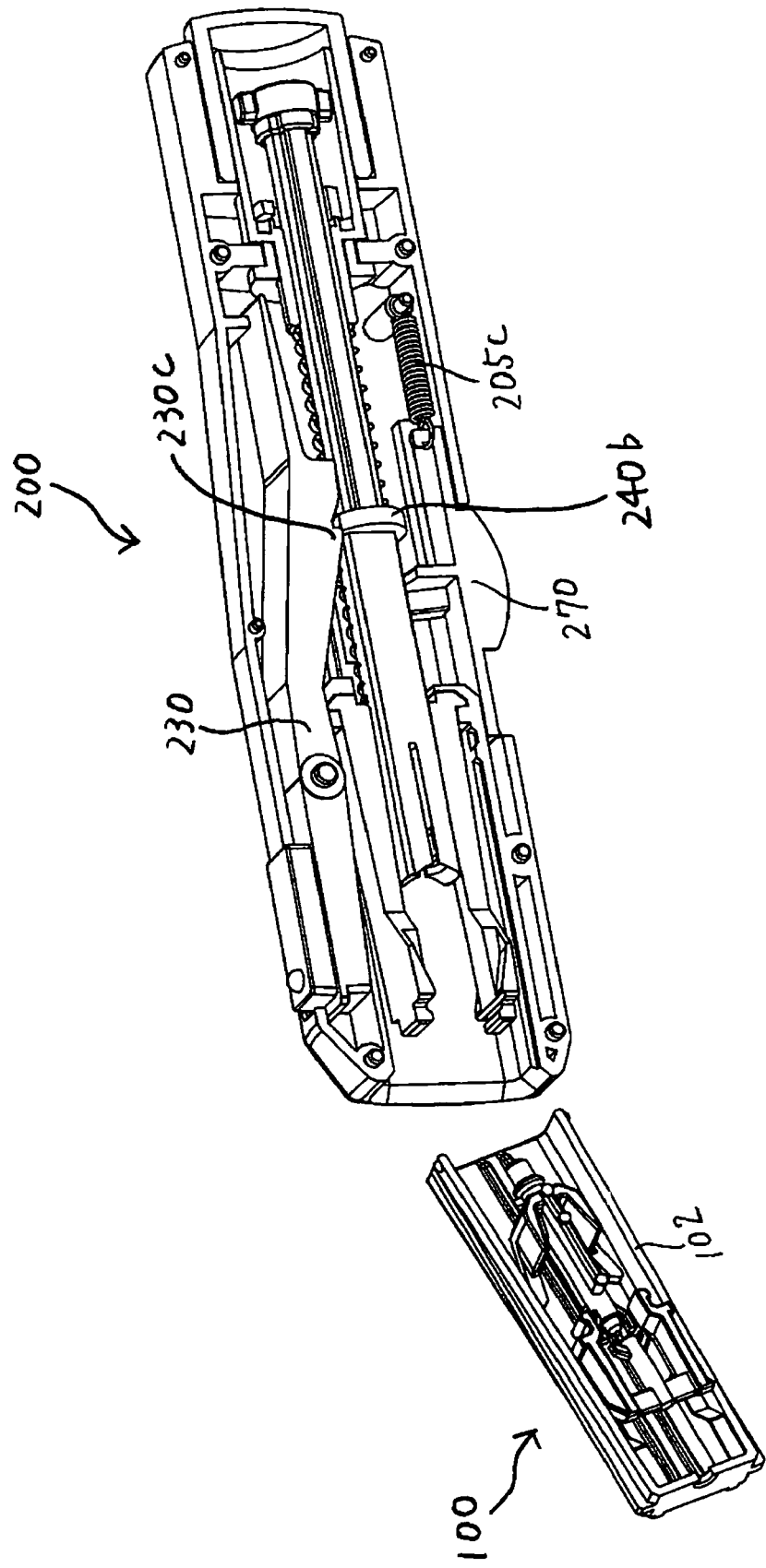
FIG. 23(b) is a schematic perspective view (type A) of the state where the lancet assembly has been completely discharged from the injector.

To remove (or discharge) the lancet holder 102 (more particularly the spent lancet assembly 100) from the injector 200 after pricking, the ejector 270 of the injector 200 is used. Specifically, the part $270a_1$ of the sliding portion 270a provided in the ejector 270 is pressed with a finger or the like so that the ejector slides forward. This causes the front portion 270b of the ejector 270 to press the edge of the opening end 103 of the lancet holder 102 so that the lancet holder 102 is discharged from the injector 200. The removing operation is shown sequentially in FIG. 21 to FIG. 23. FIG. 21(a) and FIG. 21(b) show the initial state where the lancet holder 102 is pressed by the ejector 270. FIG. 22(a) and FIG. 22(b) show the intermediate state where the lancet holder 102 is being pressed by the ejector 270, indicating that the lancet cap 152 and the lancet cap removing part 206 are no longer in engagement. FIG. 22(a) and FIG. 22(b) also show the state immediately before the engagement between rear end portion 165 of the lancet body 151 and front end 204a of the plunger 204 is released (see particularly FIG. 22(b)). FIG. 23(a) and FIG. 23(b) show the state where the lancet holder 102 has been completely removed from the injector 200.

Upon discharging the lancet holder 102, the rear end portion 165 of the lancet body 151 and the front end 204a of the plunger 204 no longer engage with each other as follows:

After pricking, the lancet holder 102 and the lancet body 151 are able to move back and forth relatively to each other. Therefore, when the lancet holder 102 is pressed forward by the ejector 270 so that the lancet holder 102 moves forward, the lancet body 151 moves backward within the lancet holder 102. As a result, the protrusion A 158 of the lancet body 151 makes contact with the protrusion B 108 of the lancet holder 102, and thereby the lancet body 151 is forced to move forward due to the movement of the lancet holder 102. As the lancet body 151 is forced to move forward, the plunger 204 that is in engagement with lancet body 151 is also forced to move forward. However, since the flange 204b of the plunger 204 is still in engagement with the engagement portion 230c of the trigger lever 230 (see FIG. 21 to FIG. 23), the plunger 204 is unable to move forward. That is, the lancet body 151 receives the force causing it to move forward, whereas the plunger 204 receives the force resisting it. As a result, there is generated the force causing the lancet body 151 and the plunger 204 to depart from each other, and thereby the rear end portion 165 of the lancet body 151 is finally separated from the end portion 204a of the plunger 204.

As will be understood by making reference to FIG. 22(b) and FIG. 23(b), the ejector 270 has an ejector spring 205c. Therefore, after the discharging of the lancet holder 102 is completed, the ejector 270 can be returned to its original position by releasing the finger from the ejector 270.

In the lancet holder 102 which has been removed, the separated lancet cap 152 and the lancet body 151 with the tip of the pricking component 153 exposed are contained. After the lancet holder 102 is discharged from the injector 200, the pair of second wing parts 159 is able to make contact with or hit the stopper surface 180 provided in the lancet holder 102 (see FIG. 6). Therefore, the tip of the pricking component 153 will not protrude from the pricking opening 105 due to the restriction of the movement of the lancet body 153 in the pricking direction. As will be seen from FIG. 6, the rear end face of the slope component 170 provided in the lancet holder 102 serves as the stopper surface 180 (most clearly shown in FIG. 1B). In this way, the protruding of the tip of the pricking component 153 from the pricking opening 105 is prevented, and thus the spent lancet assembly 100 can be safely disposed of.

With reference to FIG. 13(b), the pricking depth adjusting mechanism 300 will now be described. The pricking depth adjusting mechanism 300 is provided on the rear portion 204c of the plunger 204. The pricking depth adjusting mechanism 300 comprises a protrusion 310 that is provided on the rear edge and protrudes toward the outside, and a cylindrical component (i.e. ring-shaped component) 320 with graduated steps 325 (325a, 325b, 325c, . . . ) of various heights on its end, as shown in FIG. 13(b).

The protrusion 310 is preferably provided by attaching a protruding cap 305 as shown in FIG. 13(b) on the rear end of the plunger 204.

In the pricking depth adjusting mechanism 300, when the plunger 204 moves forward for pricking, the protrusion 310 of the plunger moves as indicated by arrow b to eventually hit the step 325 (specifically step 325a in the FIG. 13(b)) of the cylindrical component 320, and thereby the plunger 204 no longer moves further forward. Therefore, the distance over which the plunger 204 can move forward upon pricking can be changed, by rotating the cylindrical component 320 about its center axis and thereby switching the step which the protrusion 310 hits from the step 325 to other steps 325 with different heights. In this way, the depth of pricking can be changed. It is preferable that the steps 325 of the cylindrical component 320 are formed in a point-symmetrical configuration with respect to the center axis thereof, so that the pair of protrusions 310a and 310b can hit the steps 325 with the same height as shown in FIG. 13(b). It is also preferable that the cylindrical component 320 has an inner drum 340 and an outer drum 350 that are capable of rotating together, as shown below in FIG. 13(b). In this case, the cylindrical component 320 can be rotated indirectly by rotating the outer drum 350 with fingers. The injector housing 201 preferably has a window (i.e. opening) for allowing access to the outer drum 350 from the side of the injector 200.

In a preferred embodiment of the lancet assembly 100 according to the present invention, the small pricking opening 105 is provided so that the same pricking depth is achieved, irrespective of the force for applying the device to the body. The pricking opening 105 is preferably in the range from 0.5 to 2.0 mm in diameter. As a result, the pricking device of the present invention makes it possible to perform pricking to a depth set by the pricking depth adjusting mechanism 300. In other words, the pricking device of the present invention has such a configuration that the depth set by the pricking depth adjusting mechanism 300 is less likely to be influenced by the force for applying the device to the pricking point since the pricking opening has a small diameter of from 0.5 to 2.0 mm.

[Lancet Assembly and Injector of Type B]

The Lancet assembly and injector of Type B will now be described with reference to FIGS. 25 to 40. In the description of type B, similarly to the case of type A, "forward" substantially means the pricking direction in which the lancet moves for pricking (namely, the direction in which the pricking component moves for pricking), and "backward" substantially means the direction opposite to "forward". These directions as well as "upward" and "downward" are indicated in FIG. 26.

Figure 25:
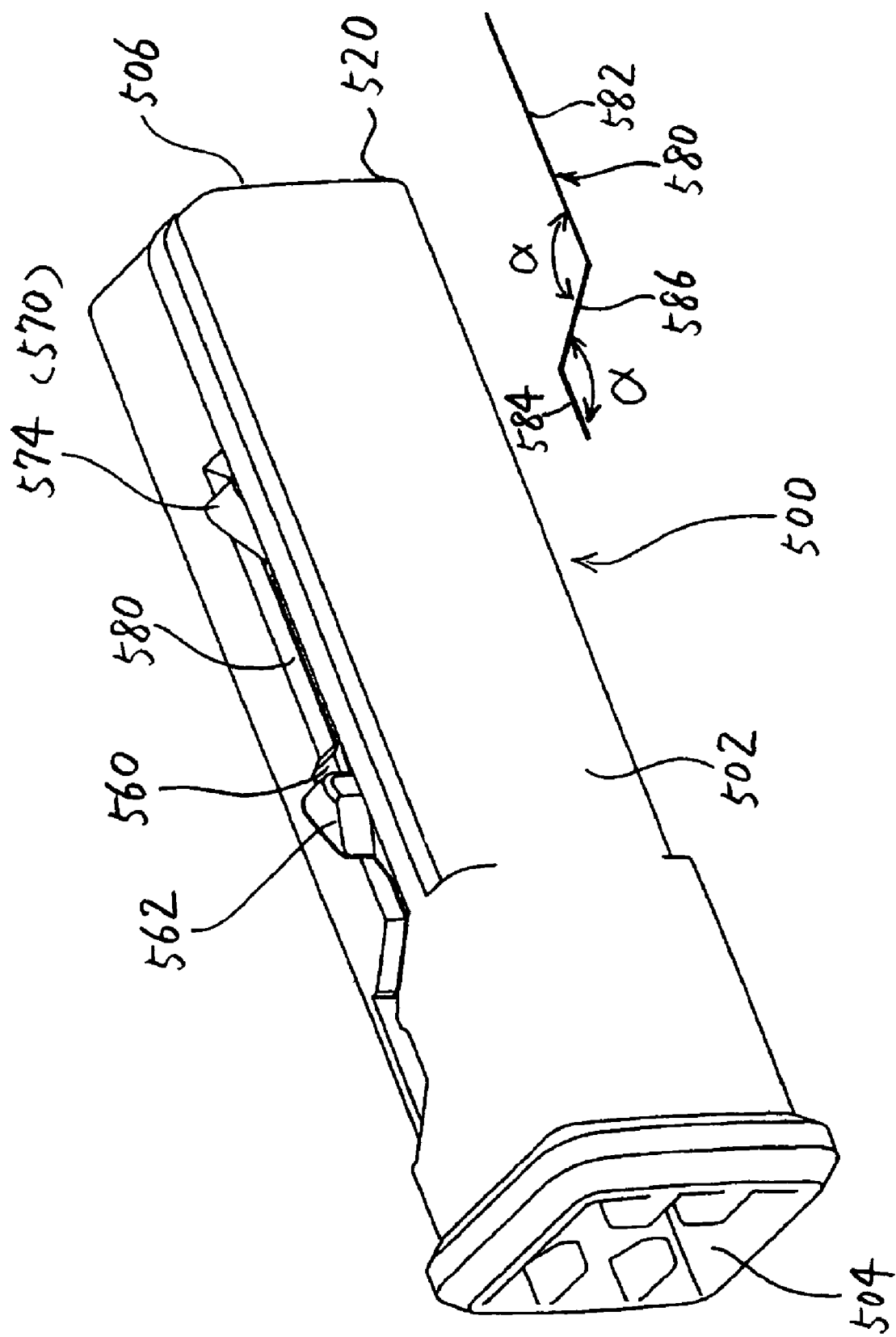
FIG. 25 is a schematic perspective view of the lancet assembly of type B according to the present invention.

The schematic perspective view of the lancet assembly 500 of Type B according to the present invention is illustrated in FIG. 25. It is shown in FIG. 25 that the lancet 550 of type B shown in FIG. 26 is incorporated in the lancet holder 502 of type B. For example, the lancet holder 502 has, as a whole, a shape of square box or square tube. The lancet 550 is housed in such lancet holder 502.

The lancet holder 502 has openings on both ends. A pricking opening 504 of the lancet holder 502, as shown in FIG. 25, is applied to a region to be pricked (for example, a finger tip). The lancet assembly 500 is provided by inserting the lancet 550 through the opening 506 (not shown in FIG. 25) into the lancet holder 502. The pricking opening 504 is located at the front end of the lancet holder 502, whereas the opening 506 is located at the rear end of the lancet holder 502. The lancet assembly 500 is loaded into the injector by inserting the lancet holder into the injector. In this case, the rear end 506 of the lancet holder firstly passes through the front end opening of the injector, similarly to the case of type A.

Figure 26:
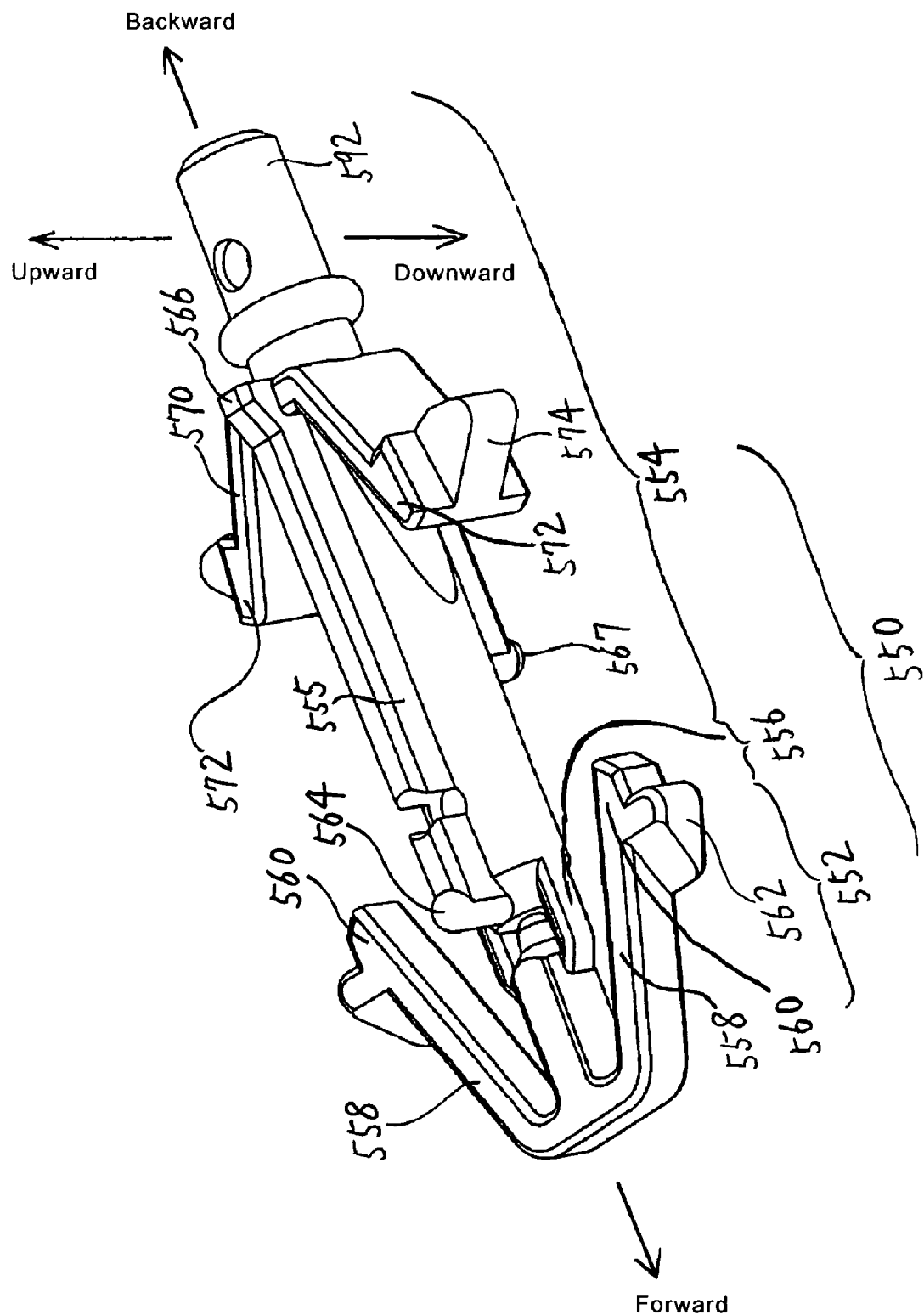
FIG. 26 is a schematic perspective view of a lancet of type B to be housed in lancet holder 502.

The schematic perspective view of the lancet 550 of type B is illustrated in FIG. 26. The lancet 550 comprises a lancet cap 552, a lancet body 554 and a bridging component 556 that interconnects the lancet cap and the lancet body wherein the pricking component is situated in both of the lancet cap and the lancet body. The tip of the pricking component (not shown in FIG. 26) is covered with the lancet cap 552. The lancet can be formed of resin (such as polyethylene or polypropylene) by inserting the pricking component (e.g. a needle) into a die, in the so-called insert molding process. There may be provided a notch in the bridging component 556.

The lancet cap 552 of type B has separator protrusions 558 extending in the sideward direction thereof. The separator protrusions 558 may extend sideways toward the outside from the axis of the lancet 550 (i.e. from the direction in which the pricking component extends). For example, the separator protrusions 558 may be in such an "arm" form that they protrude obliquely backward from the lancet cap as shown in FIG. 26. Upon loading the lancet assembly 500 into the injector, the edge portion 560 of the separator protrusion 558 or a portion near thereto makes contact with the wall surface that defines the front end opening of the injector. It is preferable that each of the separator protrusion 558 has a boss 562 formed near the edge portion 560 thereof. In this case, it is also preferable that the edge portion 560 and the boss 562 cooperate to accept therebetween a part of the wall surface adjacent to the front end opening of the injector, and thereby the edge portion 560 of the separator protrusion 558 and the wall surface of the injector surely make contact with each other (i.e. abut against each other).

Figure 29:
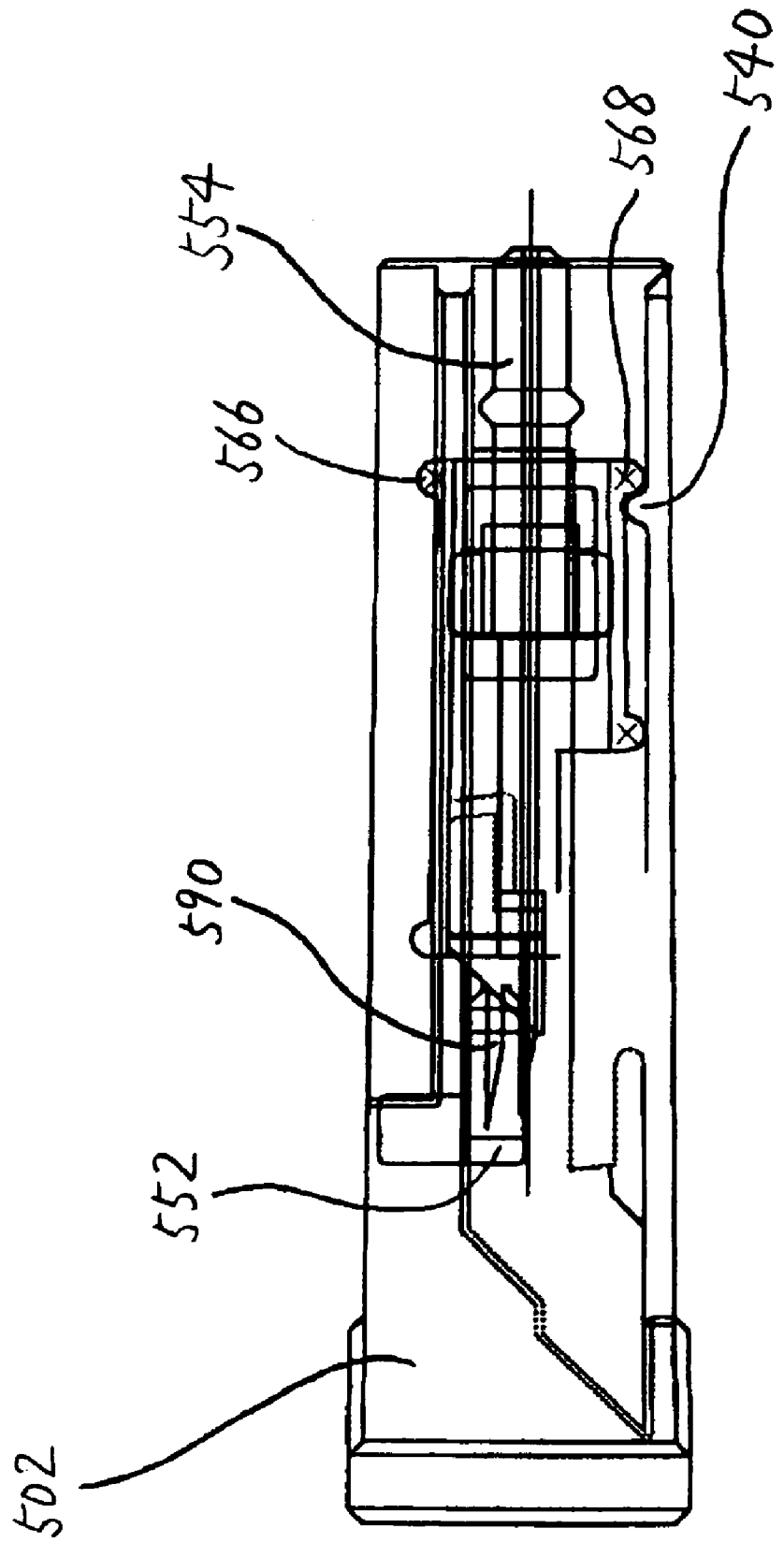
FIG. 29 is a schematic cutaway side view (type B) of the same state as that of FIG. 28.

It is preferable that a pair of guided components 555 of the lancet body 554 of type B have at least two protrusions A (e.g. two protrusions). In FIG. 26, only 564, 566 and 567 are shown, while there are other protrusions A, for example protrusion 568 located below the protrusion 566, similarly to 567 ("protrusion A 568" is shown in FIG. 29). The guided component 555 and the protrusions A slot into the guide channel (i.e. guide channel constituted from two rails 571 extending parallel to the pricking direction) on the inner surface of the lancet holder 502 so that the lancet body slides along the guide channel (two rails 571 are clearly shown in FIG. 32). The protrusions A enable the lancet body 554 to move reliably and smoothly in the pricking direction within the lancet holder 502. The protrusions A also contribute to (i) the securing of the lancet body to the lancet holder, (ii) the breaking of the bridging component and (iii) the prevention of the lancet body from coming off the lancet holder after use.

A protrusion B (indicated by 540 in FIG. 29) is provided in the guide channel, for example between two rails, near the rear end opening of the lancet holder. When the protrusion A on the lancet body moves forward between the rails and makes contact with the rear end of the protrusion B, the movement is stopped there, and thereby the lancet body is secured to the lancet holder. Upon the breaking of the bridging component, the protrusion A of the lancet body is prevented from moving further forward. However, when the force causing the protrusion A of the lancet body to move forward exceeds a predetermined threshold (for example, when the lancet holder is pressed further backward while the rear end of the plunger and the rear end of the injector body are still in contact with each other, as will be described later), the protrusion A can ride up and over the protrusion B to move forward.

The state as shown in FIG. 25 is one wherein (1) the lancet is disposed in the lancet holder with the separator protrusion 560 fitted in the elongated opening 580; (2) the protrusion A of the lancet body lies between the rails and behind the protrusion B; and (3) a boss 574 provided at the edge portion of stopper protrusion 570 is fitted in the elongated opening 580 ("stopper protrusion" and "elongated opening" will be described later in detail). The lancet 550 is attached to the lancet body such that the lancet is movable somewhat back and forth in the pricking direction between the state where the protrusion 570 of the lancet body makes contact with the rear edge of the elongated opening 580 and the state where the protrusion A makes contact with the protrusion B provided between the rails.

The lancet body 554 of type B has a pair of the stopper protrusions 570 extending in the sideward direction thereof. The stopper protrusions 570 may extend sideways toward the outside from the axis of the lancet body (i.e. the direction in which the pricking component extends). For example, the stopper protrusions 570 may be in such an "arm (i.e. stopper arm)" protruding obliquely forward from the lancet body, as shown in FIG. 26. After pricking, the edge 572 of the stopper protrusion 570 or a portion in the vicinity thereof can make contact with (i.e. abut on) stopper 596 or stopper component 596 (see FIG. 32) provided on the inner surface of the lancet holder, and thereby the lancet body is prevented from moving further forward so that the tip of the pricking component does not protrude from the pricking opening after pricking. In other words, after pricking, the tip of the pricking component is located sufficiently inward from the front end opening of the holder. It is preferable that each of the stopper protrusions 570 has a boss 574 near the edge 572 thereof. In this case, it is also preferable that the edge 572 and the boss 574 cooperate to surely make contact or surely engage the stopper protrusion and the stopper 596 of the lancet holder with each other.

The lancet assembly 500 has an elongated opening 580 on each of the opposed side faces thereof. A part of each separator protrusion 558 (particularly the edge portion or distal end 560 and/or the boss 562 provided thereon) protrudes through the elongated opening 580 as shown in FIG. 25. The edge 572 of each stopper protrusion 570 and/or the boss 574 provided thereon are/is just located within the elongated opening or protrude(s) a little toward the outside therefrom. As shown in the drawing, the separator protrusion 558 protrudes more than the stopper protrusion 570 does. As a result, the separator protrusion 558, not the stopper protrusion 570, can surely make contact with the front end of the injector.

As will be understood from FIG. 25, the rear portion 582 of the elongated opening 580 is included substantially within a plane that includes the separator protrusion 558 and the stopper protrusion 570, and extends parallel to the pricking direction. The front portion 584 of the elongated opening is away from the above plane and extends in a direction parallel to the pricking direction. In the elongated opening, there is an intermediate portion 586 disposed obliquely to interconnect the rear portion 582 and the front portion 584 (see the schematic diagram of the elongated opening in FIG. 25). As a result, the elongated opening 580 has a shape of letter Z as a whole (see FIG. 25). Although the letter Z generally bends with an acute angle (for example, $\alpha=45°$), the above shape according to the present invention bends with an obtuse angle (for example, $\alpha=135°$). The bended portion of the Z shape may be rounded. Also, the intermediate portion 586 and the front portion 584 may be curved or straight. In another embodiment, the front portion 584 may be omitted. It should be noted that the elongated opening 580 may not necessarily be formed in Z-letter shape, as long as the lancet cap can move forward to the point that is off the pricking pathway.

Figure 27:
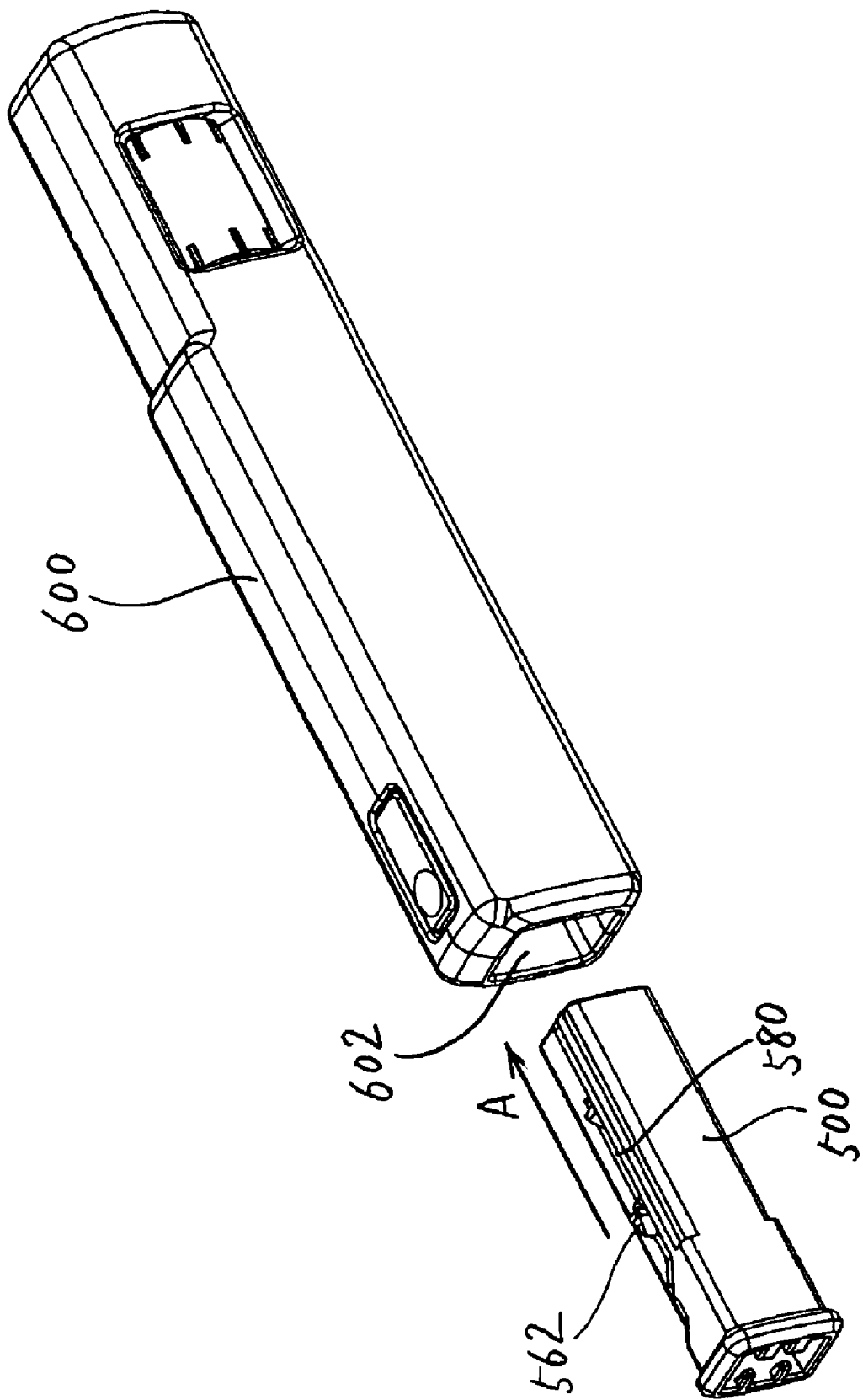
FIG. 27 is a schematic perspective view (type B), showing that the lancet assembly is inserted into an injector of the present invention through the front end opening of the injector.

The lancet assembly 500 of Type B shown in FIG. 25 is loaded by inserting the lancet assembly 500 backward (in the direction indicated by arrow A) through the front end opening 602 of the injector 600 of type B, as illustrated in the schematic perspective view of FIG. 27. The loading operation is carried out similarly to the case of type A. That is to say, the lancet assembly 500 is loaded by holding and then inserting the lancet assembly 500 with one hand into the front end opening 602 of the injector 600 of the type B held with other hand. The loading is complete when the lancet assembly cannot be inserted any more by the force exerted by an ordinary person.

Upon inserting the lancet assembly 500 through the front end opening 602, the rear end of the lancet body 554 makes contact with (i.e. abuts on) the plunger of the injector. As the insertion is continued, the plunger is retracted so that the spring provided around the plunger is compressed, and the lancet 550 moves, within the lancet holder 502, a little forward relative to lancet holder 502. Then, the separator protrusion 558 (specifically, rear side of the edge portion 560 or boss 562) makes contact with the front end surface 604 (which defines the front end opening 602) of the injector 600, specifically the edge of the front end opening 602. State of such contact is shown in schematic perspective view of FIG. 28 and in schematic cutaway side view of FIG. 29 (FIG. 29 is a view in the direction of arrow D in FIG. 28). As will be seen from FIG. 29, the protrusion A (568) of the lancet body is in contact with the rear side of the protrusion B (540) between the rails provided on the lancet holder, and thereby the lancet body is secured to the lancet holder.

When the lancet holder is inserted further into the injector while the protrusion A (568) and protrusion B (540) are still in contact, the lancet body is forced to move together with the lancet holder since the lancet body is secured to the lancet holder (in other words, the protrusion B (504) of the lancet holder presses the protrusion A (568) of the lancet body backward). On the other hand, the lancet cap which is not secured to the lancet holder is pressed by the edge of the front end opening of the injector (in other words, the lancet cap is pressed forward). As a result, the forces are generated in the lancet cap and the lancet body wherein the direction of the force in the lancet cap is opposite to the direction of the force in the lancet body. When such forces eventually exceed a predetermined threshold, the bridging component that interconnects the lancet cap and the lancet body is broken apart. The breaking of the bridging component causes the lancet cap 552 to be separated from the lancet body 554. When the lancet holder is inserted further, the separated lancet cap moves within the lancet holder 502 to deviate from the pricking pathway. This process will be described in more detail below with reference to FIG. 30 to FIG. 32.

Figure 28:
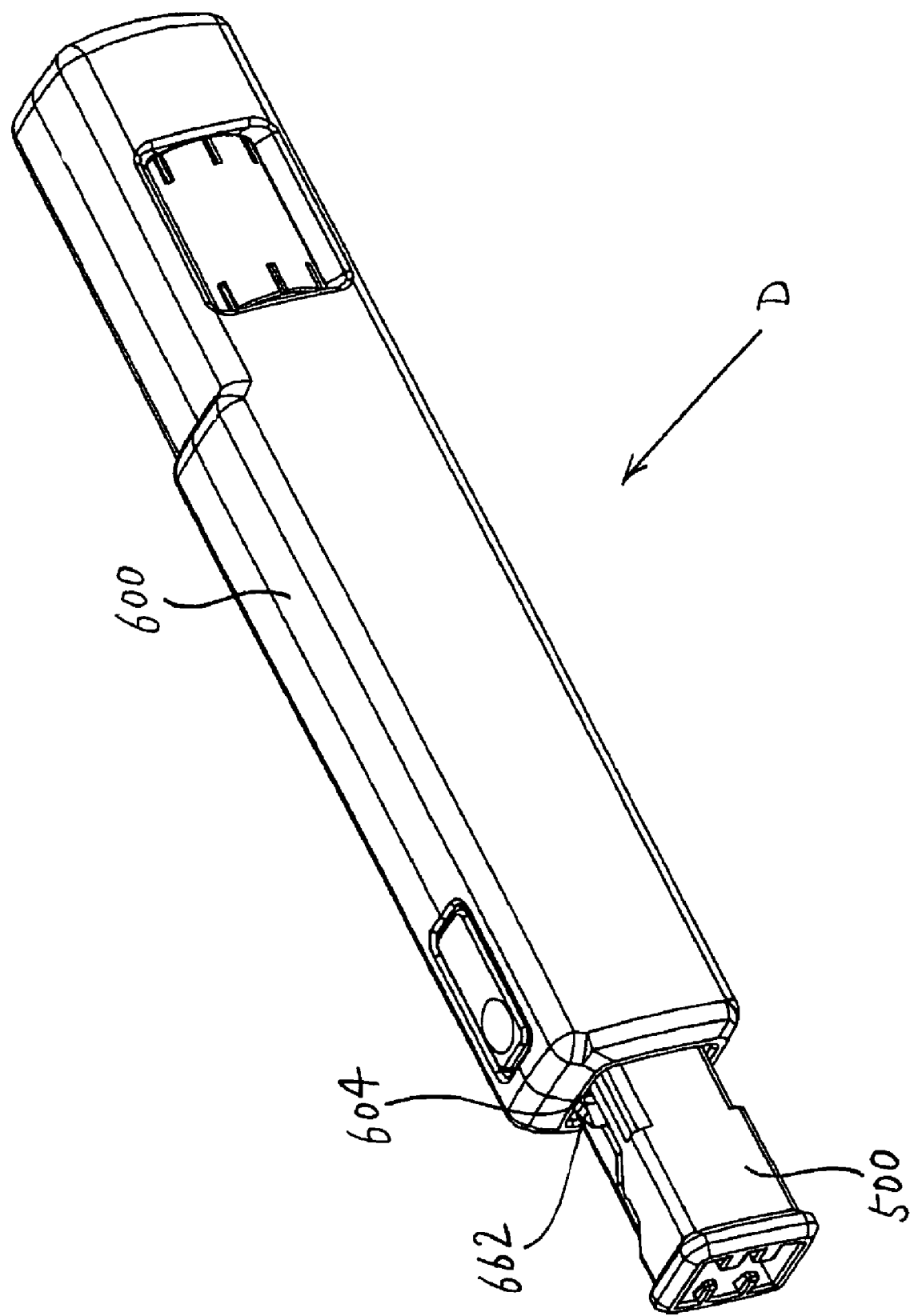
FIG. 28 is a schematic perspective view (type B), showing that the separator protrusion of the lancet is in contact with the front end portion of the injector upon the loading of the lancet assembly into the injector.
Figure 30:
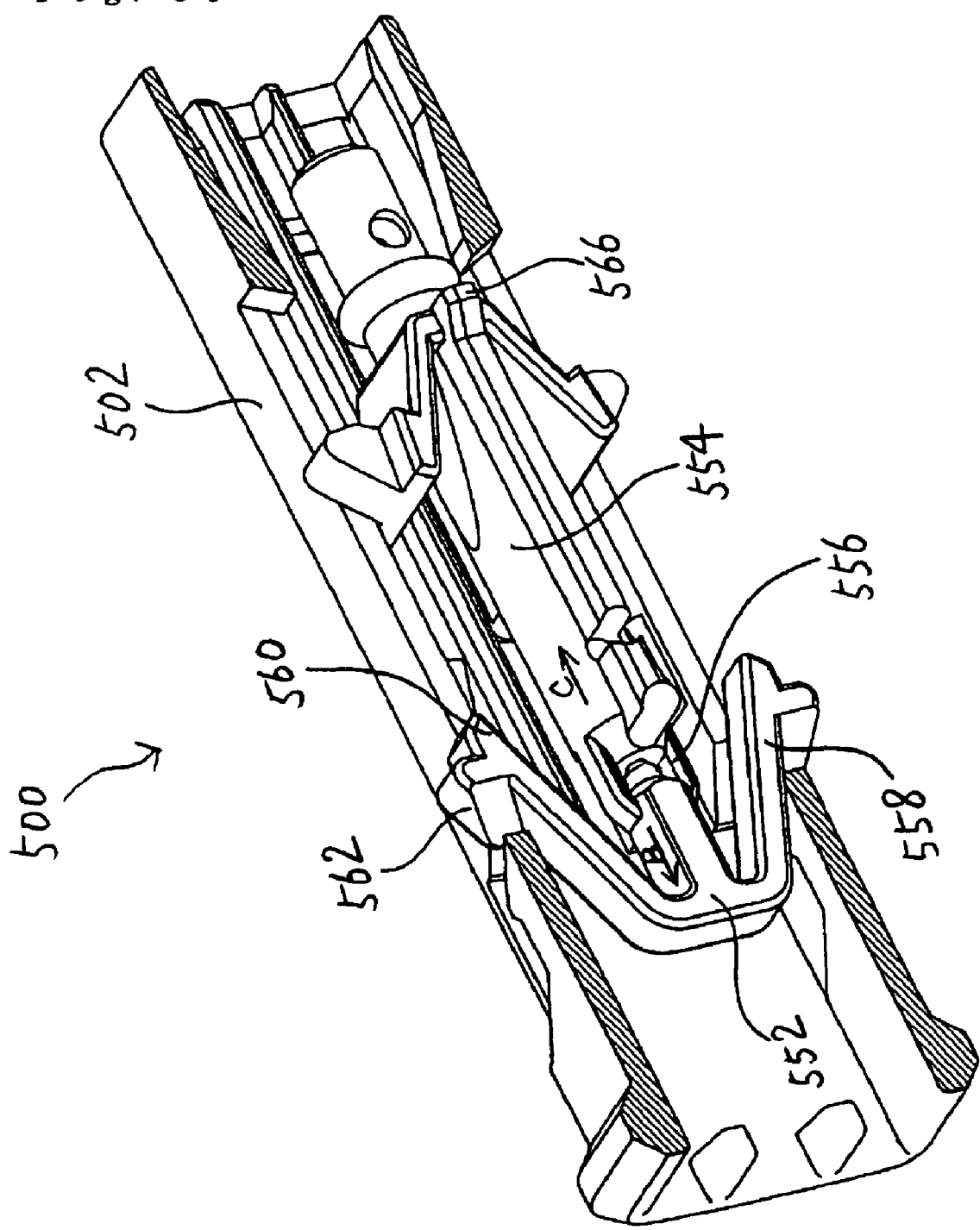
FIG. 30 is a schematic perspective view (type B), showing the lancet assembly of FIG. 28 or FIG. 29 (in which the separator protrusion of the lancet is in contact with the front end portion of the injector) with one half of the lancet holder on a near side cutaway to illustrate the inside.

FIG. 30 shows the lancet assembly 500 in the state of FIG. 28 or FIG. 29, with a half thereof on the foreground side cut away for the ease of understanding the inner structure of the lancet assembly 500. For the sake of simplicity, only the lancet assembly 500 is shown and other components that constitute the injector are not shown. The lancet assembly shown in FIG. 30 is in such a state where the edge 604 of the front end opening 602 of the injector (see FIG. 28) is in contact with the corner formed by the edge portion 560 of the separator protrusion 558 and the boss 562.

When the lancet assembly 500 is inserted from this state (namely, the lancet holder 502 is forced to move backward), the separator protrusion 558 cannot move further backward due to being in contact with the edge 604 of the front end opening 602. As a result, when the lancet holder 502 is forced to move further backward, the separator protrusion 558 (namely the lancet cap 552) receives the force causing it to be pressed forward by the edge 604 of the front end opening 602. Also, when the lancet holder 502 is forced to move further backward, the lancet body 554 connected with the lancet cap 552 receives the force causing the lancet body 554 to move forward, similarly to the separator protrusion 558. However, the lancet body 554 is prevented from moving forward since the protrusion A 568 of the lancet body 554 is in contact with the rear side of the protrusion B 540 disposed between the rails in the lancet holder 502. As a result, there are generated the forces acting in opposite directions (refer to arrow B and arrow C in FIG. 30) on frond and rear sides of the bridging component 556 that integrally connects the lancet cap 552 and the lancet body 554. When such forces exceed the breaking strength of the bridging component 556, the bridging component 556 is then broken apart.

After the bridging component 556 is broken, only the lancet cap 552 is pushed by the edge 604 of the front end opening 602 along the elongated opening 580, while the lancet body 554 remains in the state shown in FIG. 30.

In the state of the lancet assembly 500 shown in FIG. 25, the protrusion A(566) on one side of lancet body 554 and the protrusion A(568) on the other side of the lancet body 554 are located behind the protrusion B(540) between the rails on the inner surface of the lancet holder 502. Upon inserting the lancet holder 502, the protrusions A (566 and 568) of the lancet body cannot ride over the protrusion B and they are in contact with each other. This makes it possible to move the lancet body 554 backward while the lancet body 554 is secured to the lancet holder 502.

Figure 31:
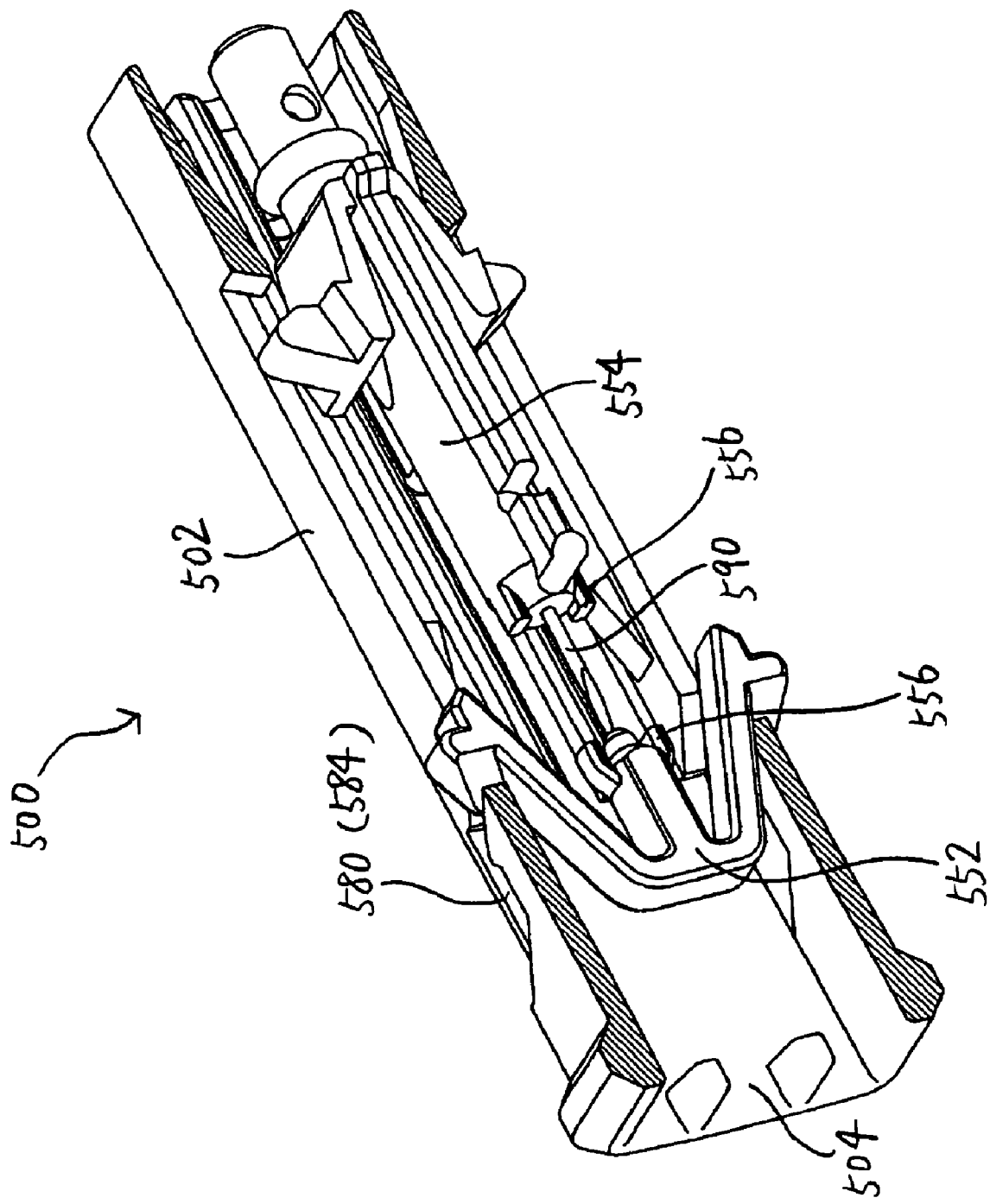
FIG. 31 is a schematic perspective view (type B) of the state (showing similarly to FIG. 30) where the lancet cap has been separated from the lancet body and thus the tip of the pricking component is exposed.
Figure 32:
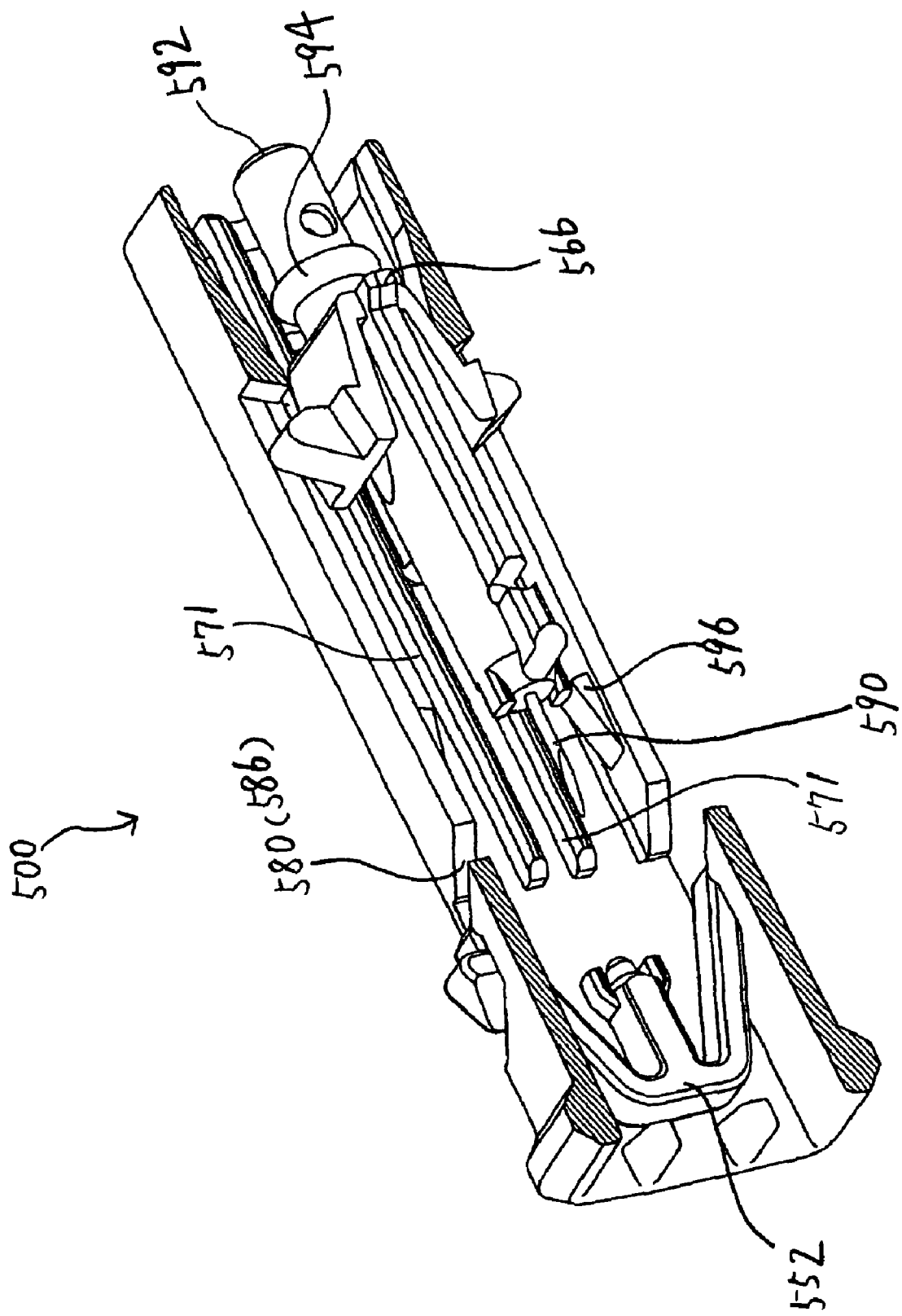
FIG. 32 is a schematic perspective view (type B) of the state (showing similarly to FIG. 30) where the lancet cap moves from the state shown in FIG. 31 through the front portion of the elongated opening to the front edge thereof and has stopped by making contact therewith.

When the bridging component 556 is broken and the lancet cap 552 is separated from the lancet body 554, the tip of the pricking component 590 is exposed, as shown in FIG. 31. Subsequently, as the insertion is continued, the separated lancet cap 552 moves from the front portion 584 of the elongated opening 580 to the front edge thereof. The movement of the lancet cap 552 is stopped at the front edge of the elongated opening 580 due to the contact therewith, as shown in FIG. 32. This state where the movement of the lancet cap 552 has stopped is also shown schematically in FIG. 33, similarly to FIG. 29. It should be noted that the separated lancet cap 552 is not on the pricking pathway of the lancet, namely the separated lancet cap 552 is located at the point off the pricking pathway. This is due to that the elongated opening is in a substantially Z-letter form as described above.

Figure 33:
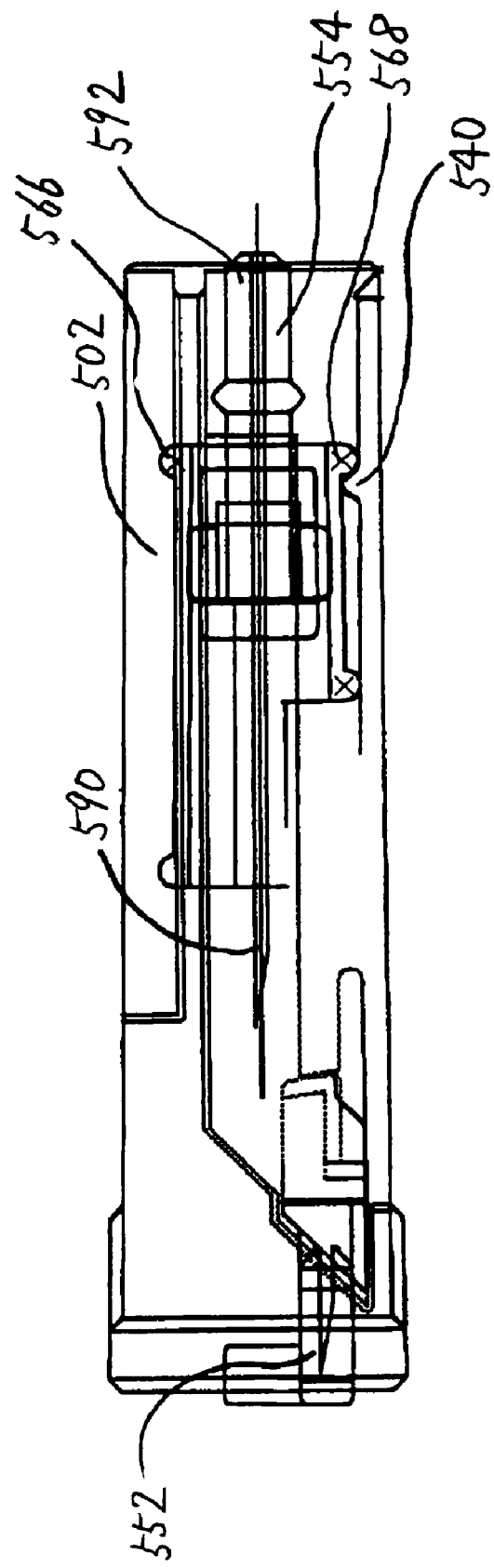
FIG. 33 is a schematic cutaway side view (type B) of the state of FIG. 32 (showing similarly to FIG. 29).

When the lancet holder 502 is inserted further from the state shown in FIG. 33, the plunger is pressed backward since the rear end 592 of the lancet body is in contact with the front end 702 of the plunger 700. On the intermediate portion 704 of the plunger disposed in the injector, there is provided the flange 706. Whereas, within the injector housing, the partition 709 is provided. A spring S1 (see FIG. 36) is provided around the plunger between the flange 706 and the partition 709.

When there is no external force acting on the plunger, the spring S1 acts so that the plunger is in a forward position.

When the lancet holder is further inserted, the rear end 592 of the lancet body acts against the force of the spring S1 to press the plunger backward relative to the forward position. After the flange 706 of the plunger moves while pressing the rear end 710 of the trigger lever 708 (which is constituted so as to receive the force acting toward the inside of the injector due to a leaf spring 712 (shown only in FIG. 35, omitted in other drawings), the rear end 710 of the trigger adjoins at the front side of the flange 706, which leads to achievement of the cocked state of the trigger lever 708. In this state where the trigger lever is cocked, the distance between the rear end 714 of the plunger and the inner wall 716 at the rear end of the injector (specifically, "inner wall 716" is the inner wall surface of an outer drum of the pricking depth adjusting mechanism) may be very small, or may be zero meaning that the rear end 714 and the inner wall 716 are in contact with each other.

When the lancet holder is inserted furthermore, the rear end 592 of the lancet body fits into the front end 702 of the plunger while the rear end 592 and the frond end 702 are still in contact with each other. In the embodiment shown in the drawings, the rear end of the lancet body has the protrusion 594 around thereof, whereas the recessed portion 720 is formed in the plunger by partially slitting the front end of the plunger. Therefore, the protrusion 594 of the lancet body fits into the recessed portion 720 of the plunger. In this case, the rear end of the lancet body forces to expand the front end of the plunger so that the rear end of the lancet body fits into the front end of the plunger. In another embodiment, the rear end portion of the lancet body may fit into the front end of the plunger in a press fitting relationship.

Figure 34:
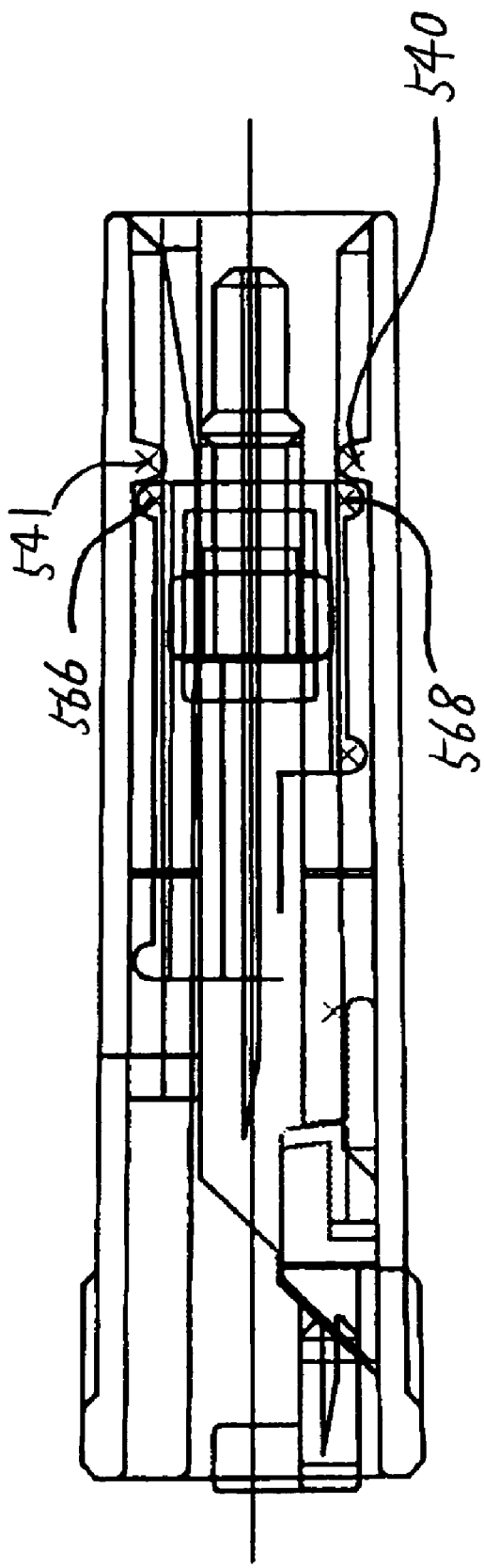
FIG. 34 is a schematic cutaway side view (type B) of the state (showing similarly to FIG. 33) where a protrusion of the lancet body has ridden up and over a protrusion provided between rails of the lancet holder.

Subsequently, the plunger is retracted a little together with the lancet assembly since the rear end 714 of the plunger makes contact with (i.e. abuts against) the inner wall 716 at the rear end of the injector housing. After the rear end 714 makes contact with the inner wall 766, the plunger is prevented from being retracted furthermore. Alternatively, the rear end 714 and the inner wall 716 have been already in contact with each other, and thereby the plunger is substantially unable to be retracted. Subsequently, when the lancet holder is pressed further backward, the protrusion A (568) of the lancet body rides up and over the protrusion B (540) provided between the rails of the lancet holder. The state after the riding over is schematically shown in FIG. 34. The process of the protrusion A (568) riding over the protrusion B (540) will be understood by comparing FIG. 33 and FIG. 34 with each other.

In the state where the protrusions A (566 and 568) of the lancet body have ridden over the protrusions B (540 and 541) and are located forward of the protrusions B as shown in FIG. 34, the lancet body 554 with the tip 590 of the pricking component exposed is able to move forward within the lancet holder while being guided by the rails 571, thus completing the loading operation.

In the state shown in FIG. 34, one stopper protrusion 575 of the lancet body is in a deformed state wherein it is kept pressed inwardly by the slider part 730 provided inside of the front end of the injector body. Whereas the other stopper protrusion 575' is located at a position below the front portion of the trigger lever 708. These are schematically shown in FIG. 35.

Figure 35:
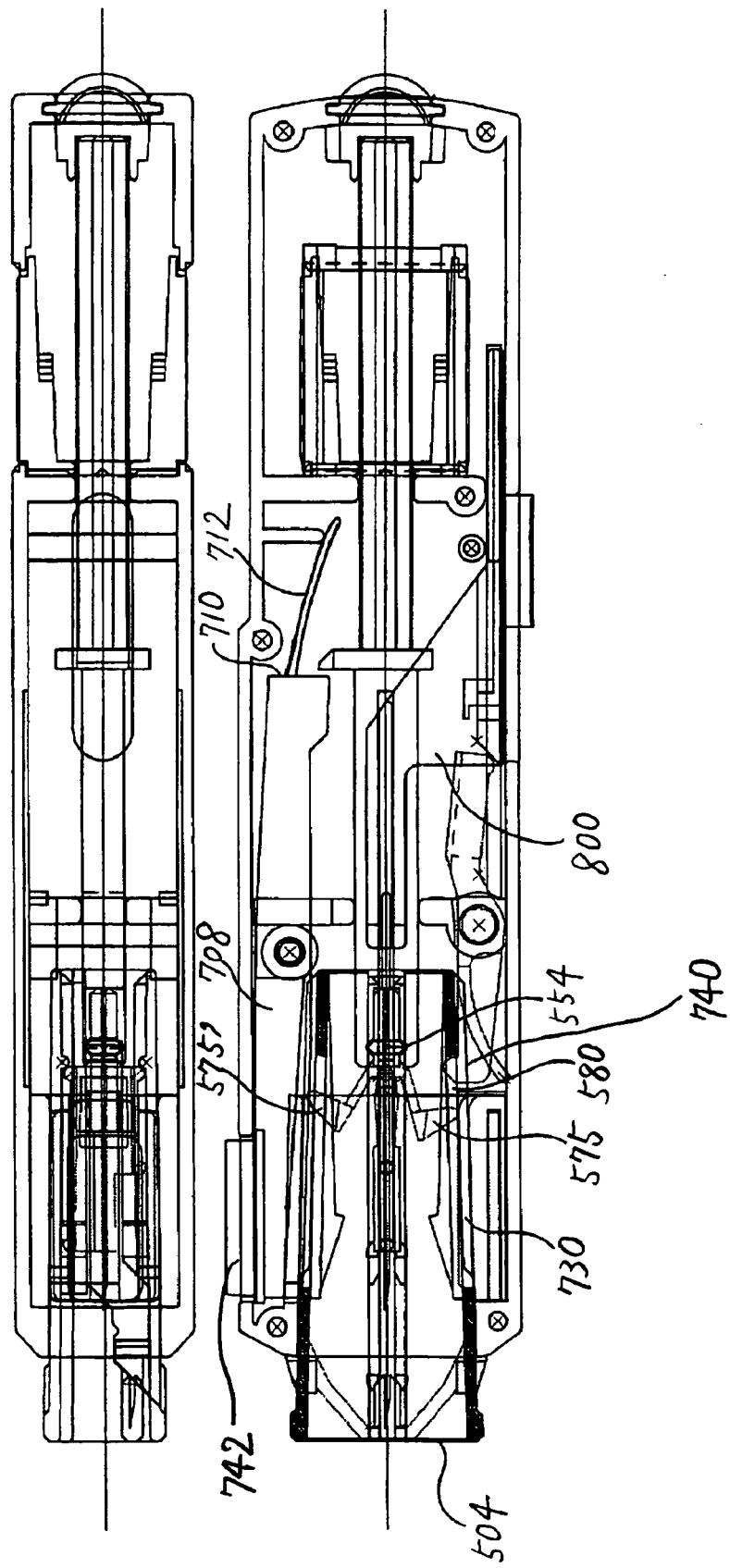
FIG. 35 is a schematic view (type B) of the injector of FIG. 34 and the lancet assembly inserted therein in side view (bottom) and top view (top). The lancet assembly disposed in the injector and the lancet disposed in the lancet holder are illustrated for the ease of understanding.

FIG. 35 schematically shows the inside of the lancet injector of type B as viewed sideways. Since FIG. 35 is complicated, FIG. 36 shows the lancet assembly of FIG. 35 by shifting it to the side.

The injector of type B according to the present invention preferably has a holder lock mechanism. Due to the holder lock mechanism, the lancet holder is surely hold in the injector after the completion of the loading. Specifically, the injector has a hook part 740 capable of fitting into the edge of the elongated opening (which is provided at the side opposite to the trigger lever 708) when insertion of the lancet assembly is completed. The hook part 740 is formed of resilient material to exert the force toward the inside of the injector (see the arrow in FIG. 36). After the lancet holder is caused to move backward (namely the lancet holder is inserted) while the hook part is deformed outwardly by the side wall of the lancet holder against the force of the hook part 740, the end of the hook part can fit into the rear edge of the elongated opening 580. This leads to achievement of the locked state (see FIG. 35). When the locked state is achieved, the lancet holder and the injector are in engagement so that the lancet assembly is prevented from being come off the injector.

Figure 36:
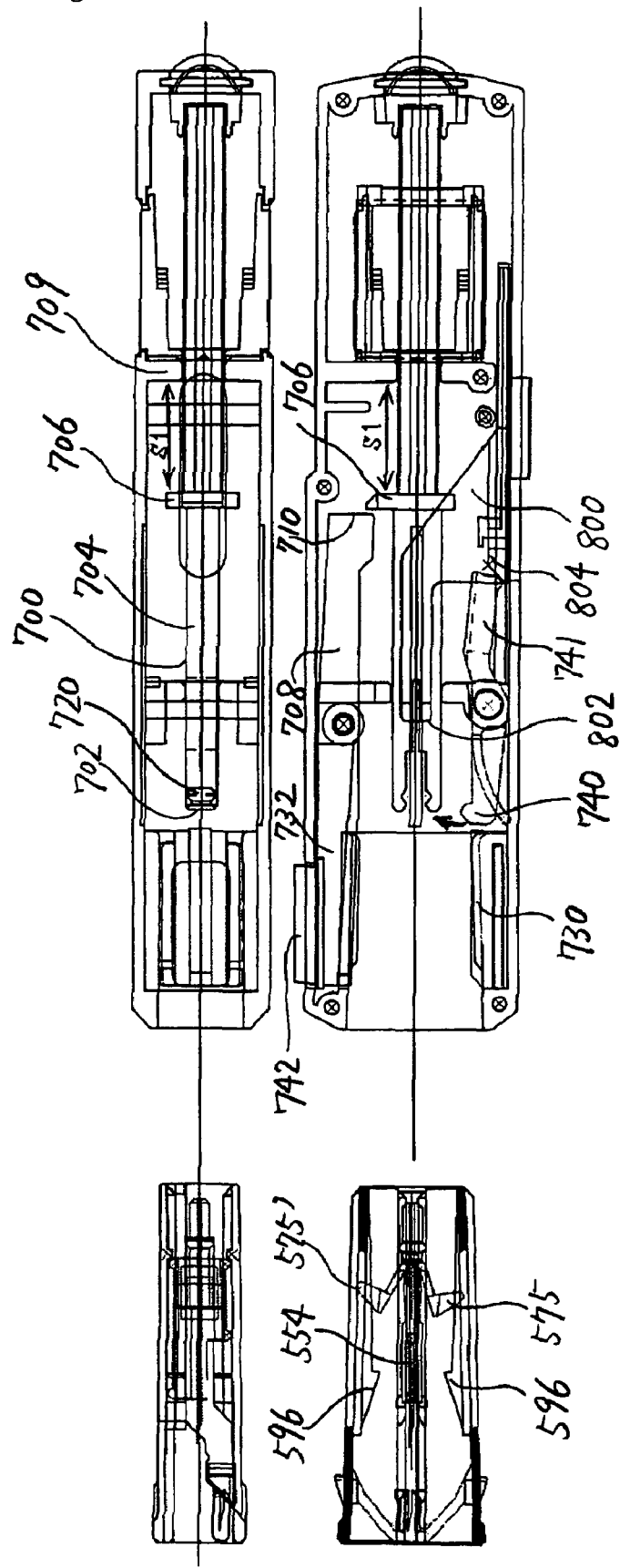
FIG. 36 shows the injector and the lancet assembly of type B wherein the lancet assembly is shifted toward left in the state of FIG. 35 for the ease of understanding.

It is shown in FIG. 35 and FIG. 36 that the lancet body with the tip of the pricking component exposed is ready to be launched. After applying the pricking opening of the lancet holder to the predetermined region, the front portion 742 of the trigger lever 708 is pressed toward the inside of the injector. This pressing causes the cease of the contact between the rear end 710 of the trigger lever 708 and the flange 706 of the plunger, and thereby the compressed spring S1 instantaneously expands so as to launch the lancet body 554 forward.

As will be easily understood from FIG. 35, pressing the front portion 742 of the trigger lever 708 leads to an inward pressing of the one stopper protrusion 575' located inwardly with respect to the trigger lever 708. This results in a deformation of the one stopper protrusion 575', substantially similarly to the other stopper protrusion 575. The deformation of the stopper protrusions must take place before or substantially at the same time as the contact between the rear end of the trigger lever and the flange of the plunger ceases. When the spring instantaneously expands as described above, the lancet body is launched forward while the deformation of both stopper protrusions is maintained. As a result, the both stopper protrusions can move forward without hitting the stopper 596 provided in the holder (i.e. the stopper protrusions do not serve as the stopper), and thereby the tip 590 of the pricking component can protrude outwardly from the pricking opening 504 of the lancet holder. After the tip 590 of the pricking component pricks the predetermined region, it is retracted backward quickly. In this way, the stopper function is not put into effect upon pricking because the lancet is made of resin and the deformed resin component returns to its original shape more slowly than the launching speed of the lancet by the spring.

After the pricking component is retracted, the stopper protrusions 575, 575' return to their original shapes or shapes similar thereto. Then, the forward movement of the lancet body 554 is prevented because the stopper protrusions 575, 575' having their original shapes are able to make contact with or hit the stopper 596 provided in the lancet holder. Thus, the forward movement of the lancet body is restricted after pricking, and thereby the tip 590 of the pricking component does not protrude from the pricking opening 504 of the lancet holder. It should be noted that the backward movement of the lancet body is also restricted by the contact between the protrusions A (566, 568) and the protrusions B (540, 541) within the rails 571. Since the tip 590 of the pricking component does not protrude from the pricking opening 504, the spent lancet assembly can be safely disposed of.

Figure 37:
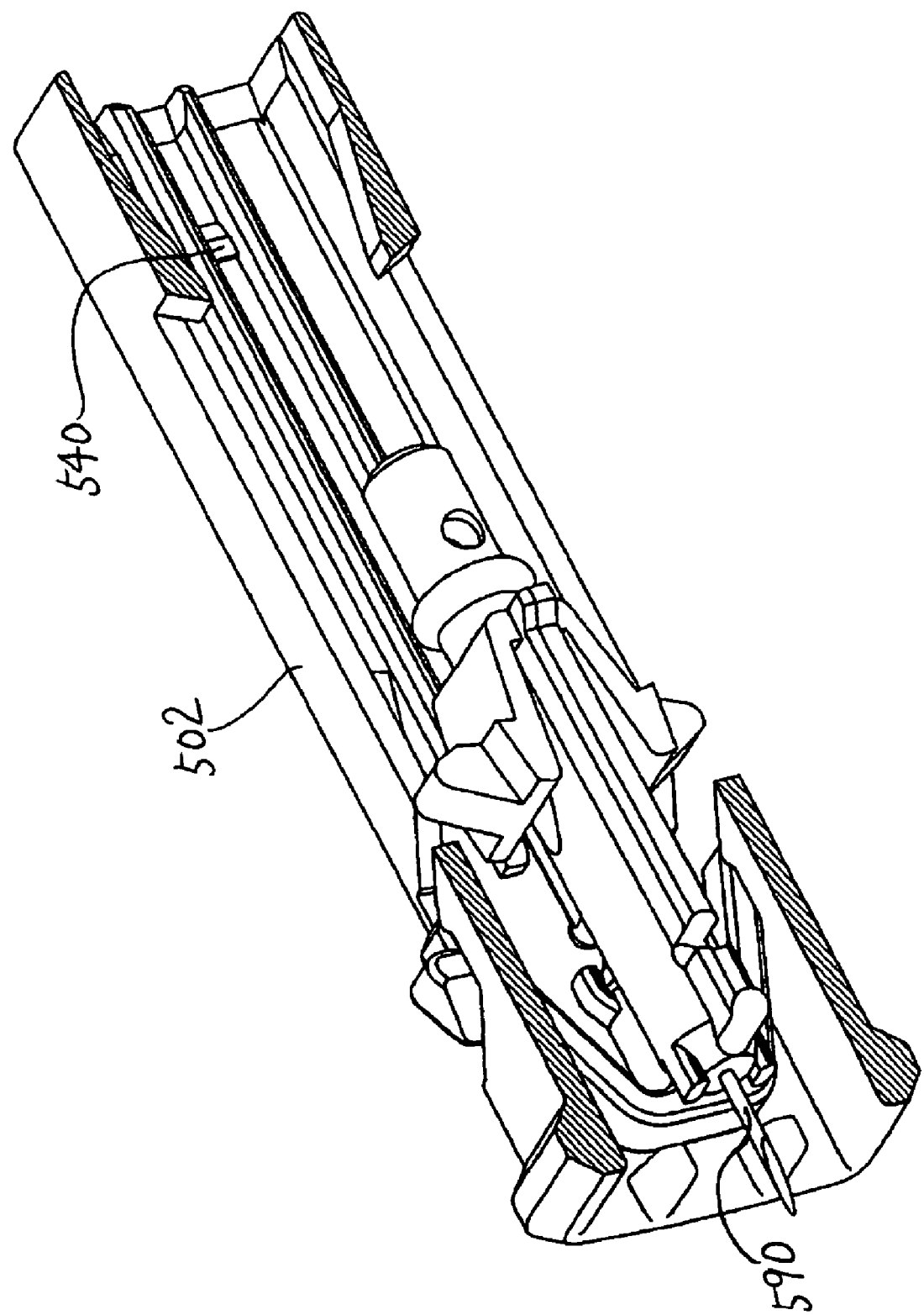
FIG. 37 is a schematic perspective view (type B) of the state (showing similarly to FIG. 32) where the tip of the pricking component is protruding from the lancet holder.
Figure 38:
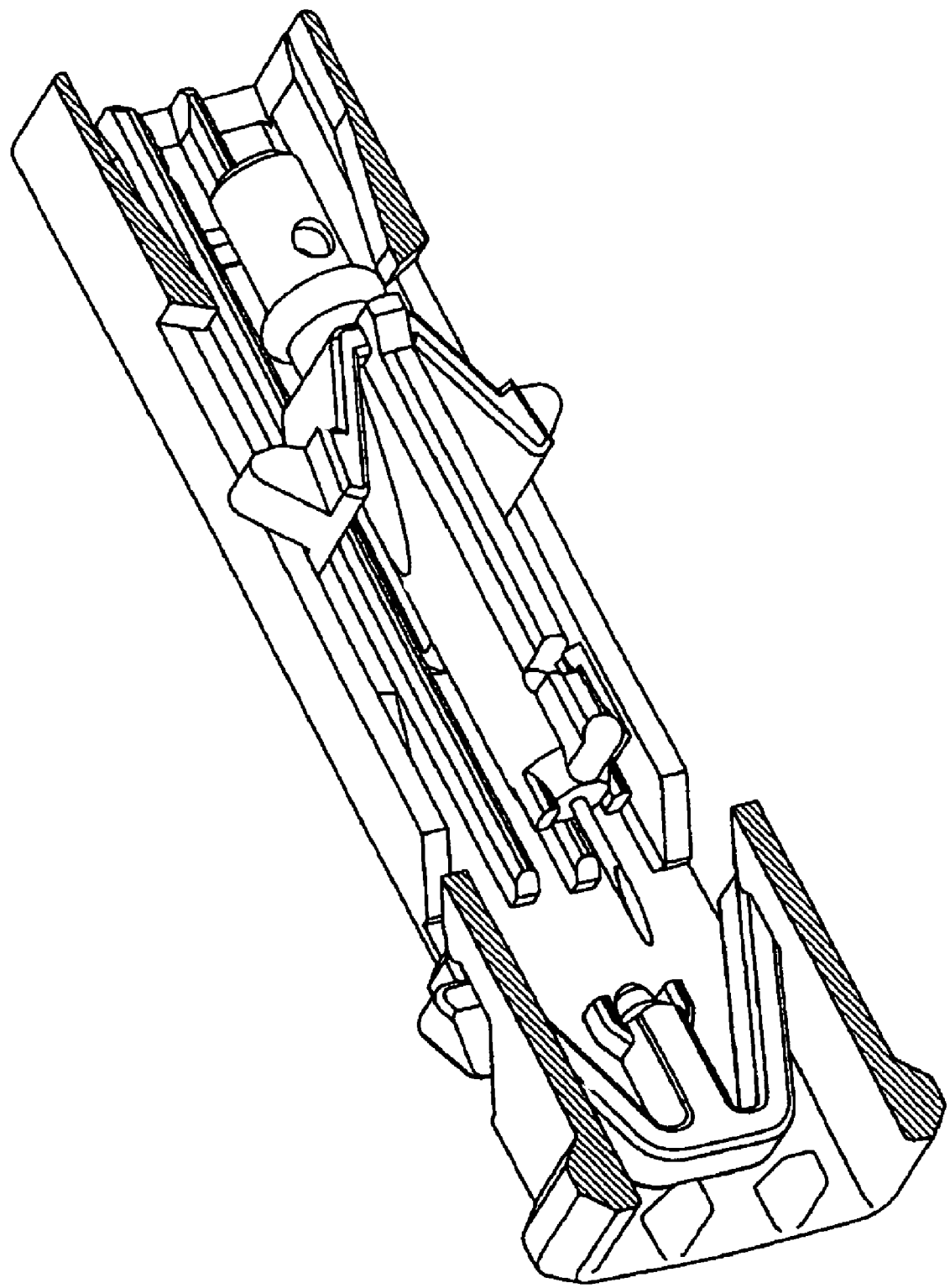
FIG. 38 is a schematic perspective view (type B) of the state (showing similarly to FIG. 32) where the stopper protrusion has returned to its original shape after pricking.

It is shown in perspective view of FIG. 37 that the tip 590 of the pricking component protrudes from the lancet holder upon pricking. It is shown in perspective views of FIG. 38 and FIG. 39 that the stopper protrusions have returned to their original shapes after pricking.

After pricking is completed, the lancet holder 502 containing the lancet body 554 is discharged from the injector 600. The discharging operation is carried out by operating an ejector 800 of the injector, similarly to the case of type A. The ejector 800 has a function of releasing the engagement between the lancet holder and the injector. In other words, the ejector 800 has a function of not only pressing the hook part 740 outwardly so as to release the locked state of the hook part 740 (which is in the fitting relationship with the edge of the elongated opening), but also pressing the rear end 520 of the lancet holder by the front end 802 of the ejector so as to move the lancet holder forward.

Figure 39:
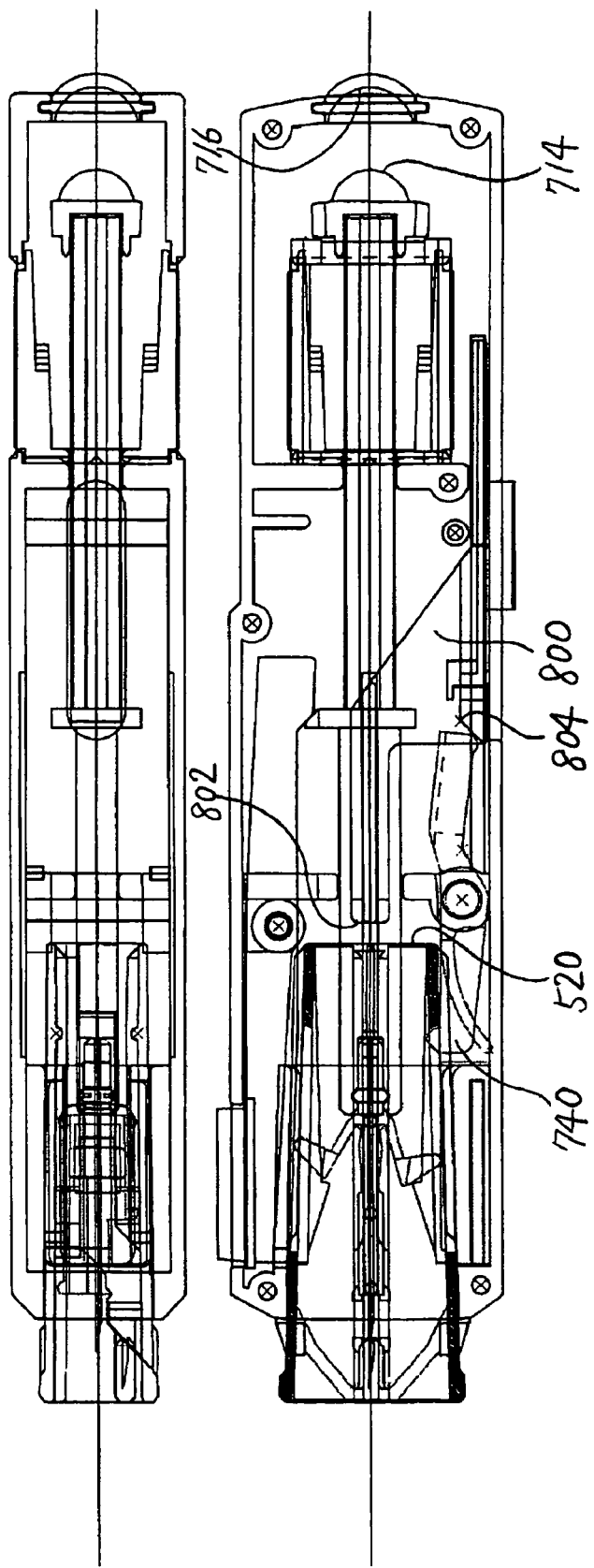
FIG. 39 is a schematic view (type B) of the state (showing similarly to FIG. 35) immediately before the front end 802 of the ejector makes contact with the rear end 520 of the lancet holder.
Figure 40:
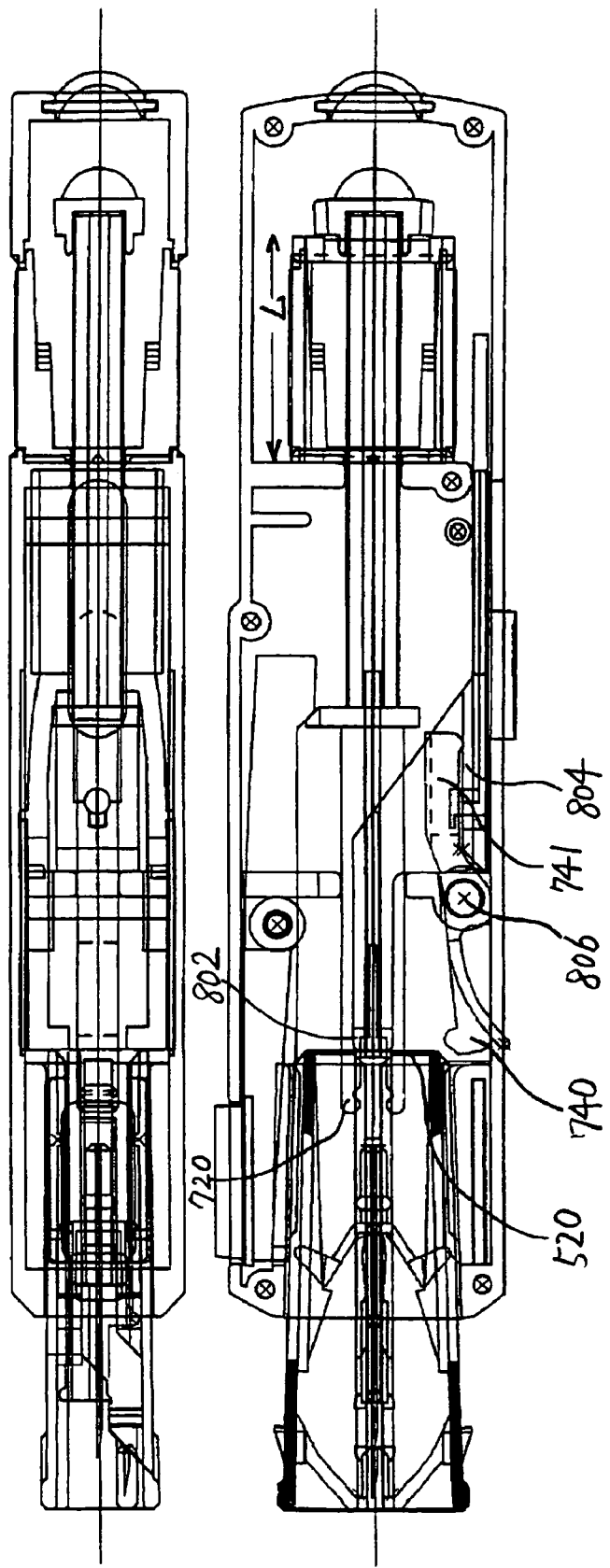
FIG. 40 is a schematic view (type B) of the state (showing similarly to FIG. 35) where the front end of the ejector is pressing the rear end of the lancet holder.

The process of discharging the lancet holder is shown in FIG. 39 and FIG. 40. FIG. 39 shows the state immediately before the front end 802 of the ejector makes contact with the rear end 520 of the lancet holder. To release the locked state of the hook part 740, the sliding portion 804 of the ejector is caused to move forward such that it lies under the rear portion 741 of the hook part, and thereby causing the hook part to move downwardly due to the pivot 806. Subsequently, the front end 802 of the ejector makes contact with (i.e. abuts on) the rear end 520 of the lancet holder so as to move the unlocked holder forward. FIG. 40 shows that the lancet holder is being pressed so that it moves forward.

Similarly to the injector of type A, the injector of type B preferably has a pricking depth adjusting mechanism in the rear portion of the plunger. A configuration and a function of the pricking depth adjusting mechanism of the injector of type B is similar to those of the injector of type A, and description thereof will be omitted to avoid the repetition.

Although the present invention have been described above, those skilled in the art will understand that the present invention is not limited to the above, and various modifications may be made.

For example, taking the lancet assembly 100 of type A as an example, a continuous protrusion indicated by reference numeral 109 in FIG. 4B and FIG. 9A may be provided on the outer surface of the lancet holder 102. This continuous protrusion promotes a smooth insertion of the lancet assembly 100 into the injector 200. In addition, the continuous protrusion 109 has the function of increasing the strength of the lancet holder 102. Moreover, in case where two continuous protrusions 109 are formed substantially parallel to each other on the same surface as shown in the drawing (for example, FIG. 4B or FIG. 9A), there is provided an advantage that the continuous protrusions 109 can serve as "foot", when the lancet holder is placed such that the continuous protrusions 109 face downward.

As for the lancet 150, the bridging component 154 of the lancet 150 may be cut off in advance. No bridging component 154 may be also provided in the lancet 150. That is, instead of the case where the lancet cap 152 and the lancet body 151 are interconnected via the bridging component 154, the lancet cap 152 and the lancet body 151 may be formed separately (i.e. the lancet cap 152 and the lancet body 151 are not in an interconnected form). In case where no bridging component 154 is provided in the lancet 150, the lancet assembly 100 of the present invention has the following configuration and function:

The lancet assembly 100 comprising a lancet 150 and a lancet holder 102 that contains the lancet 150, wherein the lancet 150 comprises a lancet body 151, a lancet cap 152 and a pricking component 153 in which the lancet body 151 and the lancet cap 152 are made of resin and the pricking component 153 is made of metal, the pricking component 153 is situated in both of the lancet body 151 and the lancet cap 152, and the tip of the pricking component 153 is covered with the lancet cap 152;

when the lancet cap 152 is pressed in the pricking direction with the lancet body 151 secured to the lancet holder 102, the lancet cap 152 and the lancet body 151 move away from each other, and thereby the tip of the pricking component 153 is exposed while the pricking component 153 remains situated in the lancet body 151; and when the separated lancet cap 152 is pressed further in the pricking direction, the separated lancet cap 152 moves to a position that is off the pricking pathway of the pricking component 153.

Those skilled in the art will understand that this lancet assembly also has features and functions similar to those of the lancet assembly described previously.

The pricking device composed of the lancet assembly and the injector described above makes it easier and safer to take a sample of the blood. The pricking device is not limited to taking the blood sample of diabetic, and can be used in various applications requiring blood samples.

The invention claimed is:

1. A lancet assembly comprising:
   a lancet; and
   a lancet holder housing the lancet, wherein
   the lancet comprises a lancet body, a lancet cap and a pricking component, the lancet body and the lancet cap being made of resin and the pricking component being made of metal, the pricking component is disposed in both the lancet body and the lancet cap, the tip of the pricking component is covered with the lancet cap, and the lancet cap and the lancet body are integrally connected together by a bridging component; and
   when, a separated lancet cap is pressed in a pricking direction, the separated lancet cap moves to a position that is off the pricking pathway of the pricking component;
   wherein the lancet cap is capable of engaging with a lancet cap removing part disposed in an injector for launching the pricking component;
   the lancet cap removing part is capable of engaging the lancet cap when the lancet assembly with the lancet body secured to the lancet holder is loaded into the injector by inserting the lancet holder into the injector through a front end opening of the injector;
   the lancet holder is configured to be inserted when the lancet cap removing part and the lancet cap are engaged, a force for pressing the lancet cap in a pricking direction is generated so that the bridging component is broken and the lancet cap is separated from the lancet body, and thereby the tip of the pricking component is exposed while the pricking component remains disposed in the lancet body, the pricking direction being in the same direction as the pricking pathway; and
   when the lancet holder is further inserted, the separated lancet cap moves to the position off the pricking pathway within the lancet holder.

2. The lancet assembly according to claim 1, wherein the lancet holder has, on an inner wall, a guide configured to guide the lancet body along the pricking direction, and the lancet body has a guided component that fits with the guide of the lancet holder; and
   first and second protrusions on the guided component and a third protrusion of the guide are in contact with each other such that the third protrusion is disposed between the first and second protrusions, and thereby the lancet body is secured to the lancet holder.

3. The lancet assembly according to claim 1, wherein the bridging component has a notch.

4. The lancet assembly according to claim 1, wherein the lancet is housed in the lancet holder so that the lancet does not protrude from the lancet holder; and
   the lancet holder has at least two end faces, and each end face of the two end faces has an opening, and the lancet holder has no openings on side faces thereof.

5. The lancet assembly according to claim 4, wherein one opening of the openings of the lancet holder is a pricking opening; and
   the pricking opening has a diameter in a range from 0.5 to 2.0 mm.

6. The lancet assembly according to claim 1, wherein the lancet cap comprises a pair of first wing parts extending backward.

7. The lancet assembly according to claim 6, wherein the edge of each first wing part of the lancet cap has an engagement portion that is capable of complementarily engaging with an end portion of the lancet cap removing part.

8. The lancet assembly according to claim 1, wherein the lancet holder has a slope component configured to guide the separated lancet cap to the position that is off the pricking pathway; and
   the lancet cap includes a sloped portion that has a shape corresponding to the slope component.

9. The lancet assembly according to claim 1, wherein
   a rear end portion of the lancet body has an engagement portion that is capable of engaging with a plunger disposed in the injector;
   the rear end portion of the lancet body and a front end portion of the plunger are configured and arranged to engage each other when the lancet assembly is loaded into the injector by inserting the lancet holder into the injector through the front end opening of the injector, and thereby, when the lancet holder is inserted further, the plunger is retracted so that the force required for launching the pricking component is stored in the plunger.

10. The lancet assembly according to claim 9, wherein
    the lancet holder has, on an inner wall, a guide channel configured to guide the lancet body along the pricking direction whereas the lancet body has a guided component that fits with the guide channel of the lancet holder;
    the first protrusion on the guided component and the second protrusion of the guide channel are in contact with each other so that the lancet body is secured to the lancet holder; and
    after the lancet cap is separated from the lancet body upon the loading of the lancet assembly into the injector, the plunger is prevented from being retracted further, so that the lancet body that is in engagement with the plunger is prevented from being further inserted; and
    thereafter, when the lancet holder is forced to move further in a direction of insertion, the first protrusion passes over the second protrusion and the contact between the first protrusion and the second protrusion ceases, thereby the lancet body can move along the guide channel in the pricking direction.

11. The lancet assembly according to claim 1, wherein the lancet body has a pair of second wing parts extending forward;
    in the lancet assembly that has been ejected from the injector after pricking, the pair of second wing parts is capable of contacting a stopper surface disposed within the lancet holder so that the tip of the pricking component does not protrude from the pricking opening.

12. The lancet assembly according to claim 11, wherein a rear end face of a slope component configured to guide the separated lancet cap off the pricking pathway serves as the stopper surface.

13. The lancet assembly according to claim 11, wherein the lancet cap removing part of the injector includes a groove ; and
when the pricking component is ready to be launched, the pair of second wing parts lies in the groove.

14. The lancet assembly according to claim 13, wherein the groove is bow-shaped.

15. The lancet assembly according to claim 13, wherein
upon pricking, the pair of second wing parts moves along the groove without making contact with the stopper surface.

16. The lancet assembly according to claim 11, wherein the lancet cap removing part has a bow-shaped groove; and
when the lancet cap removing part engages with the lancet cap upon the loading of the lancet assembly into the injector, the pair of second wing parts is placed in the bow-shaped groove.

17. The lancet assembly according to claim 1, further comprising:
the injector, the injector comprising:
a plunger capable of engaging with a rear end portion of the lancet body, and capable of launching the lancet body in the pricking direction;
the lancet cap removing part capable of engaging the lancet cap; and
a trigger lever that is capable of being pressed so as to launch the pricking component, wherein
the lancet assembly configured to be loaded into the injector by inserting the lancet holder into the injector through the front end opening of the injector;
when the lancet assembly with the lancet body secured to the lancet holder is loaded into the injector, the lancet cap removing part is capable of engaging the lancet cap; and
when the lancet holder is further inserted while the lancet cap removing part and the lancet cap are engaged, the force for separating the lancet cap from the lancet body or for moving the lancet cap and the lancet body away from each other is generated, and the separated lancet cap is capable of moving to the position that is off the pricking pathway of the pricking component.

18. The lancet assembly according to claim 17, wherein a spring is disposed around the plunger between a flange formed around an intermediate portion of the plunger and a partition provided in an injector housing;
upon the loading of the lancet assembly into the injector, the rear end portion of the lancet body engages with the front end portion of the plunger so that the plunger is capable of being retracted, and thereby compressing the spring;
when the plunger is retracted, the flange of the plunger moves to a position rearward of a rear stepped portion of the trigger lever, and thereafter the flange of the plunger engages with the rear stepped portion while the compressed spring is maintained.

19. The lancet assembly according to claim 17, further comprising a pricking depth adjusting mechanism, the pricking depth adjusting mechanism comprising:
a protrusion disposed on the rear end portion of the plunger, protruding outwardly from the plunger in a transverse direction thereof; and
a cylindrical component with graduated stepped portions of various heights, wherein
when the plunger moves forward for pricking, the protrusion disposed on the rear end portion of the plunger hits the stepped portions of the cylindrical component so that the plunger is unable to move further forward, and
the stepped portions which the protrusion hits are capable of being switched to other stepped portions with different heights by rotating the cylindrical component about a center axis, and thereby the distance over which the plunger is capable of moving forward for pricking is changed.

20. The lancet assembly according to claim 19, wherein a pricking opening has a diameter in a range from 0.5 to 2.0 mm so that a pricking depth set by the pricking depth adjusting mechanism is less likely to be affected by the force applied to a region to be pricked.

21. The lancet assembly according to claim 17, further comprising an ejector; and
the lancet holder is configured to be pressed forward by sliding the ejector forward, and thereby the lancet assembly is capable of being ejected from the injector.

22. A lancet assembly comprising:
a lancet; and
a lancet holder housing the lancet, wherein
the lancet comprises a lancet body, a lancet cap and a pricking component, the lancet body and the lancet cap being made of resin and the pricking component being made of metal, the pricking component is disposed in both the lancet body and the lancet cap, and the tip of the pricking component is covered with the lancet cap;
when a separated lancet cap is pressed in a pricking direction, the separated lancet cap moves to a position that is off a pricking pathway of the pricking component;
wherein the lancet cap is capable of engaging with a lancet cap removing part disposed in an injector for launching the pricking component;
the lancet cap removing part is capable of engaging the lancet cap when the lancet assembly with the lancet body secured to the lancet holder is loaded into the injector by inserting the lancet holder into the injector through the front end opening of the injector;
the lancet holder is configured to be inserted when the lancet cap removing part and the lancet cap are engaged, the force for pressing the lancet cap in the pricking direction is generated so that the bridging component is broken and the lancet cap is separated from the lancet body, and thereby the tip of the pricking component is exposed while the pricking component remains disposed in the lancet body, the pricking direction being in the same direction as the pricking pathway; and
when the lancet holder is further inserted, the separated lancet cap moves to the position off the pricking pathway within the lancet holder.

23. A lancet of a lancet assembly, comprising:
a lancet body, a lancet cap and a pricking component, the lancet body and the lancet cap being made of resin and the pricking component being made of metal, the pricking component is disposed in both the lancet body and the lancet cap, the tip of the pricking component is covered with the lancet cap, and the lancet cap and the lancet body are integrally connected together by a bridging component;
wherein the lancet cap is configured to be pressed in a pricking direction such that the bridging component is broken so that the lancet cap is separated from the lancet body, and thereby the tip of the pricking component is exposed while the pricking component remains disposed in the lancet body, the pricking direction being in the same direction as the pricking pathway; and when the separated lancet cap is pressed further in the pricking direction, the separated lancet cap moves to a position that is off the pricking pathway of the pricking component;

wherein the lancet cap is capable of engaging with a lancet cap removing part disposed in an injector for launching the pricking component;

the lancet cap removing part is capable of engaging the lancet cap when the lancet cap, which is configured to be secured to a lancet holder, is loaded into the injector by inserting the lancet holder into the injector through a front end opening of the injector; and the separated lancet cap is configured to move to the position off the pricking pathway within the lancet holder, when the lancet holder is inserted.

* * * * *